US012662662B2

(12) United States Patent
Lu et al.

(10) Patent No.: US 12,662,662 B2
(45) Date of Patent: Jun. 23, 2026

(54) MUTATIONS FOR IMPROVING ACTIVITY AND THERMOSTABILITY OF PETASE ENZYMES

(71) Applicant: Board of Regents, the University of Texas System, Austin, TX (US)

(72) Inventors: Hongyuan Lu, Austin, TX (US); Daniel Diaz, Austin, TX (US); Hannah Cole, Austin, TX (US); Raghav Shroff, Austin, TX (US); Andrew Ellington, Austin, TX (US); Hal Alper, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 18/247,957

(22) PCT Filed: Oct. 5, 2021

(86) PCT No.: PCT/US2021/053530
§ 371 (c)(1),
(2) Date: Apr. 5, 2023

(87) PCT Pub. No.: WO2022/076380
PCT Pub. Date: Apr. 14, 2022

(65) Prior Publication Data
US 2026/0117209 A1        Apr. 30, 2026

Related U.S. Application Data

(60) Provisional application No. 63/088,321, filed on Oct. 6, 2020.

(51) Int. Cl.
*C12N 9/18*        (2006.01)
*C08J 11/10*        (2006.01)
(Continued)

(52) U.S. Cl.
CPC ............... *C12N 9/18* (2013.01); *C08J 11/105* (2013.01); *C12N 15/78* (2013.01); *C07K 2319/02* (2013.01); *C12R 2001/40* (2021.05)

(58) Field of Classification Search
CPC ...................................................... C12N 9/18
See application file for complete search history.

(56) References Cited

U.S. PATENT DOCUMENTS

2020/0048621 A1*    2/2020   Kim .......................... C12N 1/20

FOREIGN PATENT DOCUMENTS

CN        107674866        2/2018
CN        111057693        4/2020

OTHER PUBLICATIONS

Chen. Structure-based engineering of PET hydrolase from Ideonella sakaiensis]. Sheng Wu Gong Cheng Xue Bao. Sep. 25, 2021;37 (9):3268-3275.*

(Continued)

*Primary Examiner* — Yong D Pak
(74) *Attorney, Agent, or Firm* — pH IP Law

(57)        ABSTRACT

This invention relates to engineered plastic-degrading enzymes with improved functional features. In particular, modified PETases capable of hydrolysis of PET or polyethylene terephthalate plastic polymer are disclosed herein. These engineered PETases contain one or more amino acid modifications at specified residue or residues, for example, N233, and exhibit improved enzymatic activity as well as thermostability.

18 Claims, 23 Drawing Sheets

Specification includes a Sequence Listing.

Esterase activity: IsPETase mutants VS. Dead/Thermo/WT

(51) Int. Cl.
*C12N 15/78* (2006.01)
*C12R 1/40* (2006.01)

(56) References Cited

OTHER PUBLICATIONS

EP Application No. 21878340.5, Supplementary European Search Report dated Jan. 13, 2025, 12 pages.

Son Hyeoncheol Francis et al, "Rational Protein Engineering of Thermo-Stable PETase from Ideonella sakaiensis for Highly Efficient PET Degradation", Mar. 11, 2019, 8 pages.

"*Escherichia coli* mutant 1208V Pet hydrolase, SEQ ID 3.", XP002812312, retrieved from EBI accession No. GSP: BEY95831Database accession No. BEY95831* sequence *, Apr. 5, 2018, 1 page.

"Ideonella sakaiensis PETase S121E variant.", XP002812235, retrieved from EBI accession No. GSP:BHI31735 Database accession No. BHI31735 * sequence *, Apr. 2, 2020, 1 page.

"Ideonella sakaiensis PET hydrolase protein mutant/N204H, SEQ 20.", XP002812313, retrieved from EBI accession No. GSP:BHT18782 Database accession No. BHT18782 * sequence *, Jun. 25, 2020, 1 page.

Austin et al (2018), "Characterization and engineering of a plastic-degrading aromatic polyesterase", Proceedings of the National Academy of Sciences of the United States of America, 115(19), E4350-E4357, 8 pages.

Franden et al. (2018), "Engineering Pseudomonas putida KT2440 for efficient ethylene glycol utilization", Metabolic Engineering, 48(Dec. 2017), 197-207, 15 pages.

Han et al. (2017), "Structural insight into catalytic mechanism of PET hydrolase", Nature Communications, 8(1), 6 pages.

Joo et al. (2018), "Structural insight into molecular mechanism of poly(ethylene terephthalate) degradation" Nature Communications, 9(1), 12 pages.

Seo et al. (2019), Production of extracellular PETase from Ideonella sakaiensis using sec-dependent signal peptides in *E. coli*. Biochemical and Biophysical Research Communications, 508(1), 250-255, 6 pages.

Yoshida et al. (2016), A bacterium that degrades and assimilates poly(ethylene terephthalate). Science, 351(6278), 1196 LP-1199, 4 pages.

PCT/US2021/053530, "International Preliminary Report on Patentability", Apr. 20, 2023, 7 pages.

PCT/US2021/053530, "International Search Report and Written Opinion", Feb. 2, 2022, 6 pages.

* cited by examiner

Figure 7, continued
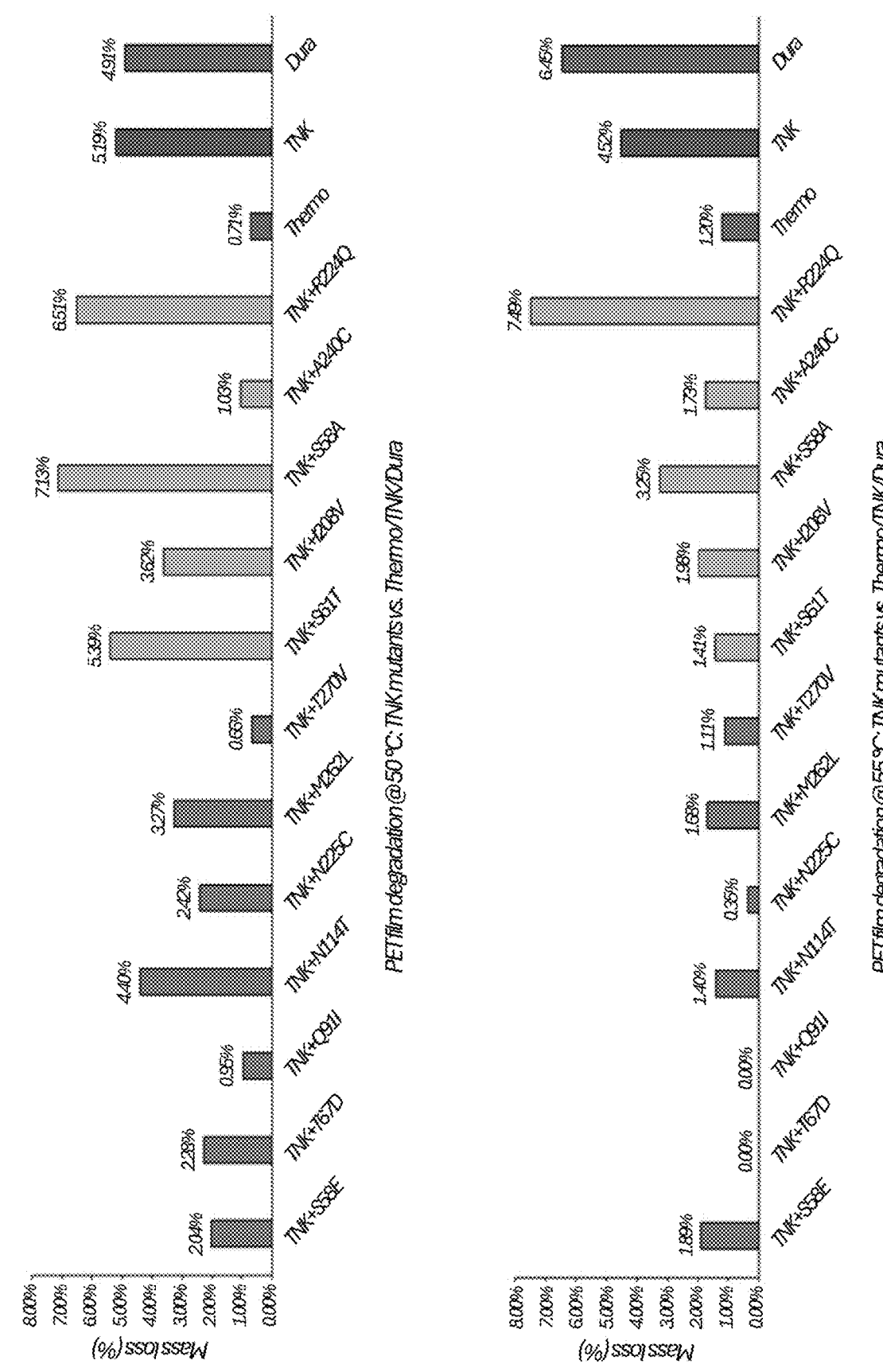

Figure 8

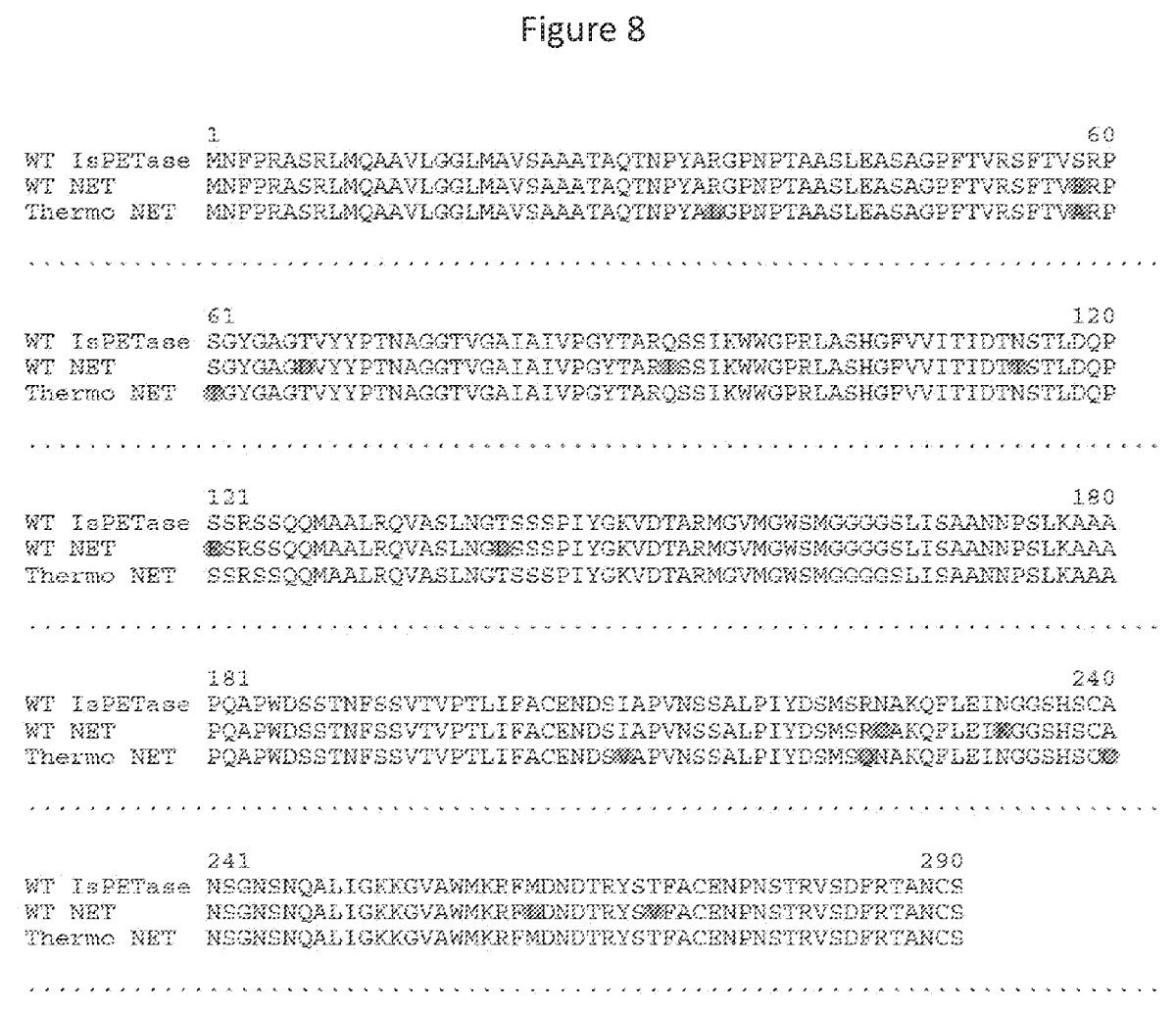

```
                                                                           60
WT IsPETase   1   MNFPRASRLMQAAVLGGLMAVSAAATAQTNPYARGPNPTAASLEASAGPFTVRSFTVSRP
WT NET            MNFPRASRLMQAAVLGGLMAVSAAATAQTNPYARGPNPTAASLEASAGPFTVRSFTV?RP
Thermo NET        MNFPRASRLMQAAVLGGLMAVSAAATAQTNPYA?GPNPTAASLEASAGPFTVRSFTV?RP 120
WT IsPETase  61   SGYGAGTVYYPTNAGGTVGAIAIVPGYTARQSSIKWWGPRLASHGFVVITIDTNSTLDQP
WT NET            SGYGA??NYYPTNAGGTVGAIAIVPGYTAR?SSIKWWGPRLASHGFVVITIDT?STLDQP
Thermo NET        ??YGAGTVYYPTNAGGTVGAIAIVPGYTARQSSIKWWGPRLASHGFVVITIDTNSTLDQP 180
WT IsPETase 131   SSRSSQQMAALRQVASLNGTSSSPIYGKVDTARMGVMGWSMGGGGSLISAANNPSLKAAA
WT NET            ?SRSSQQMAALRQVASLNGTSSG?SSPIYGKVDTARMGVMGWSMGGGGSLISAANNPSLKAAA
Thermo NET        SSRSSQQMAALRQVASLNGTSSG?SSPIYGKVDTARMGVMGWSMGGGGSLISAANNPSLKAAA 240
WT IsPETase 181   PQAPWDSSTNFSSVTVPTLIFACENDSIAPVNSSALPIYDSMSRNAKQFLEINGGSHSCA
WT NET            PQAPWDSSTNFSSVTVPTLIFACENDSIAPVNSSALPIYDSMSR?AKQFLE?GGSHSCA
Thermo NET        PQAPWDSSTNFSSVTVPTLIFACENDS?APVNSSALPIYDSMS??NAKQFLEINGGSHSQ?

290
WT IsPETase 241   NSGNSNQALIGKNGVAWMKRFMDNDTRYSTFACENPNSTRVSDFRTANCS
WT NET            NSGNSNQALIGKKGVAWMKRF?DNDTRYS?FACENPNSTRVSDFRTANCS
Thermo NET        NSGNSNQALIGKKGVAWMKRFMDNDTRYSTFACENPNSTRVSDFRTANCS
```

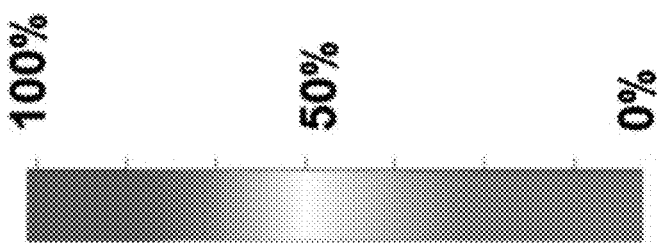
Figure 9A
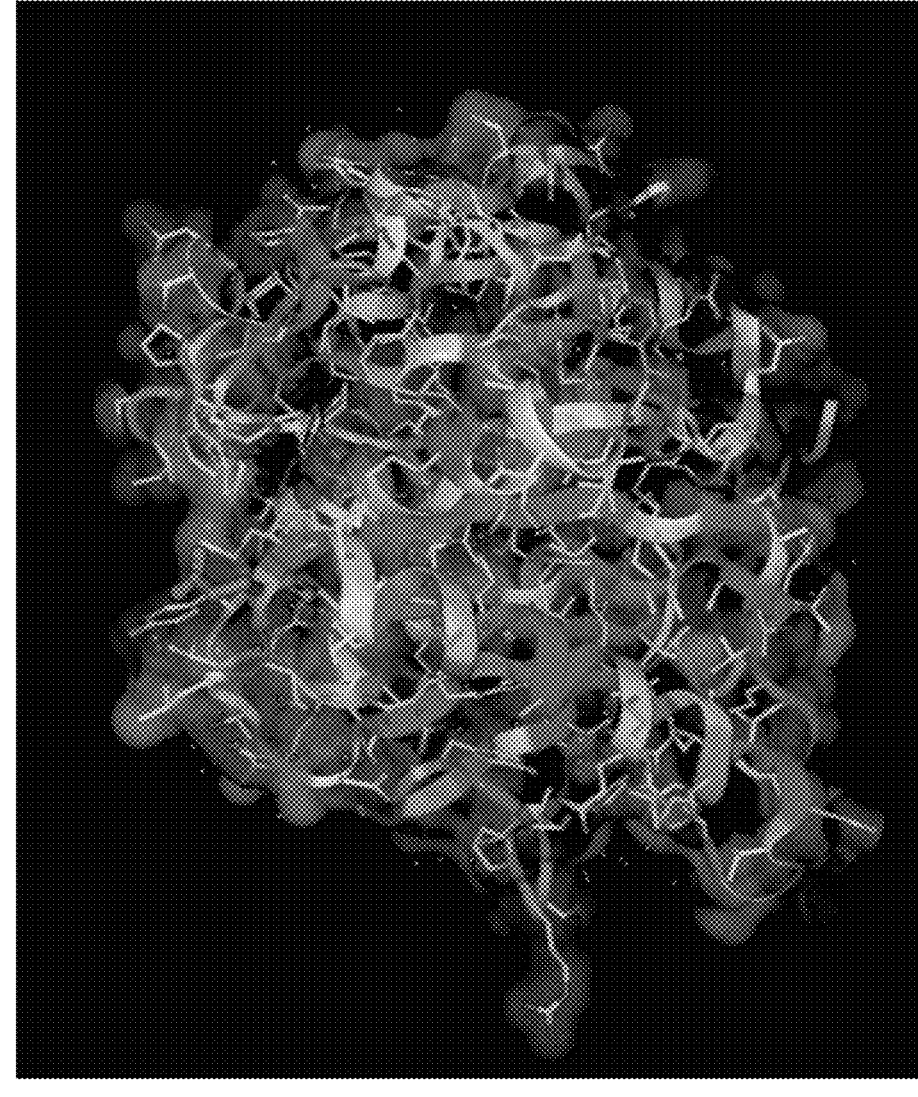

| Sample number | Postconsumer Plastic products | Initial mass (mg) | Crystallinity % | Time for complete degradation (days) | Category |
|---|---|---|---|---|---|
| #1 | | $10.57 \pm 0.02$ | $1.20\% \pm 0.09\%$ | 3.5 | Food packaging |
| #2 | | $6.36 \pm 0.07$ | $1.21\% \pm 0.09\%$ | 2.5 | Household goods packaging |
| #3 | | $16.27 \pm 0.52$ | $1.23\% \pm 0.20\%$ | 4.5 | Beverage packaging |
| #4 | | $12.34 \pm 0.11$ | $1.30\% \pm 0.14\%$ | 4 | Household goods packaging |
| #5 | | $8.28 \pm 0.48$ | $1.40\% \pm 0.14\%$ | 3 | Food packaging |
| #6 | | $15.75 \pm 0.11$ | $1.42\% \pm 0.29\%$ | 4.5 | Food packaging |
| #7 | | $4.86 \pm 0.32$ | $1.44\% \pm 0.25\%$ | 2 | Household goods packaging |
| #8 | | $6.41 \pm 0.23$ | $1.54\% \pm 0.13\%$ | 2.5 | Office supplies packaging |
| #9 | | $8.76 \pm 0.24$ | $1.55\% \pm 0.22\%$ | 2 | Office supplies packaging |
| #10 | | $9.46 \pm 0.2$ | $1.65\% \pm 0.08\%$ | 2.5 | Food packaging |

MUTATIONS FOR IMPROVING ACTIVITY AND THERMOSTABILITY OF PETASE ENZYMES

CROSS-REFERENCE TO RELATED PATENT APPLICATION

The present application is the U.S. National Phase of PCT/US2021/053530, filed Oct. 5, 2021, which claims benefit of priority to U.S. Provisional Patent Application No. 63/088,321, filed Oct. 6, 2020, which is incorporated by referenced for all purposes.

SEQUENCE LISTING

The instant application contains a Sequence Listing which has been submitted electronically in ASCII format and is hereby incorporated by reference in its entirety. Said ASCII copy, created on Sep. 8, 2023, is named 093331-1380297_009910US_SL Sep. 8, 2023.txt and is 85,834 bytes in size.

BACKGROUND OF THE INVENTION

Nowadays, plastics have become the most ubiquitous man-made materials in our daily life. Due to their excellent physical and chemical properties, they have been manufactured to a wide variety of products that are indispensable in many industries, such as packaging, clothing, automotive, electronics, household, agriculture, building and construction. The global production of plastics has reached 359 million tonnes in 2018, yet our current demand for plastics is still rapidly increasing.

Ironically, while most plastics are short-lived products that are designed for single use, they have a remarkably long lifespan attributed to their highly stable molecular structure. As a result of the ever-increased production and consumption of the recalcitrant plastic products, the accumulation of plastic waste has posed a growing threat to our ecosystems. Conventional plastic waste management technologies, such as combustion or pyrolysis, are often energy-intensive processes that could produce additional environmental pollutants. In contrast, the recently emerged enzymatic degradation of hydrolysable plastics can function under mild conditions and potentially recover plastics monomers from the depolymerization reaction. Thus, it has caught much attention from both academic and industrial communities. In particular, considerable progress has been made recently with enzymatic hydrolysis of PET, the fourth-most-produced plastic polymer.

Over the past decade, a number of enzymes were found to be capable of cleaving the ester bond between the PET monomers: terephthalate (TPA) and ethylene glycol (EG). Representatively, TfCut1 and TfCut2 from *Thermobifida fusca* KW3 (Furukawa, Makoto et al., 2019. "Efficient Degradation of Poly(Ethylene Terephthalate) with *Thermobifida Fusca* Cutinase Exhibiting Improved Catalytic Activity Generated Using Mutagenesis and Additive-Based Approaches." Scientific Reports. https://doi.org/10.1038/s41598-019-52379-z; Then et al. 2016; 2015; Herrero Acero et al. 2011), Cut190 from Saccharomonospora *viridis* AHK 190 (Oda, Masayuki et al., 2018. "Enzymatic Hydrolysis of PET: Functional Roles of Three Ca2+ Ions Bound to a Cutinase-like Enzyme, Cut190*, and Its Engineering for Improved Activity." Applied Microbiology and Biotechnology. https://doi.org/10.1007/s00253-018-9374-x; Kawai, Fusako et al., 2014. "A Novel Ca2+-Activated, Thermostabilized Polyesterase Capable of Hydrolyzing Polyethylene Terephthalate from Saccharomonospora *Viridis* AHK190." Applied Microbiology and Biotechnology. https://doi.org/10.1007/s00253-014-5860-y), and LC-cutinase derived from leaf compost metagenome (Tournier, V. et al., 2020. "An Engineered PET Depolymerase to Break down and Recycle Plastic Bottles." Nature. https://doi.org/10.1038/s41586-020-2149-4; Shirke, Abhijit N et al., 2018. "Stabilizing Leaf and Branch Compost Cutinase (LCC) with Glycosylation: Mechanism and Effect on PET Hydrolysis." Biochemistry. https://doi.org/10.1021/acs.biochem.7b01189) have been reported to have relatively high PET-degrading activity compared to other PET hydrolases. However, these enzymes exhibit very low activity at mild temperature, and require considerably high operational temperatures (>60° C.) to carry out their optimum activity, limiting their application in whole-cell biocatalyst as environmental remediation strategy. Recently, Yoshida et. al reported that a novel PET-assimilating bacterium *Ideonella sakaiensis* 201-F6 was successfully isolated from a PET bottle recycling site Yoshida, Shosuke et al., 2016. "A Bacterium That Degrades and Assimilates Poly(Ethylene Terephthalate)." Science 351 (6278): 1196 LP-1199. https://doi.org/10.1126/science.aad6359. This bacterium secreted a cutinase-like enzyme—IsPETase that exhibits the highest PET degradation activity among other PET-degrading enzymes identified so far at ambient temperature, indicating its promising environmental applicability. To develop a whole-cell biocatalyst system for environmental PET remediation, researchers have attempted to install IsPETase in several different chassis, including yeast (*Pichia pastoris* GS115, *Yarrowia lipolytica* IMUFRJ 50,682) (Costa, Andressa Maio da et al., 2020. "Poly(Ethylene Terephthalate) (PET) Degradation by *Yarrowia Lipolytica*: Investigations on Cell Growth, Enzyme Production and Monomers Consumption." Process Biochemistry. https://doi.org/10.1016/j.procbio.2020.04.001; Chen, Zhuozhi et al., 2020. "Efficient Biodegradation of Highly Crystallized Polyethylene Terephthalate through Cell Surface Display of Bacterial PETase." Science of the Total Environment. https://doi.org/10.1016/j.scitotenv.2019.136138), and microalga (*Phaeodactylum tricornutum*, *Chlamydomonas reinhardtii* CC-124 and CC-503) (Kim, Ji Won et al., 2020. "Functional Expression of Polyethylene Terephthalate-Degrading Enzyme (PETase) in Green Microalgae." Microbial Cell Factories. https://doi.org/10.1186/s12934-020-01355-8; Moog, Daniel et al., 2019. "Using a Marine Microalga as a Chassis for Polyethylene Terephthalate (PET) Degradation." Microbial Cell Factories. https://doi.org/10.1186/s12934-019-1220-z).

However, one major defect of IsPETase is that it is a heat-labile enzyme which exhibits a melting temperature $(T_m)$ of only 48.8° C. It has been reported that IsPETase lost most of its enzyme activity after 24 hours of incubation at 30° C. (Son, Hyeoncheol Francis et al., 2019. "Rational Protein Engineering of Thermo-Stable PETase from *Ideonella* Sakaiensis for Highly Efficient PET Degradation." ACS Catalysis 9(4): 3519-26. https://doi.org/10.1021/acscatal.9b00568). Nonetheless, to maximize the degradation efficiency, it is more ideal that the PET-degrading enzyme applied in bioremediation can retain its enzymatic activity for a long period of time even under the harsh extracellular environment (e.g., conditions outside of the optimal conditions (temperature, pH, salt concentrations) of the wild-type PETase). Apparently, the low thermal stability of IsPETase will hamper its utilization for practical enzymatic degradation of PET. In order to improve the activity and stability of IsPETase, substantial research efforts have been made to determine the crystal structures of IsPETase and elucidate its catalytic mechanism (Joo, Seongjoon et al., 2018. "Structural Insight into Molecular Mechanism of Poly(Ethylene Terephthalate) Degradation." Nature Communications. https://doi.org/10.1038/s41467-018-02881-1; Austin, Harry P. et al., 2018. "Characterization and Engineering of a Plastic-Degrading Aromatic Polyesterase." Proceedings of the National Academy of Sciences of the United States of America. https://doi.org/10.1073/pnas. 1718804115), opening new opportunities for rational protein engineering of this enzyme. Employing the structural information on IsPETase, several studies have successfully introduced single point mutations that could afford 1.2- to 3.1-fold higher catalytic activity for PETdegradation (Taniguchi, Ikuo et al., 2019. "Biodegradation of PET: Current Status and Application Aspects." ACS Catalysis 9 (5). https://doi.org/10.1021/acscatal.8b05171). Recently, Son et. al created an IsPETase$^{S121E/D186H/R280A}$ variant that exhibits enhanced thermal stability (T$_m$=57.7° C.) and 14-fold higher PET degradation activity at 40° C. compared to wild type IsPETase (Son, Hyeoncheol Francis et al., 2019. "Rational Protein Engineering of Thermo-Stable PETase from *Ideonella* Sakaiensis for Highly Efficient PET Degradation." ACS Catalysis 9(4): 3519-26. https://doi.org/10.1021/acscatal.9b00568). More recently, Cui et al reported a computationally designed/sPETase$^{L117F/Q119Y/T140D/W159H,G165A/I168R/A180I/S188Q/}$ $^{S214H/R280A}$ that possess a drastically improved thermal tolerance (T$_m$=79.8° C.) and an over two orders of magnitude enhancement in PET degradation activity (Cui, Ying-Lu et al., 2019. Computational Redesign of PETase for Plastic Biodegradation by GRAPE Strategy. https://doi.org/10.1101/787069).

BRIEF SUMMARY OF THE INVENTION

In some embodiments, the disclosure provides engineered PET (poly(ethylene terephthalate)) hydrolases comprising an amino acid sequence substantially (e.g., at least 70, 75, 80, 85, 90, 95, 98, 99%) identical to SEQ ID NO: 1 and having at least one mutation corresponding to a position relative to SEQ ID NO: 1 selected from the group consisting of N233, S58, N114, S121, N225, M262, T270, T140, S61, 1208, and R224. In some embodiments, the at least one mutation is selected from the group consisting of N233K, S58E, S58A, N114T, S121E, N225C, M262L, T270V, T140D, S61T, I208V, and R224Q. In some embodiments, the at least one mutation is selected from the group consisting of S58Y, S58M, S58L, S58V, S58P, S61D, S61E, S61Y, S61F, N114H, N114L, N114R, N114S, N114T, S121E, T140Y, T140L, T140I, T140V, T140S, I208M, I208H, I208F, I208Y, I208P, I208A, R224D, R224E, R224S, R224T, R224N, R224Q, N225N, N225I, N225V, N225M, N225A, N225L, N225S, N225T, N233R, N233Y, N233H, N233P, M262L, M262I, M262A, M262V, M262F, M262W, T270Y, T270R, T270H, R43K, A240C, and H186D. In some embodiments, the amino acid sequence is at least 95%, 98% or 99% identical to SEQ ID NO: 1, 2 or 3. In some embodiments, the amino acid sequence is identical to SEQ ID NO: 1, 2 or 3 except for the at least one mutation. In some embodiments, the amino acid sequence is at least 95%, 98%, 99% or 100% identical to one or more of SEQ ID NOS: 6-34.

In some embodiments, the amino acid sequence has at least two mutations corresponding to a position relative to SEQ ID NO: 1 selected from the group consisting of N233K, S58E, S58A, N114T, S121E, N225C, M262L, T270V, T140D, S61T, 1208V, and R224Q. In some embodiments, the amino acid sequence has two or three (or 4, 5, 6, 7, 8, 9, or 10) mutations corresponding to a position relative to SEQ ID NO: 1 selected from the group consisting of N233K, S58E, S58A, N114T, N225C, M262L, T270V, T140D, S61T, 1208V, R224Q, S58Y, S58M, S58L, S58V, S58P, S61D, S61E, S61Y, S61F, N114H, N114L, N114R, N114S, N114T, S121E, T140Y, T140L, T140I, T140V, T140S, I208M, I208H, I208F, I208Y, I208P, I208A, R224D, R224E, R224S, R224T, R224N, R224Q, N225N, N225I, N225V, N225M, N225A, N225L, N225S, N225T, N233R, N233Y, N233H, N233P, M262L, M262I, M262A, M262V, M262F, M262W, T270Y, T270R, T270H, R43K, A240C, and H186D.

Also provides is a polynucleotide encoding the engineered PET hydrolase as described above or elsewhere herein. In some embodiments, the engineered PET hydrolase further comprises a signal peptide.

Also provided is a vector comprising a promoter operably linked to the polynucleotide as described above or elsewhere herein such that the promoter controls expression of the engineered PET hydrolase.

Also provides is a host cell comprising the polynucleotide or the vector as described above or elsewhere herein. In some embodiments, the host cell is a microbial cell. In some embodiments, the host cell is a bacterial cell. In some embodiments, the bacterial cell is *Pseudomonas putida*. In some embodiments, the host cell is a fungal cell.

Also provided are methods of degrading poly(ethylene terephthalate) (PET) comprising contacting PET with the engineered PET hydrolase as described above or elsewhere herein under conditions to degrade the PET. In some embodiments, the method comprises contacting the PET with a host cell that expresses and secretes the engineered PET hydrolase. In some embodiments, the engineered PET hydrolase is purified.

In some embodiments, the conditions include an incubation at a temperature of between 25-70° C. In some embodiments, the temperature is 25-40° C. or 30-40° C. or 25-45° C. In some embodiments, the temperature is 40-70° C. or 45-65° C. or 45-55° C.

In some embodiments, the conditions include an incubation at a pH of 6-10 (e.g., 6-8, 7-8.5, or 8-10).

Definitions

A "PET hydrolase" is from an esterase class of enzymes that catalyze the hydrolysis of polyethylene terephthalate (PET) plastic to monomeric mono-2-hydroxyethyl terephthalate (MHET). An example of a PET hydrolase is SEQ ID NO:1, which is the wild-type *Ideonella* sakaiensis "IsPETase." PET hydrolase activity can be determined by measuring the ability of an enzyme to degrade PET film, measured by the change of weight of the film following incubation with the enzyme under set conditions for a set time period. See, e.g., Example 7

A "polynucleotide" is a single- or double-stranded polymer of deoxyribonucleotide or ribonucleotide bases typically read from the 5' to the 3' end. Polynucleotides include RNA and DNA, and may be isolated from natural sources, synthesized in vitro, or prepared from a combination of natural and synthetic molecules. When the term is applied to double-stranded molecules it is used to denote overall length and will be understood to be equivalent to the term "base pairs".

A "polypeptide" or "protein" is a polymer of amino acid residues joined by peptide bonds, whether produced naturally or synthetically.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, California, USA).

The phrase "substantial identity" or "substantially identical," used in the context of two nucleic acids or polypeptides, refers to a sequence that has at least 70% sequence identity with a reference sequence. Alternatively, percent identity can be any integer from 70% to 100%. In some embodiments, a sequence is substantially identical to a reference sequence if the sequence has at least 70%, 75%, 80%, 85%, 90%, 91%, 92%, 93%, 94%, 95%, 96%, 97%, 98%, or 99% sequence identity to the reference sequence as determined using the methods described herein; preferably BLAST using standard parameters, as described below. Embodiments of the present disclosure provide for polypeptides that are substantially identical to any one or more of SEQ ID NO: 1-3 and that contain at least one amino acid substitution as described herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Algorithms that are suitable for determining percent sequence identity and sequence similarity are the BLAST and BLAST 2.0 algorithms, which are described in Altschul et al. (1990) *J. Mol. Biol.* 215:403-410 and Altschul et al.

(1977) *Nucleic Acids Res.* 25:3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

An "amino acid mutation" refers to replacing the amino acid residue in a given position (e.g., the naturally occurring amino acid residue that occurs in a wild-type PET hydrolase or other non-natural PET hydrolase) with another amino acid residue (for example, other than the naturally-occurring residue). For example, the naturally occurring amino acid residue at position 233 of the wild-type *Ideonella* sakaiensis IsPETase wild type sequence (SEQ ID NO: 1) is asparagine (N) (N233); accordingly, an amino acid substitution at N233 refers to replacing the naturally occurring asparagine with any amino acid residue other than asparagine.

Individual substitutions to a polypeptide sequence that alters a single amino acid or a small percentage of amino acids in the encoded sequence results in a "conservatively modified variant" where the alteration results in the substitution of an amino acid with a chemically similar amino acid. The following amino acids are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine(S), Threonine (T); and 8) Cysteine (C), Methionine (M) (see, e.g., Creighton, Proteins (1984)).

An amino acid residue "corresponding to an amino acid residue [X] in [specified sequence]," or an amino acid substitution "corresponding to an amino acid substitution [X] in [specified sequence]" and similar refers to an amino acid in a polypeptide of interest that aligns with the equivalent amino acid of a specified sequence when the polypeptide and the sequence are optimally aligned. For example, the amino acid corresponding to a position of SEQ ID NO: 1 can be determined using an alignment algorithm such as BLAST. In some embodiments, "correspondence" of amino acid positions is determined by aligning SEQ ID NO: 1 to another PET hydrolase sequence. When a test PET hydrolase sequence differs from SEQ ID NO:1 (e.g., by changes in amino acids or addition or deletion of amino acids), it may be that a particular mutation associated with improved PET hydrolase activity will not be in the same numerical position number as it is in SEQ ID NO: 1, for example if the test PET hydrolase had an amino terminal signal sequence or one or more amino acid inserted relative to SEQ ID NO: 1 but the position will still "correspond" with the position in SEQ ID NO: 1 as determined by alignment.

The term "host cell" refers to any cell capable of replicating and/or transcribing and/or translating a heterologous polynucleotide. Thus, a "host cell" refers to any prokaryotic cell (including but not limited to E. coli) or eukaryotic cell (including but not limited to yeast cells, mammalian cells, avian cells, amphibian cells, plant cells, fish cells, and insect cells), whether located in vitro or in vivo. For example, host cells may be located in a transgenic animal or transgenic plant. Host cells can be for example, transformed with heterologous polynucleotide.

A "vector" refers to a nucleic acid that includes a coding sequence and sequences necessary for expression of the coding sequence. The vector can be viral or non-viral. A "plasmid" is a non-viral vector, e.g., a nucleic acid molecule that encodes for genes and/or regulatory elements necessary for the expression of genes. A "viral vector" is a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

BRIEF DESCRIPTION OF THE DRAWINGS

FIG. 8 is an alignment of the amino acid sequences of WT NET (SEQ ID NO: 5) comprising ten selected substitutions predicted by Neural Network modelling based on the crystallographic structures of the WT IsPETase, and Thermo NET (SEQ ID NO: 5) comprising six selected substitutions predicted by Neural Network modelling based on the crystallographic structures of the ThermoPETase, as compared to the wildtype IsPETase (SEQ ID NO: 1). Modifications in the mutant sequences are highlighted. Figure discloses SEQ ID NOS 1, 5, and 35, respectively, in order of appearance.

FIG. 9*a-c*: Machine-learning guided predictions conferred improved enzyme performance for various PETase scaffolds. 9a. Wild-type PETase protein structure rendered by the output of Mutcompute. Each amino acid residue of PETase was assessed by Mutcompute, resulting in a probability distribution that reflects the chemical congruency of each of the twenty amino acid with the neighboring chemical microenvironments. Residues assigned the low wildtype probability (disfavored) are red, whereas the residues assigned the high wildtype probability (favored) are blue. Interactive visualizations of MutCompute for both crystal structures utilized in this study are publicly available at https://www.mutcompute.com/petase/5xjh and https://www.mutcompute.com/petase/6ij6. 9b. Microenvironment of the four major mutations predicted by Mutcompute. 9c. Schematic of the down-selection of mutations predicted by Mutcompute and comparison of the enzymatic performance of variants created through mutagenesis with the down-selected mutations. Through running MutCompute with the crystal structure of both wild-type PETase and Thermo-PETase, two libraries of predictions were generated. The predictions were then ranked by the fold change in the probabilities between the predicted and the wild-type amino acid. Using a stepwise combination strategy, 159 variants were generated by incorporating single or multiple predicted mutations into various PETase scaffolds. Through experimental characterization of the variants, four major mutations were down selected and combinatorially assembled across three PETase scaffolds: wild-type PETase (WT), Thermo-PETase (Thermo), and DuraPETase (Dura) to create all possible combinations. The heatmaps show the PET-hydrolytic activity of the resulting variants and the fold-change of activity over the variants' respective scaffolds. PET-hydrolytic activity was evaluated by measuring the amount of PET monomers (the sum of TPA and MHET) released from hydrolyzing gf-PET film by the PETase variants after 96 hrs of reaction time. $KH_2PO_4$—NaOH (pH8) buffer was used for all enzymes shown in this figure. All measurements were conducted in triplicate (n=3).

FIG. 14|Mass, crystallinity %, and time for complete degradation of various pc-PET films by αPETase. The circular pc-PET films (6 mm in diameter) were hole-punched from 51 different postconsumer plastic products used in the packaging of food, beverages, medications, office supplies, household goods and cosmetics available at local grocery store chains (Walmart, Costco, and HEB). The pc-PET films were hydrolysed by serial treatment with αPETase at 50° C. until the films were completed degraded. The enzyme solution (200 nM of αPETase in 100 mM KH$_2$PO$_4$—NaOH (pH8) buffer) was replenished every 24 hours. The crystallinity % of the intact pc-PET films was determined by differential scanning calorimetry. The initial mass of the films was determined gravimetrically by a digital scale. Both DSC and gravimetric measurements were conducted in triplicate. Means±s.d. (n=3) are shown.

DETAILED DESCRIPTION OF THE INVENTION

Figure 1:
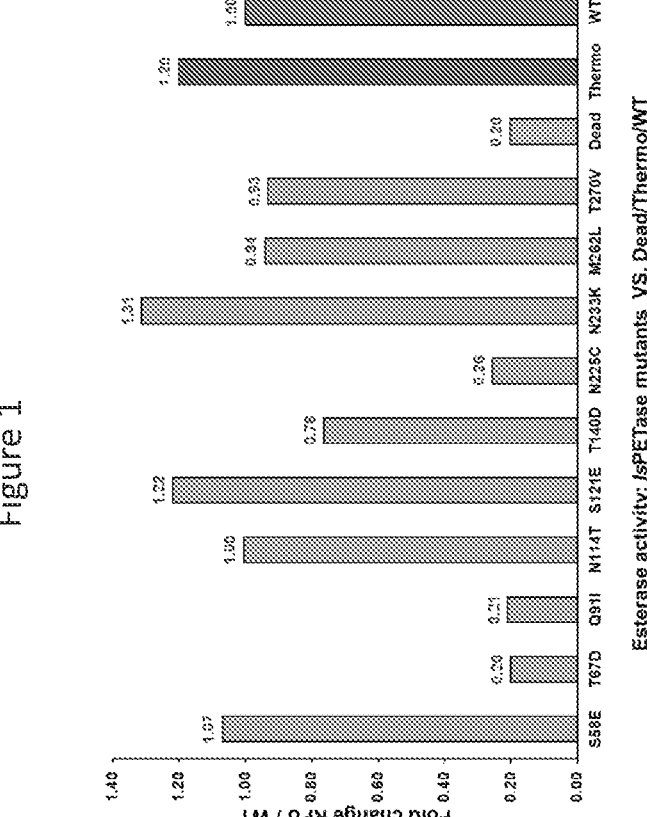
FIG. 1 is a bar graph showing the esterase activity of IsPETase variants containing a series of mutations predicted by the neural network analysis, a disabled IsPETase, and ThermoPETase, as compared to the wild type IsPETase. The esterase activities of the wild type IsPETase and its variants are measured by the resorufin butyrate assay. "Thermo" stands for the ThermoPETase that contains mutations S121E, D186H and R280A; "Dead" stands for a disabled IsPETase that has been mutated (S160A) to lose its enzymatic function; "WT" stands for the wild type IsPETase. All samples are purified protein samples and normalized to protein concentration.

The present disclosure provides mutant forms of PET hydrolase (i.e., PETase) enzymes that exhibit enhanced enzymatic activity as compared to wildtype enzyme. Mutant forms of IsPETase described herein can maintain catalytic activity across a wider range of temperatures, e.g., lower temperature than a wild type enzyme, as well as improved activity across a wider pH range.

For example, it has been discovered that single substitution of amino acid residues N233, S58, N114, N225, M262, T270, or T140 in the *Ideonella* sakaiensis IsPETase wild type sequence (shown in SEQ ID NO: 1) with Lysine (N233K), Glutamic acid (S58E), Threonine (N114T), Cysteine (N225C), Leucine (M262L), Valine (T270V), or Aspartic acid (T140D), leads to increased PET degradation activity as compared to the wild type enzyme. Among these single mutants, IsPETase variant that contains mutation N233K exhibits the greatest improvement, which showed an approximately 8.5-fold higher PET degradation activity than the wild type IsPETase at 40° C. in a PET film degradation assay.

Moreover, it has also been found that the substitution of amino acid residue N233 in the sequences of two published IsPETase variants (Cui, Ying-Lu et al., 2019. Computational Redesign of PETase for Plastic Biodegradation by GRAPE Strategy. https://doi.org/10.1101/787069; Son, Hyeoncheol Francis et al., 2019. "Rational Protein Engineering of Thermo-Stable PETase from *Ideonella* Sakaiensis for Highly Efficient PET Degradation." ACS Catalysis 9 (4): 3519-26. https://doi.org/10.1021/acscatal.9b00568)-IsPETase$^{S121E/D186H/R280A}$ (referred to herein as "Thermo-PETase" and IsPETase$^{L117F/Q119Y/T140D/W159H, G165A/I168R/A180I/S188Q/S214H/R280A}$ (referred to herein as "DuraPETase") with Lysine (N233K), results in higher thermal stability and increased PET degradation activity as compared to Thermo-PETase and DuraPETase. The amino acid sequences of ThermoPETase and DuraPETase are shown in SEQ ID NO: 2 and SEQ ID NO: 3 respectively. More specifically, the ThermoPETase variant containing the amino acid substitution of N233K (denoted as "TNK" and its sequence is shown in SEQ ID NO: 4), exhibits approximately 6.4-fold higher PET degradation activity than the ThermoPETase at 50° C.

In addition, it has also been discovered that single substitution of amino acid residues S58, N114, N225, M262, T270, S61, I208, or R224 in the IsPETase variant—TNK sequence (shown in SEQ ID NO: 4) with Glutamic acid (S58E) or Alanine (S58A), Threonine (N114T), Cysteine (N225C), Leucine (M262L), Valine (T270V), Threonine (S61T), Valine (I208V) or Glutamine (R224Q), leads to further increased PET degradation activity and thermal stability as compared to TNK enzyme. Specifically, the TNK variant containing the amino acid substitution of R224Q exhibits higher PET degradation activity than TNK at temperatures 30, 40, 50 and 55° C.

The disclosure provides engineered (i.e., non-natural) PET (poly(ethylene terephthalate)) hydrolases having certain amino acid changes compared to a control PET hydrolase such that the engineered PET hydrolase has improved thermostability, improved activity at certain temperatures or pHs, or a combination thereof, compared to the control PET hydrolase. The control PET hydrolase will be a PET hydrolase lacking the recited mutations but otherwise identical, and typically will be the PET hydrolase into which the mutations are introduced.

As discussed in the examples, the mutations have been inserted into several different PET hydrolases, generally with improvement in activity shown in each case. Accordingly, the disclosure provides for introduction of one or more of the mutations into an amino acid sequence substantially identical (e.g., at least 70, 80, 90, or 95%) identical to SEQ ID NO:1 or SEQ ID NO:2 or SEQ ID NO: 3 and having at least one mutation corresponding to a position relative to SEQ ID NO: 1 selected from the group consisting of N233, S58, N114, S121, N225, M262, T270, T140, S61, I208, and R224. In some embodiments, at least one mutation is selected from the group consisting of N233K, S58E, S58A, N114T, S121E, N225C, M262L, T270V, T140D, S61T, I208V, and R224Q. In some embodiments, at least one mutation is selected from the group of S58Y/M/L/V/P, S61D/E/Y/F, N114H/L/R/S/T, T140Y/L/I/V/S, I208M/H/F/Y/P/A, R224D/E/S/T/N/Q, N225N/I/V/M/A/L/S/T, N233R/Y/H/P, M262L/I/A/V/F/W, and T270Y/R/H.

In some embodiments, the PET hydrolase can have 2, 3, 4, 5, 6, 7, or more of the above-described mutations. Exemplary combinations of mutations that are specifically disclosed include those described in Table 2, which can be introduced, for example into an amino acid sequence substantially identical (e.g., at least 70, 80, 90, or 95%) to SEQ ID NO: 1 or SEQ ID NO:2 or SEQ ID NO: 3. For example in some embodiments, the PET hydrolase comprises an N233 substitution (for example but not limited to N233K) and at least one further substitution at S58, N114, N225, M262, T270, S61, I208, R224, R43, A240, and H186 (for example but not limited to one of S58E, S58A, N114T, N225C, M262L, T270V, T140D, S61T, I208V, R224Q, R43K, A240C, or H186D). For example, in some embodiments, the PET hydrolase comprises an N233 substitution (for example but not limited to N233K) and an R224 substitution (for example but not limited to R224Q). In some embodiments, any of the above-listed substitutions can be combined with one, two or all three of S121E/D186H/R280A.

Exemplary mutants, which can be included for example in an amino acid sequence that is at least 95%, 98%, 99% or otherwise 100% identical to SEQ ID NO:1, 2, or 3, can include but are not limited to: N233K (e.g., in SEQ ID NO:1), S121E (e.g., in SEQ ID NO:1), T140D (e.g., in SEQ ID NO: 1), R224Q (e.g., in SEQ ID NO:1), N233K+S121E (e.g., in SEQ ID NO:1), N233K+R224Q (e.g., in SEQ ID NO:1), R224Q+S121E (e.g., in SEQ ID NO:1), N233K+T140D (e.g., in SEQ ID NO:1), R224Q+T140D (e.g., in SEQ ID NO:1), S121E+T140D (e.g., in SEQ ID NO:1), N233K+R224Q+S121E (e.g., in SEQ ID NO:1), N233K+R224Q+T140D (e.g., in SEQ ID NO:1), N233K+S121E+T140D (e.g., in SEQ ID NO:1), R224Q+S121E+T140D (e.g., in SEQ ID NO:1), N233K+R224Q+S121E+T140D (e.g., in SEQ ID NO:1), N233K (e.g., in SEQ ID NO:2), T140D (e.g., in SEQ ID NO:2), R224Q (e.g., in SEQ ID NO:2), N233K+T140D (e.g., in SEQ ID NO:2), N233K+R224Q (e.g., in SEQ ID NO:1 or 2), R224Q+T140D (e.g., in SEQ ID NO:2), N233K+R224Q+T140D (e.g., in SEQ ID NO:2), N233K (e.g., in SEQ ID NO:3), S121E (e.g., in SEQ ID NO:3), R224Q (e.g., in SEQ ID NO:3), N233K+R224Q (e.g., in SEQ ID NO:3), N233K+S121E (e.g., in SEQ ID NO:3), R224Q+S121E (e.g., in SEQ ID NO:3, or R224Q+S121E+N233K (e.g., in SEQ ID NO:3).

Exemplary sequences include but are not limited to SEQ ID NOS: 6-34 as follows:

---

Mutants built upon the WT PETase scaffold (SEQ ID NO: 1)

WT_N233K (SEQ ID NO: 6)

```
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPSSRSSQQMAALRQVASLNGTSSSPIYGKVDTAR
MGVMGWSMGGGGSLISAANNPSLKAAAPQAPWDSSTNFSSVTVPTLIFACENDSIAPVNSSA
LPIYDSMSRNAKQFLEIKGGSHSCANSGNSNQALIGKKGVAWMKRFMDNDTRYSTFACENP
NSTRVSDFRTANCS
```

WT_S121E (SEQ ID NO: 7)

```
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGTSSSPIYGKVDTAR
MGVMGWSMGGGGSLISAANNPSLKAAAPQAPWDSSTNFSSVTVPTLIFACENDSIAPVNSSA
LPIYDSMSRNAKQFLEINGGSHSCANSGNSNQALIGKKGVAWMKRFMDNDTRYSTFACENP
NSTRVSDFRTANCS
```

WT_T140D (SEQ ID NO: 8)

```
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPSSRSSQQMAALRQVASLNGDSSSPIYGKVDTAR
MGVMGWSMGGGGSLISAANNPSLKAAAPQAPWDSSTNFSSVTVPTLIFACENDSIAPVNSSA
LPIYDSMSRNAKQFLEINGGSHSCANSGNSNQALIGKKGVAWMKRFMDNDTRYSTFACENP
NSTRVSDFRTANCS
```

WT+R224Q (SEQ ID NO: 9)

```
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPSSRSSQQMAALRQVASLNGTSSSPIYGKVDTAR
MGVMGWSMGGGGSLISAANNPSLKAAAPQAPWDSSTNFSSVTVPTLIFACENDSIAPVNSSA
LPIYDSMSQNAKQFLEINGGSHSCANSGNSNQALIGKKGVAWMKRFMDNDTRYSTFACENP
NSTRVSDFRTANCS
```

WT_N233K+S121E (SEQ ID NO: 10)

```
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGTSSSPIYGKVDTAR
MGVMGWSMGGGGSLISAANNPSLKAAAPQAPWDSSTNFSSVTVPTLIFACENDSIAPVNSSA
LPIYDSMSRNAKQFLEIKGGSHSCANSGNSNQALIGKKGVAWMKRFMDNDTRYSTFACENP
NSTRVSDFRANCS
```

WT_N233K+R224Q (SEQ ID NO: 11)

```
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPSSRSSQQMAALRQVASLNGTSSSPIYGKVDTAR
MGVMGWSMGGGGSLISAANNPSLKAAAPQAPWDSSTNFSSVTVPTLIFACENDSIAPVNSSA
LPIYDSMSQNAKQFLEIKGGSHSCANSGNSNQALIGKKGVAWMKRFMDNDTRYSTFACENP
NSTRVSDFRTANCS
```

WT_R224Q+S121E (SEQ ID NO: 12)

```
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGTSSSPIYGKVDTAR
MGVMGWSMGGGGSLISAANNPSLKAAAPQAPWDSSTNFSSVTVPTLIFACENDSIAPVNSSA
LPIYDSMSQNAKQFLEINGGSHSCANSGNSNQALIGKKGVAWMKRFMDNDTRYSTFACENP
NSTRVSDFRTANCS
```

WT_N233K+T140D (SEQ ID NO: 13)

```
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPSSRSSQQMAALRQVASLNGDSSSPIYGKVDTAR
MGVMGWSMGGGGSLISAANNPSLKAAAPQAPWDSSTNFSSVTVPTLIFACENDSIAPVNSSA
LPIYDSMSRNAKQFLEIKGGSHSCANSGNSNQALIGKKGVAWMKRFMDNDTRYSTFACENP
NSTRVSDFRTANCS
```

WT_R224Q+T140D (SEQ ID NO: 14)

```
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPSSRSSQQMAALRQVASLNGDSSSPIYGKVDTAR
MGVMGWSMGGGGSLISAANNPSLKAAAPQAPWDSSTNFSSVTVPTLIFACENDSIAPVNSSA
LPIYDSMSQNAKQFLEINGGSHSCANSGNSNQALIGKKGVAWMKRFMDNDTRYSTFACENP
NSTRVSDFRTANCS
```

-continued

WT_S121E+T140D (SEQ ID NO: 15)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGTSSSPIYGKVDTAR
MGVMGWSMGGGGSLISAANNPSLKAAAPQAPWDSSTNFSSVTVPTLIFACENDSIAPVNSSA
LPIYDSMSRNAKQFLEINGGSHSCANSGNSNQALIGKKGVAWMKRFMDNDTRYSTFACENP
NSTRVSDFRTANCS

WT_N233K+R224Q+S121E (SEQ ID NO: 16)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGTSSSPIYGKVDTAR
MGVMGWSMGGGGSLISAANNPSLKAAAPQAPWDSSTNFSSVTVPTLIFACENDSIAPVNSSA
LPIYDSMSQNAKQFLEIKGGSHSCANSGNSNQALIGKKGVAWMKRFMDNDTRYSTFACENP
NSTRVSDFRTANCS

WT_N233K+R224Q+T140D (SEQ ID NO: 17)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPSSRSSQQMAALRQVASLNGDSSSPIYGKVDTAR
MGVMGWSMGGGGSLISAANNPSLKAAAPQAPWDSSTNFSSVTVPTLIFACENDSIAPVNSSA
LPIYDSMSQNAKQFLEIKGGSHSCANSGNSNQALIGKKGVAWMKRFMDNDTRYSTFACENP
NSTRVSDFRTANCS

WT_N233K+S121E+T140D (SEQ ID NO: 18)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGDSSSPIYGKVDTAR
MGVMGWSMGGGGSLISAANNPSLKAAAPQAPWDSSTNFSSVTVPTLIFACENDSIAPVNSSA
LPIYDSMSRNAKQFLEIKGGSHSCANSGNSNQALIGKKGVAWMKRFMDNDTRYSTFACENP
NSTRVSDFRTANCS

WT_R224Q+S121E+T140D (SEQ ID NO: 19)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGDSSSPIYGKVDTAR
MGVMGWSMGGGGSLISAANNPSLKAAAPQAPWDSSTNFSSVTVPTLIFACENDSIAPVNSSA
LPIYDSMSQNAKQFLEINGGSHSCANSGNSNQALIGKKGVAWMKRFMDNDTRYSTFACENP
NSTRVSDFRTANCS

WT N233K+R224Q+S121E+T140D (SEQ ID NO: 20)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGDSSSPIYGKVDTAR
MGVMGWSMGGGGSLISAANNPSLKAAAPQAPWDSSTNFSSVTVPTLIFACENDSIAPVNSSA
LPIYDSMSQNAKQFLEIKGGSHSCANSGNSNQALIGKKGVAWMKRFMDNDTRYSTFACENP
NSTRVSDFRTANCS

Mutants built upon the ThermoPETase scaffold (SEQ ID NO: 2)

Thermo_N233K (SEQ ID NO: 21)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGTSSSPIYGKVDTAR
MGVMGWSMGGGGSLISAANNPSLKAAAPQAPWHSSTNFSSVTVPTLIFACENDSIAPVNSSA
LPIYDSMSRNAKQFLEIKGGSHSCANSGNSNQALIGKKGVAWMKRFMDNDTRYSTFACENP
NSTAVSDFRTANCS Thermo_T140D (SEQ ID NO: 22)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGDSSSPIYGKVDTAR
MGVMGWSMGGGGSLISAANNPSLKAAAPQAPWHSSTNFSSVTVPTLIFACENDSIAPVNSSA
LPIYDSMSRNAKQFLEINGGSHSCANSGNSNQALIGKKGVAWMKRFMDNDTRYSTFACENP
NSTAVSDFRTANCS Thermo_R224Q (SEQ ID NO: 23)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGTSSSPIYGKVDTAR
MGVMGWSMGGGGSLISAANNPSLKAAAPQAPWHSSTNFSSVTVPTLIFACENDSIAPVNSSA
LPIYDSMSQNAKQFLEINGGSHSCANSGNSNQALIGKKGVAWMKRFMDNDTRYSTFACENP
NSTAVSDFRTANCS Thermo_N233K+T140D (SEQ ID NO: 24)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGDSSSPIYGKVDTAR

```
MGVMGWSMGGGGSLISAANNPSLKAAAPQAPWHSSTNFSSVTVPTLIFACENDSIAPVNSSA
LPIYDSMSRNAKQFLEIKGGSHSCANSGNSNQALIGKKGVAWMKRFMDNDTRYSTFACENP
NSTAVSDFRTANCS

Thermo_N233K+R224Q
                                                  (SEQ ID NO: 25)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGTSSSPIYGKVDTAR
MGVMGWSMGGGGSLISAANNPSLKAAAPQAPWHSSTNFSSVTVPTLIFACENDSIAPVNSSA
LPIYDSMSQNAKQFLEIKGGSHSCANSGNSNQALIGKKGVAWMKRFMDNDTRYSTFACENP
NSTAVSDFRTANCS Thermo_R224Q+T140D
                                                  (SEQ ID NO: 26)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGDSSSPIYGKVDTAR
MGVMGWSMGGGGSLISAANNPSLKAAAPQAPWHSSTNFSSVTVPTLIFACENDSIAPVNSSA
LPIYDSMSQNAKQFLEINGGSHSCANSGNSNQALIGKKGVAWMKRFMDNDTRYSTFACENP
NSTAVSDFRTANCS Thermo_N233K+R224Q+T140D
                                                  (SEQ ID NO: 27)
QTNPYARGPNPTAASLEASAGPFTVRSFTVSRPSGYGAGTVYYPTNAGGTVGAIAIVPGYTAR
QSSIKWWGPRLASHGFVVITIDTNSTLDQPESRSSQQMAALRQVASLNGDSSSPIYGKVDTAR
MGVMGWSMGGGGSLISAANNPSLKAAAPQAPWHSSTNFSSVTVPTLIFACENDSIAPVNSSA
LPIYDSMSQNAKQFLEIKGGSHSCANSGNSNQALIGKKGVAWMKRFMDNDTRYSTFACENP
NSTAVSDFRTANCS Mutants built upon the DuraPETase scaffold (SEQ ID NO: 3)

Dura_N233K (βPETase)
                                                  (SEQ ID NO: 28)
QTNPYARGPNPTAASLEASAGPFTVRSFTVSRPSGYGAGTVYYPTNAGGTVGAIAIVPGYTAR
QSSIKWWGPRLASHGFVVITIDTNSTFDYPSSRSSQQMAALRQVASLNGDSSSPIYGKVDTAR
MGVMGHSMGGGASLRSAANNPSLKAAIPQAPWDSQTNFSSVTVPTLIFACENDSIAPVNSHA
LPIYDSMSRNAKQFLEIKGGSHSCANSGNSNQALIGKKGVAWMKRFMDNDTRYSTFACENP
NSTAVSDFRTANCS Dura_S121E
                                                  (SEQ ID NO: 29)
QTNPYARGPNPTAASLEASAGPFTVRSFTVSRPSGYGAGTVYYPTNAGGTVGAIAIVPGYTAR
QSSIKWWGPRLASHGFVVITIDTNSTFDYPESRSSQQMAALRQVASLNGDSSSPIYGKVDTAR
MGVMGHSMGGGASLRSAANNPSLKAAIPQAPWDSQTNFSSVTVPTLIFACENDSIAPVNSHA
LPIYDSMSRNAKQFLEINGGSHSCANSGNSNQALIGKKGVAWMKRFMDNDTRYSTFACENP
NSTAVSDFRTANCS Dura_R224Q
                                                  (SEQ ID NO: 30)
QTNPYARGPNPTAASLEASAGPFTVRSFTVSRPSGYGAGTVYYPTNAGGTVGAIAIVPGYTAR
QSSIKWWGPRLASHGFVVITIDTNSTFDYPSSRSSQQMAALRQVASLNGDSSSPIYGKVDTAR
MGVMGHSMGGGASLRSAANNPSLKAAIPQAPWDSQTNFSSVTVPTLIFACENDSIAPVNSHA
LPIYDSMSQNAKQFLEINGGSHSCANSGNSNQALIGKKGVAWMKRFMDNDTRYSTFACENP
NSTAVSDFRTANCS Dura_N233K+R224Q
                                                  (SEQ ID NO: 31)
QTNPYARGPNPTAASLEASAGPFTVRSFTVSRPSGYGAGTVYYPTNAGGTVGAIAIVPGYTAR
QSSIKWWGPRLASHGFVVITIDTNSTFDYPSSRSSQQMAALRQVASLNGDSSSPIYGKVDTAR
MGVMGHSMGGGASLRSAANNPSLKAAIPQAPWDSQTNFSSVTVPTLIFACENDSIAPVNSHA
LPIYDSMSQNAKQFLEIKGGSHSCANSGNSNQALIGKKGVAWMKRFMDNDTRYSTFACENP
NSTAVSDFRTANCS Dura_N233K+S121E
                                                  (SEQ ID NO: 32)
QTNPYARGPNPTAASLEASAGPFTVRSFTVSRPSGYGAGTVYYPTNAGGTVGAIAIVPGYTAR
QSSIKWWGPRLASHGFVVITIDTNSTFDYPESRSSQQMAALRQVASLNGDSSSPIYGKVDTAR
MGVMGHSMGGGASLRSAANNPSLKAAIPQAPWDSQTNFSSVTVPTLIFACENDSIAPVNSHA
LPIYDSMSRNAKQFLEIKGGSHSCANSGNSNQALIGKKGVAWMKRFMDNDTRYSTFACENP
NSTAVSDFRTANCS Dura_R224Q+S121E
                                                  (SEQ ID NO: 33)
QTNPYARGPNPTAASLEASAGPFTVRSFTVSRPSGYGAGTVYYPTNAGGTVGAIAIVPGYTAR
QSSIKWWGPRLASHGFVVITIDTNSTFDYPESRSSQQMAALRQVASLNGDSSSPIYGKVDTAR
MGVMGHSMGGGASLRSAANNPSLKAAIPQAPWDSQTNFSSVTVPTLIFACENDSIAPVNSHA
LPIYDSMSQNAKQFLEINGGSHSCANSGNSNQALIGKKGVAWMKRFMDNDTRYSTFACENP
NSTAVSDFRTANCS
```

-continued

```
Dura_R224Q+S121E+N233K
                                                            (SEQ ID NO: 34)
QTNPYARGPNPTAASLEASAGPFTVRSFTVSRPSGYGAGTVYYPTNAGGTVGAIAIVPGYTAR
QSSIKWWGPRLASHGFVVITIDTNSTFDYPESRSSQQMAALRQVASLNGDSSSPIYGKVDTAR
MGVMGHSMGGGASLRSAANNPSLKAAIPQAPWDSQTNFSSVTVPTLIFACENDSIAPVNSHA
LPIYDSMSQNAKQFLEIKGGSHSCANSGNSNQALIGKKGVAWMKRFMDNDTRYSTFACENP
NSTAVSDFRTANCS
```

The disclosure also provides nucleic acids encoding the engineered PET hydrolases described herein, e.g., PET hydrolases comprising an amino acid sequence substantially identical (e.g., at least 70, 80, 90, or 95%) identical to SEQ ID NO:1 or SEQ ID NO:2 or SEQ ID NO:3 and having at least one mutation corresponding to a position relative to SEQ ID NO: 1 selected from the group consisting of N233, S58, N114, N225, M262, T270, T140, S61, I208, and R224. In some embodiments, the nucleic acids comprise a promoter operably linked to the coding sequence. The coding sequence can be codon optimized for the cell in which it will be expressed.

Nucleic acids encoding the polypeptides can be expressed using routine techniques in the field of recombinant genetics. Basic texts disclosing such techniques include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). Modifications of the polypeptides can additionally be made without diminishing biological activity. Some modifications may be made to facilitate the cloning, expression, or incorporation of a domain. The proteins described herein can be made using standard methods well known to those of skill in the art. Recombinant expression in a variety of host cells, including but not limited to prokaryotic cells such as E. coli, or other prokaryotic hosts are well known in the art.

Polynucleotides encoding the desired proteins in the complex, recombinant expression vectors, and host cells containing the recombinant expression vectors, as well as methods of making such vectors and host cells by recombinant methods are well known to those of skill in the art.

The polynucleotides may be synthesized or prepared by techniques well known in the art. Nucleotide sequences encoding the desired proteins may be synthesized, and/or cloned, and expressed according to techniques known to those of ordinary skill in the art. In some embodiments, the polynucleotide sequences will be codon optimized for a particular recipient using standard methodologies. For example, a DNA construct encoding a protein can be codon optimized for expression in microbial hosts, e.g., yeast or bacteria.

Examples of useful bacteria include, but are not limited to, *Escherichia, Enterobacter, Azotobacter, Erwinia, Bacillus, Pseudomonas, Klebsiella, Proteus, Salmonella, Serratia, Shigella, Rhizobia, Vitreoscilla*, and *Paracoccus*. The nucleic acid encoding the desired protein is operably linked to appropriate expression control sequences for each host. For *E. coli* this can include, for example, a promoter such as the T7, trp, or lambda promoters, a ribosome binding site and preferably a transcription termination signal. The proteins may also be expressed in other cells, such as mammalian, insect, plant, or yeast cells.

In some embodiments, the polypeptide construct contains one or more affinity tags, e.g., for the purposes of detection or purification. A number of suitable tags can be included in the polypeptide constructs including, for example, those described by Kimple et al. (Curr Protoc Protein Sci. 2013; 73(1): 9.9.1-9.9.23). Examples of affinity tags include, but are not limited to, a calmodulin binding peptide (CBP), a chitin binding domain (CBD), a dihyrofolate reductase (DHFR) moiety, a FLAG epitope, a glutathione S-transferase (GST) tag, a hemagglutinin (HA) tag; a maltose binding protein (MBP) moiety; a Myc epitope; a polyhistidine tag (e.g., HHHHHH (SEQ ID NO: 36)); and streptavidin-binding peptides (e.g., those described in U.S. Pat. No. 5,506, 121). An affinity tag may be included at one or more locations in the polypeptide construct. An affinity tag such as a streptavidin-binding peptide may reside, for example, at the N-terminus of the polypeptide construct or at the ('-terminus of the polypeptide construct. In some embodiments, the linker peptide comprises an affinity tag, e.g., a FLAG epitope containing the sequence DYKDDDDK (SEQ ID NO: 37) with or without additional amino acid residues.

The polypeptides described herein can be expressed intracellularly or can be secreted from the cell. In some embodiments a signal peptide is linked to the amino terminus of the expressed polypeptide such that the polypeptide is secreted from the cell.

Once expressed, the polypeptides can be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)). Substantially pure compositions of at least about 90 to 95% homogeneity (e.g., 98 to 99% or higher homogeneity) are provided in certain embodiments.

Also provided are reaction mixtures comprising a PET plastic disc and one or more engineered PET hydrolase as described herein as well as methods of using such reaction mixtures to demonstrate the degradation of the PET plastics as measured by a percentage mass loss of the disc after incubation with the enzyme. The engineered PET hydrolases in the reaction mixtures can be in purified form or can be expressed in a host cell (i.e., the host cell expressing the enzyme can be in the reaction mixture). Some advantages of the described PET hydrolases are that they can exhibit improved activity at elevated temperature while at the same time have the advantage of being able to degrade plastics at lower pH conditions and lower temperatures at a higher level of activity than previously described engineered or native PETases.

The time required for degrading a polyester containing material may vary depending on the polyester containing material itself (i.e., nature and origin of the plastic product, its composition, shape etc.), the precise enzyme and amount of enzyme used, as well as various process parameters (i.e., temperature, pH, additional agents, agitation etc.).

In some embodiments, the conditions of the degradation method include an ambient temperature, for example a temperature from 25-45° C. These temperatures can be especially useful in embodiments in which a host cell (e.g., a bacterial cell) expresses the PET hydrolase and the host cell is contacted to the PET plastic in the reaction mixture. The precise temperature for optimal survival and enzyme expression by the cell can be selected.

Alternatively, in some embodiments, the PET hydrolase is incubated with the PET plastic under higher temperatures, for example from 40-70° C. or 45-65° C. or 45-55° C.

In some embodiments, the temperature is maintained below the glass transition temperature (Tg) of the PET plastic in the material being degraded. In some embodiments, the temperature is maintained at or above the glass transition temperature (Tg) of the PET plastic in the material being degraded. In some embodiments, the process is implemented in a continuous way, at a temperature at which the enzyme can be used several times and/or recycled.

A variety of pHs can be used with the described enzymes. In some embodiments, the enzyme and PET plastic are reacted under a pH of 6-10 (e.g., 6-8, 7-8.5, or 8-10). A more neutral pH range can be of use for example where cells expressing the enzyme are incubated with the plastic.

In some embodiments, the plastic containing material may be pretreated prior to be contacted with the PET hydrolase, in order to physically change its structure, so as to increase the surface of contact between the plastic and the PET hydrolase.

Optionally, monomers and/or oligomers resulting from the depolymerization may be recovered, sequentially or continuously. A single type of monomers and/or oligomers or several different types of monomers and/or oligomers may be recovered, depending on the starting plastic containing material.

In some embodiments, one or more PET hydrolase as described herein is combined with a second enzyme (simultaneous or sequentially) to degrade a plastic product. For example in some embodiments, the second enzyme is a MHETase enzyme (see for example Palm et al., Nat Commun. 10:1717 (2019).

The recovered monomers and/or oligomers may be further purified, using all suitable purifying methods and conditioned in a re-polymerizable form. Examples of purifying methods include stripping process, separation by aqueous solution, steam selective condensation, filtration and concentration of the medium after the bioprocess, separation, distillation, vacuum evaporation, extraction, electrodialysis, adsorption, ion exchange, precipitation, crystallization, concentration and acid addition dehydration and precipitation, nanofiltration, acid catalyst treatment, semi continuous mode distillation or continuous mode distillation, solvent extraction, evaporative concentration, evaporative crystallization, liquid/liquid extraction, hydrogenation, azeotropic distillation process, adsorption, column chromatography, simple vacuum distillation and microfiltration, combined or not. Alternatively, the recovered/liberated monomers may be used by cells (either with or without explicit recovery) to be used as a carbon source for the production of a range products. This can be accomplished by co-incubation of the cells with the plastic and enzymes or in a sequential process. The following examples exemplify aspects of the invention and are not intended to limited it.

EXAMPLES

Example 1: Mutations Predicted by Neural Network Analysis

To further improve the thermal stability of IsPETase, we introduced a structure-based deep learning artificial intelligence (A.I.) model (Shroff, Raghav et al., 2019. "A Structure-Based Deep Learning Framework for Protein Engineering." BioRxiv, January, 833905. https://doi.org/10.1101/833905) for designing IsPETase variants with higher fitness. This 3D convolutional neural network A.I. model was trained to learn the correct association between amino acid residues and its surrounding chemical environment. It can identify disfavoured amino acid residues in a protein structure and predict the best substitution to improve the overall protein folding and function. Through the neural network analysis of IsPETase and PET film degradation assays, we have identified point mutations that can promote the PET degradation activity of IsPETase.

To improve the thermostability of the wild-type PETase, a 3D convolutional neural network A.I. model (Shroff et al. 2019) was applied for redesigning IsPETase variants with higher fitness. Initially, the neural network analysis was performed on the wild type IsPETase. Using the crystallographic structure of the wild type IsPETase deposited in RCSB Protein Data Bank (PDB: 6EQE, 5XG0, 5XJH), the disfavoured wild type amino acid residues are identified and suggested to be replaced by amino acids residues that might promote the overall fitness of the enzyme. As a result, ten amino acid substitutions, including N233K, S58E, N114T, N225C, M262L, T270V, or T140D, S121E, T67D, and Q91I were selected for mutagenesis of wild type IsPETase (Table 1). Subsequently, the neural network analysis was also performed on the ThermoPETase using its crystallographic structure deposited in RCSB Protein Data Bank (PDB: 61J6). As a result, 10 amino acid substitutions were predicted by the neural network model (Table 1). Excluding the overlapped mutations in these two sets of prediction and the mutations that have presented in the TNK enzyme, eleven amino acid substitutions, including S58E, N114T, N225C, M262L, T270V, T67D, Q91I, S121E, T67D, Q91I, S61T, I208V, S58A and R224Q were further selected for mutagenesis of the TNK enzyme.

Single or multiple neural net mutation(s) were introduced to different gene backgrounds (WT IsPETase, ThermoPETase, DuraPETase). Table 2 is the list of the mutants that have been created and characterized. The "√" mark indicates that the mutants of the specific mutation(s) in WT IsPETase, ThermoPETase, or DuraPETase background were created. The "+" mark highlights the mutants that showed improvement in PET degradation activity compared to their respective ancestral enzymes. Table 3 summarized all the mutants with improved PET degradation activity at various enzyme reaction temperatures. The "+" mark highlights the mutants that showed improvement in PET degradation activity compared to their respective ancestral enzymes at a specific temperature. In contrast, the "−" mark highlights the mutants that exhibited no improvement or deterioration in PET degradation activity compared to their respective ancestral enzymes at a specific temperature.

TABLE 1

| Predicted based on WT IsPETase | | | Predicted based on ThermoPETase | | |
|---|---|---|---|---|---|
| WT | Position | Mutated | WT | Position | Mutated |
| S | 121 | E | Q | 91 | I |
| M | 262 | L | N | 233 | K |
| T | 140 | D | N | 225 | C |
| N | 233 | K | S | 61 | T |
| S | 58 | E | I | 208 | V |
| T | 270 | V | S | 58 | A |

TABLE 1-continued

| Predicted based on WT IsPETase | | | Predicted based on ThermoPETase | | |
|---|---|---|---|---|---|
| WT | Position | Mutated | WT | Position | Mutated |
| N | 225 | C | R | 34 | L |
| Q | 91 | I | A | 240 | C |
| N | 114 | T | H | 186 | D |
| T | 67 | D | R | 224 | Q |

TABLE 2

| Mutation(s) | WT IsPETase | ThermoPETase | DuraPETase |
|---|---|---|---|
| S121E | ✓, + | | |
| M262L | ✓, + | | |
| T140D | ✓, + | | |
| N233K | ✓, + | ✓, + | ✓, + |
| S58E | ✓, + | | |
| T270V | ✓, + | | |
| N225C | ✓, + | | |
| Q91I | ✓ | | |
| N114T | ✓, + | | |
| T67D | ✓ | | |

TABLE 2-continued

| Mutation(s) | WT IsPETase | ThermoPETase | DuraPETase |
|---|---|---|---|
| N225C/N233K | ✓, + | ✓ | |
| M262L/N233K | ✓, + | ✓, + | |
| T270V/N233K | ✓, + | ✓, + | |
| T270V/M262L | ✓ | | |
| T270V/S58E | ✓, + | | |
| T270V/N114T | ✓, + | | |
| T270V/N225C | ✓, + | | |
| T270V/T140D | ✓, + | | |
| M262L/S58E | ✓, + | | |
| M262L/N114T | ✓, + | | |
| M262L/N225C | ✓, + | | |
| M262L/T140D | ✓, + | | |
| S58E/N114T | ✓ | | |
| S58E/N225C | ✓, + | | |
| S58E/T140D | ✓, + | | |
| N114T/N225C | ✓, + | | |
| N114T/T140D | ✓ | | |
| N225C/T140D | ✓, + | | |
| S61T/N233K | | ✓, + | |
| I208V/N233K | | ✓ | |
| S58A/N233K | | ✓, + | |
| A240C/N233K | | ✓ | |
| R224Q/N233K | | ✓, + | |
| N233K/T270V/M262L/S58E/N114T/N225C/T140D | ✓ | ✓ | ✓, + |

TABLE 3

| Mutation(s) | WT IsPETase | | | | ThermPETase | | | | DuraPETase | | | |
|---|---|---|---|---|---|---|---|---|---|---|---|---|
| | 30° C. | 40° C. | 50° C. | 55° C. | 30° C. | 40° C. | 50° C. | 55° C. | 30° C. | 40° C. | 50° C. | 55° C. |
| S121E | − | + | | | | | | | | | | |
| M262L | − | + | | | | | | | | | | |
| T140D | − | + | | | | | | | | | | |
| N233K | + | + | | | + | + | + | + | + | − | + | |
| S58E | + | + | | | | | | | | | | |
| T270V | + | + | | | | | | | | | | |
| N225C | − | + | | | | | | | | | | |
| N114T | − | + | | | | | | | | | | |
| S58E/N233K | + | − | − | | + | + | + | + | | | | |
| N114T/N233K | + | + | − | | + | + | + | + | | | | |
| T140D/N233K | + | + | − | | | | | | | | | |
| N225C/N233K | − | − | − | | + | − | + | − | | | | |
| M262L/N233K | + | + | − | | + | + | + | + | | | | |
| T270V/N233K | + | + | − | | + | + | − | − | | | | |
| T270V/S58E | + | − | − | | | | | | | | | |
| T270V /N114T | + | + | − | | | | | | | | | |
| T270V/N225C | − | + | − | | | | | | | | | |
| T270V/T140D | + | + | + | | | | | | | | | |
| M262L/S58E | − | − | + | | | | | | | | | |
| M262L/N114T | + | + | − | | | | | | | | | |
| M262L/N225C | − | + | − | | | | | | | | | |
| M262L/T140D | + | − | − | | | | | | | | | |
| S58E/N225C | + | + | − | | | | | | | | | |
| S58E/T140D | + | + | + | | | | | | | | | |
| N114T/N225C | − | + | − | | | | | | | | | |
| N225C/T140D | − | + | − | | | | | | | | | |
| S61T/N233K | | | | | + | + | + | + | | | | |
| S58A/N233K | | | | | − | + | + | + | | | | |
| R224Q/N233K | | | | | + | + | + | + | | | | |
| N233K/T270V/M262L/S58E/N114T/N225C/T140D | − | − | − | | − | − | | | + | − | + | |

TABLE 2-continued

| Mutation(s) | WT IsPETase | ThermoPETase | DuraPETase |
|---|---|---|---|
| S58E/N233K | ✓, + | ✓, + | |
| T67D/N233K | | ✓ | |
| Q91I/N233K | | ✓ | |
| N114T/N233K | ✓, + | ✓, + | |
| T140D/N233K | ✓, + | | |

Example 2: Cloning of *Ideonella* Sakaiensis 201-F6 IsPETase Gene

To enable the secretion of IsPETase in *Pseudomonas putida* KT2440, the nucleotide sequence of the signal peptide—SPpstu (21 amino acids) from maltotetraose-forming amylase of *Pseudomonas stutzeri* MO-19 (Fujita, M et al., 1989. "Cloning and Nucleotide Sequence of the Gene (AmyP) for Maltotetraose-Forming Amylase from

*Pseudomonas Stutzeri* MO-19." Journal of Bacteriology. https://doi.org/10.1128/jb.171.3.1333-1339.1989) was used to substitute the original signal peptide sequence (first 27 amino acids) of IsPETase to create the synthetic gene for cloning. The IsPETase gene with SPpstu presented at the N-terminus was amplified by polymerase chain reaction (PCR) using the synthetic gene as a template. Subsequently, using Gibson Assembly method, the PCR product was subcloned into a modified pBTK552 vector (Leonard, Sean P., et al. 2018. "Genetic Engineering of Bee Gut Microbiome Bacteria with a Toolkit for Modular Assembly of Broad-Host-Range Plasmids." ACS Synthetic Biology. https://doi.org/10.1021/acssynbio.7b00399) where the antibiotic resistance marker was switched from spectinomycine to kanamycin resistance gene. The electrocompetent cell *Escherichia coli* DH10β was transformed with the Gibson Assembly product by following a standard electroporation protocol. The resultant expression plasmid (designated as pLH2) DNA was extracted from the overnight culture of the cloning host by using the QIAprep Spin Miniprep kit (Qiagen). The DNA sequence of extracted plasmid was verified by Sanger sequencing. Electrocompetent cell of *P. putida* KT2440 was then transformed with the produced expression plasmid pLH2.

Example 3: IsPETase Protein Expression and Purification

A single colony of an *P. putida* KT2440 strain harboring the expression plasmid pLH2 was inoculated into 2 ml of Luria Bertani broth (LB) medium with 50 μg/ml kanamycin and grown overnight at 30° C./225 rpm. The overnight-grown culture (using 150 μl) was scaled up with 1000-fold dilution in a 500-ml shake flask and grown to a cell density of 0.6 (optical density [OD600]) at 37° C./225 rpm. Protein expression was induced by adding 0.2 mM of isopropyl β-D-1-thiogalactopyranoside (IPTG) and cells were cultured for 24 hours at 30° C./225 rpm.

For isolation of the secreted IsPETase, the induced cell culture was centrifuged at 14,000 g for 10 mins to obtain the supernatant that accommodates secretory proteins. The supernatant was purified by HisPur™ Ni-NTA Resin (Thermo Fisher Scientific) according to the manufacturer's instruction. Desalting of the protein elution was carried out by using Sephadex G-25 PD-10 columns (GE Healthcare) according to the manufacturer's instruction. All purification and desalting steps were performed at 4° C. in a cold room. Afterwards, the purified protein was concentrated by Amicon® Ultra Centrifugal Filters device (50 ml, 10 KDa cut-off) and preserved in Dulbecco's Phosphate Buffered Saline (pH 7.0). The protein concentration was determined by using the Coomassie Plus Bradford Assay kit (Thermo Fisher Scientific).

Example 4: Cloning of *Ideonella* Sakaiensis 201-F6 IsPETase Variant Gene

To create IsPETase variant with single point mutations predicted by the neural network modelling, site-directed mutagenesis was carried out using the PCR method described in the Q5® Site-Directed Mutagenesis Kit (New England Biolabs). Plasmid pLH2 was used as the template for mutagenesis PCR reaction. The corresponding primer sequences and annealing temperature were designed and generated by using the NEBaseChanger™ tool. Stellar™ Competent Cells (Clontech Laboratories) were used as the cloning host and transformed with the ligated plasmids using the heat-shock method provided in the manufacturer's instruction. Plasmid extraction, sequencing, and transformation into *P. putida* KT2440 with the plasmids encoding IsPETase variants were performed under the same conditions as described in Example 2 for plasmid pLH2.

Example 5: IsPETase Variant Protein Expression and Purification

Expression and purification of the IsPETase variants were performed under the same conditions as described in Example 3 for the IsPETase protein.

Example 6: In Vitro Analysis of Esterase Activity Analysis Using Resorufin Butyrate To compare enzyme activities for resorufin butyrate ester, 200 mM purified enzymes were incubated with 10 mM resorufin butyrate (Sigma-Aldrich) in 100 mM phosphate buffer (pH 8.0) at room temperature. More specially, the purified enzymes were first diluted with 100 mM phosphate buffer to yield a final concentration of 200 nM. Subsequently, 10 μl of each diluted enzyme sample was then pipetted into the wells of a 96-well back polystyrene micro-titer plate (Costar 3603, Corning). Assay reactions were initiated by adding 90 μl of the assay reagent—resorufin butyrate to each sample well, immediately followed by a continuous measurement of the fluorescence of resorufin (Ex/Em=535/588 nm) for 10 mins by the Infinite 200® PRO microplate plate reader (Tecan Group AG).

Example 7: In Vitro Analysis of PET Degradation Activity Using Commercial PET Film To evaluate the degradation rate of PET by IsPETases and its enzyme variants, commercial PET film (Goodfellow, U.S. 577-529-50; specification: 1.3-1.4 g cm$^{-3}$ density, 1.58-1.64 refractive index, $100 \times 10^{-13}$ cm$^3 \cdot$cm cm$^{-2}$ s$^{-1}$ Pa$^{-1}$ permeability to water @25° C., $20$-$80 \times 10^{-6}$ K$^{-1}$ coefficient of thermal expansion, 0.13-0.15 W m-1 K-1 @23° C. thermal conductivity) was used as the substrate for degradation assays with the purified IsPETase enzyme and its variants secreted from *P. putida*. The PET film was prepared in a circular form with 6 mm diameter and was washed three times with 1% SDS, 20% ethanol, and deionized water. Subsequently, the film was added into a glass test tube containing 200 nM of purified IsPETase in 50 mM pH 9.0 Glycine-NaOH buffer. The reaction mixture was then incubated at 30/40/50/55° C. for 48/96 hours. Subsequently, the resultant PETase-treated films were washed again for three times followed by drying the samples under vacuum at 30° C. for 24 hours prior to gravimetric measurement. The weight of the PET film samples before and after enzyme treatment were compared to calculate the mass loss.

Figure 2:
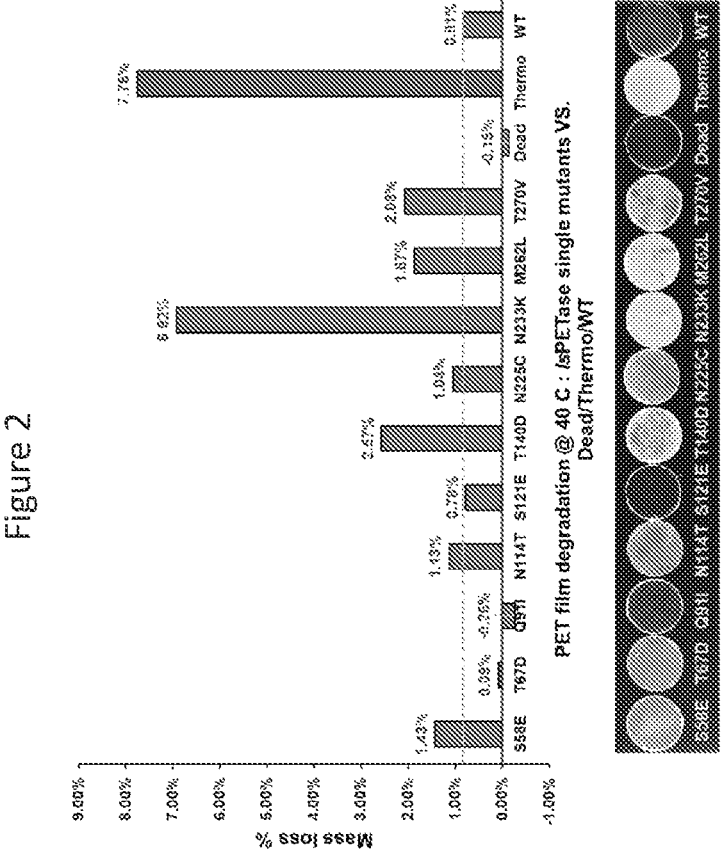
FIG. 2 is a bar graph showing the PET degradation activity of IsPETase variants containing a series of mutations predicted by the neural network analysis, a disabled IsPETase, and ThermoPETase, as compared to the wild type IsPETase. PET film was used as the substrate and the hydrolysis activities of the wild type IsPETase and its variants were measured at an enzyme concentration of 200 nM. Assay reactions were incubated at 40° C. for 96 hours. PET film samples before and after enzyme treatment were compared to measure the mass loss of the resultant PETase-treated films. Photograph of the resultant PETase-treated films shows different extents of surface erosion due to different degradation activities of the IsPETase variants. "Thermo" stands for the ThermoPETase that contains mutations S121E, D186H and R280A; "Dead" stands for a disabled IsPETase that has been mutated (S160A) to lose its enzymatic function; "WT" stands for the wild type IsPETase. All samples are purified protein samples and normalized to protein concentration.
Figure 3:
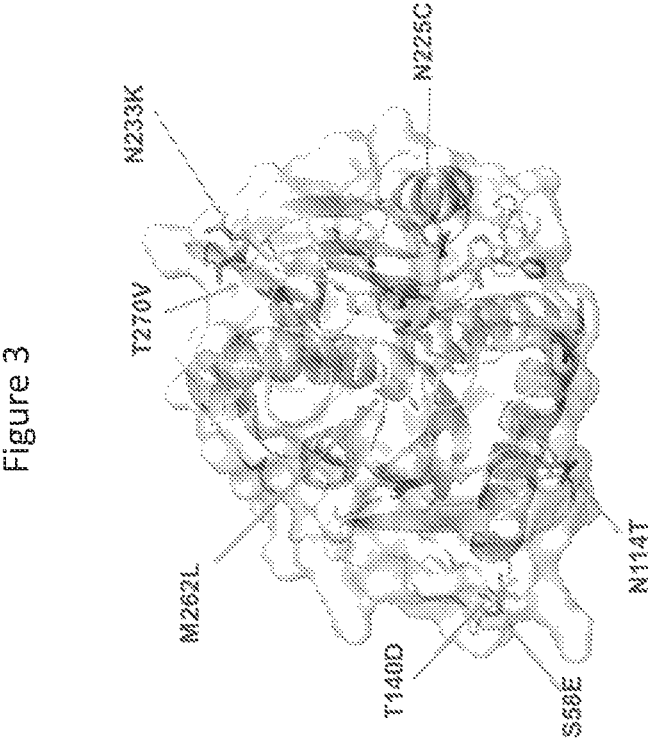
FIG. 3 shows the residue locale of the 7 initially-predicted neural network mutations that exhibit higher PET degradation activity compared to wild type IsPETase
Figure 4:
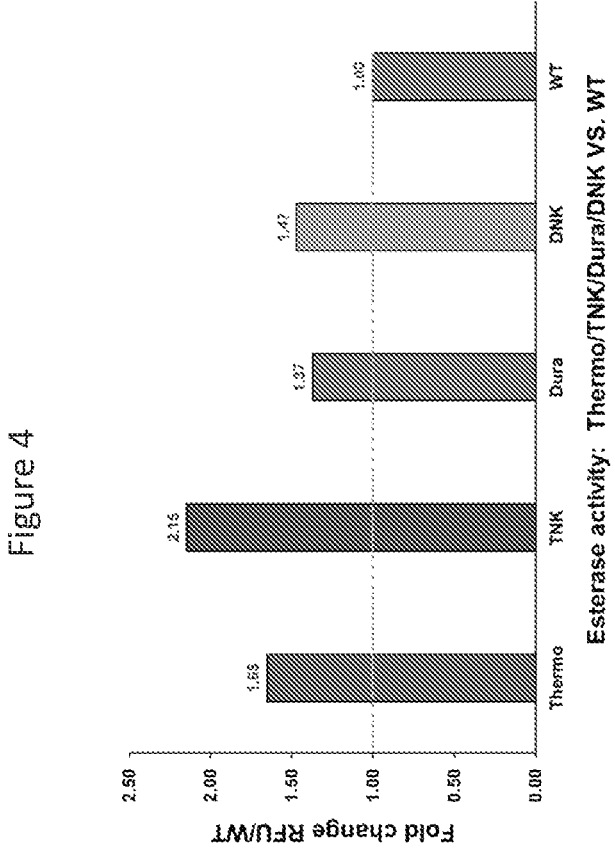
FIG. 4 is a bar graph showing the esterase activity of IsPETase variants as compared to the wild type IsPETase. The esterase activities of the wild type IsPETase and its variants are measured by the resorufin butyrate assay. "Thermo" stands for the ThermoPETase that contains mutations S121E, D186H and R280A; "TNK" stands for a ThermoPETase variant that contains mutation N233K; "Dura" stands for the DuraPETase that contains mutations L117F, Q119Y, T140D, W159H, G165A, I168R, A180I, S188Q, S214H, R280A; "DNK" stands for a DuraPETase variant that contains mutation N233K; "WT" stands for the wild type IsPETase. All samples are purified protein samples and normalized to protein concentration.

In one experiment, using the PET film degradation assay as described above, the PET degradation activity of the IsPETase Net single variants is compared to the wild type IsPETase, a mutated PETase with complete loss of activity, and the ThermoPETase. The assay reaction was incubated at 40° C. for 96 hours. The result is shown in FIG. 2. The result demonstrates that N233K, S58E, N114T, N225C, M262L, T270V, T140D are beneficial substitutions that can lead to higher PET degradation activity of the mutants relative to wild type IsPETase. Among these single mutants, the variant comprising mutation N233K led to the greatest improvement, exhibiting an approximately 8.5-fold higher PET degradation activity than the wild type IsPETase.

Figure 5:
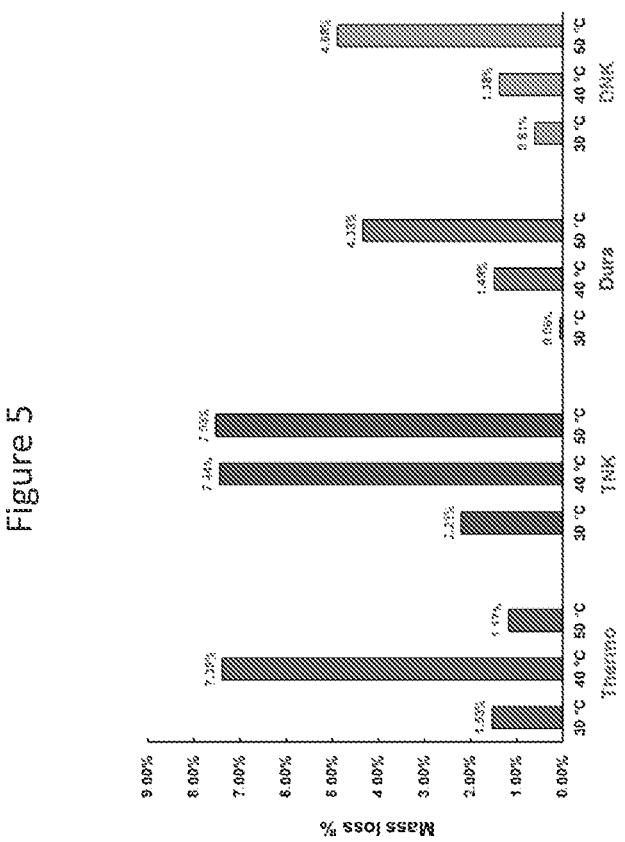
FIG. 5 is a bar graph showing the PET degradation activity of IsPETase variants at different temperatures. PET film was used as the substrate and the hydrolysis activities of the IsPETase variants were measured at an enzyme concentration of 200 nM. Assay reactions were incubated at 30 and 40° C. for 96 hours, and 50° C. for 48 hours. PET film samples before and after enzyme treatment were compared to measure the mass loss of the resultant PETase-treated films. "Thermo" stands for the ThermoPETase that contains mutations S121E, D186H and R280A; "TNK" stands for a ThermoPETase variant that contains mutation N233K; "Dura" stands for the DuraPETase that contains mutations L117F, Q119Y, T140D, W159H, G165A, I168R, A180I, S188Q, S214H, R280A; "DNK" stands for a DuraPETase variant that contains mutation N233K. All samples are purified protein samples and normalized to protein concentration.
Figure 6:
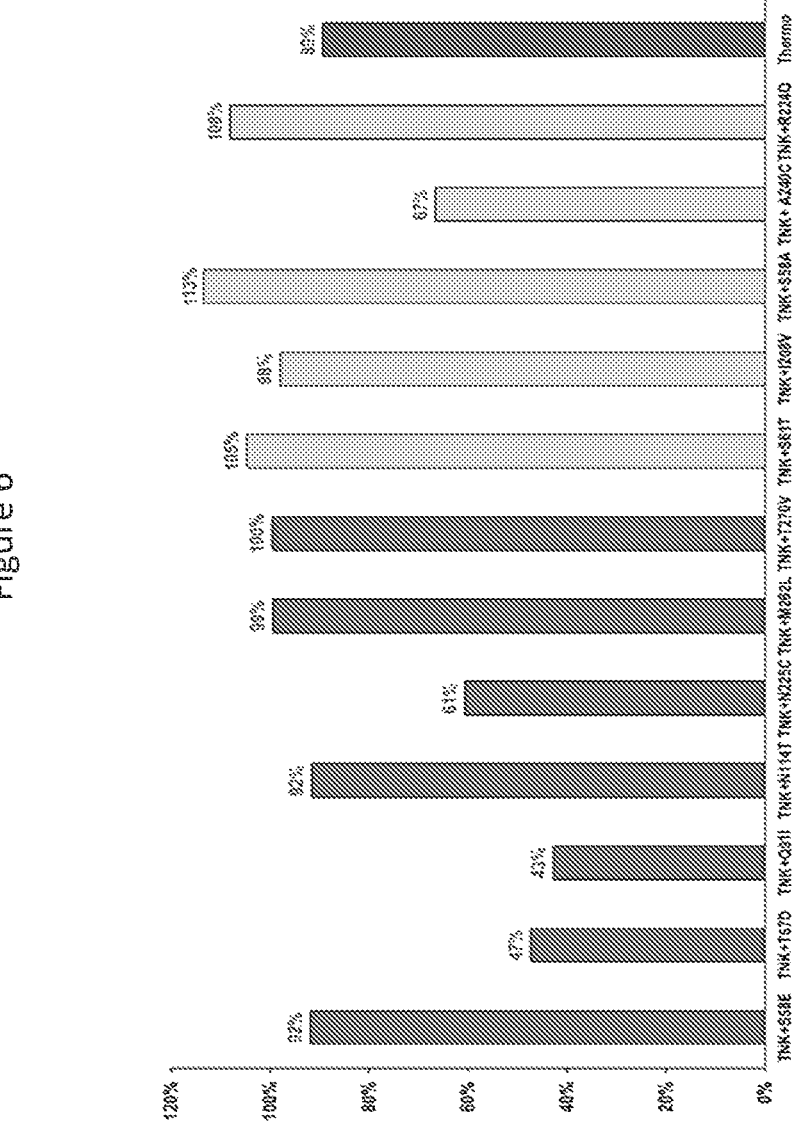
FIG. 6 is a bar graph showing the esterase activity of TNK (a IsPETase variant that contains mutations S121E, D186H, R280A and N233K) variants containing a series of mutations predicted by the neural network analysis, ThermoPETase, and DuraPETase, as compared to the TNK. The esterase activities of the ThermoPETase, DuraPETase, TNK and its variants are measured by the resorufin butyrate assay. "Thermo" stands for the ThermoPETase that contains mutations S121E,D186H and R280A; "TNK" stands for a ThermoPETase variant that contains mutation N233K; "TNK+X" stands for the TNK variants that contains one of the mutations predicted by the neural network analysis; "Dura" stands for the DuraPETase that contains mutations L117F, Q119Y, T140D, W159H, G165A, I168R, A180I, S188Q, S214H, R280A; "DNK" stands for a DuraPETase variant that contains mutation N233K. All samples are purified protein samples and normalized to protein concentration.

In one experiment, using the same PET film degradation assay as described above, the PET degradation activity of the TNK and DNK was compared to ThermoPETase and DuraPETase respectively. The assay reaction was incubated at 30/40° C. for 96 hours, or 50° C. for 48 hours. The result is shown in FIG. 5. The result demonstrates that the substitution N233K in the amino acid sequences of Thermo-PETase and DuraPETase also resulted in improved PET degradation performance. Specifically, while TNK showed an almost similar PET degradation activity with Thermo-PETase at 30 and 40° C., TNK exhibited 6.4-fold higher activity than ThermoPETase at 50° C. This suggested that the substitution N233K further improve the thermal toler-ance of ThermoPETase. In contrast, DNK only exhibited slightly higher PET degradation activity than DuraPETase at 50° C.

Figure 7:
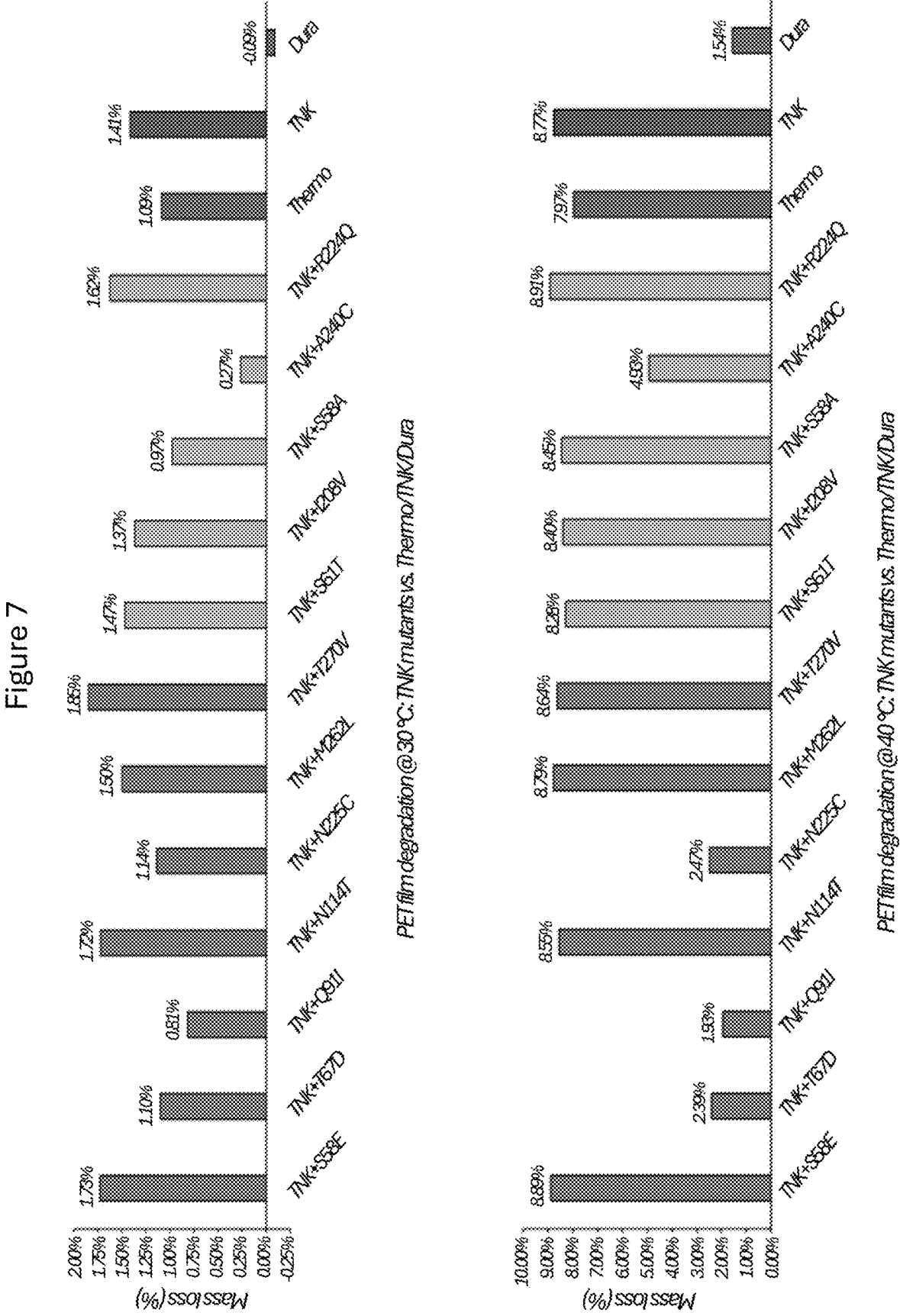
FIG. 7 is a bar graph showing the PET degradation activity of TNK (A IsPETase variant that contains mutations S121E, D186H, R280A and N233K) variants containing a series of mutations predicted by the neural network analysis, ThermoPETase, and DuraPETase as compared to the TNK, at different temperatures. PET film was used as the substrate and the hydrolysis activities of the IsPETase variants were measured at an enzyme concentration of 200 nM. Assay reactions were incubated at 30, 40, 50 or 55° C. for 96 hours. PET film samples before and after enzyme treatment were compared to measure the mass loss of the resultant PETase-treated films. "Thermo" stands for the ThermoPETase that contains mutations S121E, D186H and R280A; "TNK" stands for a ThermoPETase variant that contains mutation N233K; "TNK+X" stands for the TNK Net single variants that contains one of the mutations S58E, N114T, N225C, M262L, T270V, T67D, Q91I, S121E, T67D, Q91I, S61T, 1208V, S58A and R224Q predicted by the neural network analysis; "Dura" stands for the DuraPETase variant that contains mutations L117F, Q119Y, T140D, W159H, G165A, I168R, A180I, S188Q, S214H, R280A; "DNK" stands for a DuraPETase variant that contains mutation N233K. All samples are purified protein samples and normalized to protein concentration.

In another experiment, using the PET film degradation assay as described above, the PET degradation activity of the TNK Net single variants is compared to the Thermo-PETase, DuraPETase and TNK. The assay reaction was incubated at 30/40/50/55° C. for 96 hours. The results are shown in FIG. 7. The results demonstrate that S58E, N114T, N225C, M262L, T270V, S58A, S61T, I208V and R224Q are beneficial substitutions that can lead to higher PET degra-dation activity of the mutants relative to wild type IsPETase. Among these single mutants, variant comprising mutation N233K led to the greatest improvement, exhibiting an approximately 8.5-fold higher PET degradation activity than the wild type IsPETase.

Example 8

Based upon structural analysis of the enzyme, the follow-ing further residues were identified for substitution to improve activity:

S58Y—A tyrosine can form a cation-pi interaction with R59, hydrogen bond with S142 and S143 and nearby water molecules, keeping the protein from unfolding at higher temperatures.

S58M/L/V—A methionine, leucine, isoleucine, and valine can help keep the unstructured loop collapsed into the hydrophobic pocket formed between the alpha helix and the beta sheet, keeping them together at higher temperatures.

S58P—A proline can limit the flexibility in the unstruc-tured loop between the 2 beta-strands, keeping them together at higher temperatures.

S61D/E—The serine is currently forming a hydrogen bond with R132. This Arginine is not near any anionic residue but rather close to R59 resulting in a repulsive electrostatic interaction. An ASP or GLU at this residue will add an anion in between R59 and R132, resulting in attrac-tive electrostatics that will keep the protein folded at higher temperatures.

S61Y/F—Can form a cation pi interaction with both R59 and R132, resulting in attractive electrostatics that will keep the protein folded at higher temperatures.

N114H/L/R—Can form a salt bridge with D118 and can hydrogen bond with Q126 and the backbone residues T63 and G64.

N114S/T—Can hydrogen bond with D118 and Q126 and the backbone residues T63 and G64.

T140: This threonine is in a partially solvent exposed unstructured loop.

T140Y—A tyrosine can preserve hydrogen bonding with the solvent and potentially form a cation-pi interaction with R59.

T140L/I/V—Can help the hydrophobic collapse between the beta sheets and the alpha helix this unstructured loop stem from.

T140S—Can help interaction with solvent and hydrogen bonds with S142 and S143 in the unstructured loop to keep the loop tight.

I208M/H/F/Y—Can interact with the pi electrons of the nearby residues (Y87, W185, H237) and of the benzene ring of the terephthalate substrate.

I208P—This is an unstructured loop that needs some order to keep the D206 properly positioned in the catalytic triad. Removing some flexibility within this unstructured loop will allow the catalytic triad to function at higher temperatures.

I208A—Will remove potential steric hindrance to the active site's nucleophilic S160.

R224D/E—This arginine is solvent exposed with no nearby anionic residue and appears to have repulsive inter-action with K177, K227, R260. Therefore, placing an anionic amino acid (ASP/GLU) will improve electrostatics of the region and increase thermostability.

R224S/T/N/Q—These amino acid remove the repulsive cation and ease the electrostatic interactions in the region and contribute to hydrogen bonding.

N225N—ASN is in a hydrophobic pocket. But hydrogen bonding with backbone carbonyls.

N225I/V/M/A/L—Will increase the hydrophobicity of the pocket and keep it from unfolding at higher temperature.

N225S/T—preserve the backbone hydrogen bond to T195 and V196 but does not stick out as far into the hydrophobic pocket.

N233R/Y/H—This asparagine is next to 3 anions (E204, E231, D283) and a cation will ease the strong repulsive electrostatics in the region.

N233P—This asparagine is at the very end of a beta-strand and at the beginning of an unstructured loop that hold the catalytic histidine in the active site. A proline will cap this beta strand and aid some rigidity to the catalytic His, keeping it catalytically active at higher temperatures.

M262: This methionine is in a tight hydrophobic pocket with the centered beta-sheet.

M262L/I/A/V—Other hydrophobic residues may have stronger hydrophobic interactions due to sterics and keep the protein from unfolding at higher temperatures.

M262F/W—pi-pi stacking with F106 can strengthen the hydrophobic collapse.

T270Y/R/H—A cation can form a salt bridge with E274 and a cation-pi interaction with F271, allowing this region to retain the local structure at higher temperatures.

Example 9

Increased production and accumulation of plastic waste poses an ecological challenge. While current plastic waste management largely relies on unsustainable, energy-inten-sive, or even hazardous physicochemical and mechanical processes, enzymatic degradation offers a green and sustain-able route for plastic waste recycling. Poly(ethylene tereph-thalate) (PET) has been extensively used in packaging and for the manufacture of fabrics and single-used containers, accounting for 12% of the global solid waste. However, despite several PET hydrolases reported to date, their prac-tical applications, including bioremediation, are hampered by either the lack of robustness, or the requirement of a fairly high reaction temperature (ca. 70° C.). Here, we use a structure-based, deep learning model to engineer a highly robust and functional PET hydrolase from *Ideonella* sakaiensis. Our best resulting mutant (αPETase) not only exhibits superior PET-hydrolytic activity to its counterparts, including a leaf-branch compost cutinase and its mutant, over a wide range of modest temperatures (especially 30-50° C.), but also possesses enhanced thermostability and pH tolerance. We demonstrate that untreated, post-consumer PET from 51 different plastic products can all be degraded completely by αPETase within one week and in as little as 24 hours at 50° C. We also show that virgin PET can be re-synthesized by polymerizing the monomers recovered from the enzymatic depolymerization of PET waste by αPETase, demonstrating a closed-loop PET recycling process. The predominant activity at moderate temperatures and the exceptional compatibility with microbes render αPETase an ideal catalyst for both enzyme-based and cell-based platforms. In this regard, we demonstrate sequential and consolidated bioprocesses whereby an engineered *Pseudomonas* strain expressing secreted αPETase is able to degrade PET and utilized the degradation product—terephthalic acid—as carbon and energy source for growth, suggesting the great potential of αPETase for environmental bioremediation application.

Poly(ethylene terephthalate) (PET) composes 70% of synthetic textile fibers and 10% of non-fiber plastic packaging (Geyer, R., Jambeck, J. R. & Law, K. L. Production, use, and fate of all plastics ever made. *Sci. Adv.* 3, (2017)), and correspondingly represents an enormous waste stream of single-use manufactured materials. Yet, a circular carbon economy for PET is theoretically attainable through rapid enzymatic depolymerization followed by chemical repolymerization or upcycling/valorization into other products (Simon, N. et al. A binding global agreement to address the life cycle of plastics. *Science* (80-.). 373, 43 LP-47 (2021)), (Kawai, F., Kawabata, T. & Oda, M. Current knowledge on enzymatic PET degradation and its possible application to waste stream management and other fields. *Applied Microbiology and Biotechnology* 103, (2019)). However, all existing PET-hydrolyzing enzymes (PHEs) are limited in their capacity to either function within modest pH/temperature ranges or directly utilize untreated post-consumer plastics. Such traits are essential for in situ bioremediation and for simplified, low-cost industrial-scale processes (Taniguchi, I. et al. Biodegradation of PET: Current Status and Application Aspects. *ACS Catal.* (2019). doi:10.1021/acscatal.8b05171). To overcome these limitations, we employed deep learning and protein engineering approaches to generate a PHE that has exceptionally high activity across a broad range of raw PET substrates (both model and actual post-consumer PET), temperatures, and PH levels in a manner that out-performs all other known PHEs and derived mutants.

Enzymatic depolymerization of PET was first reported in 2005 and has been nascently demonstrated using 19 distinct PHEs derived from esterases, lipases, and cutinases (Taniguchi, I. et al. Biodegradation of PET: Current Status and Application Aspects. *ACS Catal.* (2019). doi:10.1021/acscatal.8b05171), (Inderthal, H., Tai, S. L. & Harrison, S. T. L. Non-Hydrolyzable Plastics—An Interdisciplinary Look at Plastic Bio-Oxidation. *Trends in Biotechnology* (2021). doi:10.1016/j.tibtech.2020.05.004), (Chen, C. C., Dai, L., Ma, L. & Guo, R. T. Enzymatic degradation of plant biomass and synthetic polymers. *Nature Reviews Chemistry* (2020). doi:10.1038/s41570-020-0163-6). However, the majority of these enzymes only show appreciable hydrolytic activity at high reaction temperatures (i.e. at or exceeding the PET glass transition temperature of ca. 70° C.). For example, an engineered leaf-branch compost cutinase (LCC) can degrade 90% of pretreated post-consumer PET within 10 hours at 72° C. and a pH of 8.0 (Tournier, V. et al. An engineered PET depolymerase to break down and recycle plastic bottles. *Nature* (2020). doi:10.1038/s41586-020-2149-4). Most other PHEs similarly show poor activity at moderate temperatures (Yoshida, S. et al. A bacterium that degrades and assimilates poly(ethylene terephthalate). *Science* (80-.). (2016). doi:10.1126/science.aad6359) and more neutral pH conditions (Chen, C. C. et al. General features to enhance enzymatic activity of poly(ethylene terephthalate) hydrolysis. Nat. Catal. (2021). doi:10.1038/s41929-021-00616-y), greatly restricting in situ/microbially-enabled bioremediation solutions for PET waste. This limitation is of critical concern as 40% of uncollectable plastics reside in natural environments (Worm, B., Lotze, H. K., Jubinville, I., Wilcox, C. & Jambeck, J. Plastic as a Persistent Marine Pollutant. *Annual Review of Environment and Resources* (2017). doi:10.1146/annurev-environ-102016-060700). In addition, converting untreated post-consumer plastic waste at near ambient temperature would be preferable for industrial applications, whereas elevated temperatures and pretreatment increase net operating costs.

While the PHE from the PET-assimilating bacterium *Ideonella* sakaiensis (Yoshida, S. et al. A bacterium that degrades and assimilates poly(ethylene terephthalate). *Science* (80-.). 351, 1196 LP-1199 (2016).) (PETase) can operate at ambient conditions, it is highly labile and loses activity even at 37° C. after 24 hours (Son, H. F. et al. Rational Protein Engineering of Thermo-Stable PETase from *Ideonella* sakaiensis for Highly Efficient PET Degradation. *ACS Catal.* 9, 3519-3526 (2019)), thereby limiting practical applications. Nonetheless, this mesophilic enzyme has previously seen attempts to enhance thermostability, robustness and function (Son, H. F. et al. Rational Protein Engineering of Thermo-Stable PETase from *Ideonella* sakaiensis for Highly Efficient PET Degradation. *ACS Catal.* 9, 3519-3526 (2019)), (Austin, H. P. et al. Characterization and engineering of a plastic-degrading aromatic polyesterase. *Proc. Natl. Acad. Sci. U.S.A* 115, E4350-E4357 (2018)), (Joo, S. et al. Structural insight into molecular mechanism of poly(ethylene terephthalate) degradation. *Nat. Commun.* 9, (2018)), (Han, X. et al. Structural insight into catalytic mechanism of PET hydrolase. *Nat. Commun.* (2017). doi:10.1038/s41467-017-02255-z), (Furukawa, M., Kawakami, N., Oda, K. & Miyamoto, K. Acceleration of Enzymatic Degradation of Poly(ethylene terephthalate) by Surface Coating with Anionic Surfactants. *ChemSusChem* (2018). doi:10.1002/cssc.201802096), (Cui, Y. et al. Computational Redesign of a PETase for Plastic Biodegradation under Ambient Condition by the GRAPE Strategy. *ACS Catal.* (2021). doi:10.1021/acscatal.0c05126), (Chen, K., Hu, Y., Dong, X. & Sun, Y. Molecular Insights into the Enhanced Performance of EKylated PETase Toward PET Degradation. *ACS Catal.* 11, 7358-7370 (2021)). The most notable engineered PETase variants ThermoPETase (Son, H. F. et al. Rational Protein Engineering of Thermo-Stable PETase from *Ideonella* sakaiensis for Highly Efficient PET Degradation. *ACS Catal.* 9, 3519-3526 (2019)) and DuraPETase (Cui, Y.-L. et al. *Computational redesign of PETase for plastic biodegradation by GRAPE strategy.* (2019). doi:10.1101/787069)— were created through rational protein engineering and computational redesign strategies, respectively. Although the thermostability and catalytic activity of these two mutants were improved (Son, H. F. et al. Rational Protein Engineering of Thermo-Stable PETase from *Ideonella* sakaiensis for Highly Efficient PET Degradation. *ACS Catal.* 9, 3519-3526 (2019)), (Cui, Y. et al. Computational Redesign of a PETase for Plastic Biodegradation under Ambient Condition by the GRAPE Strategy. *ACS Catal.* (2021). doi:10.1021/acscatal.0c05126) under certain conditions, they had overall lower PET-hydrolytic activity at mild temperatures.

Figure 9B:
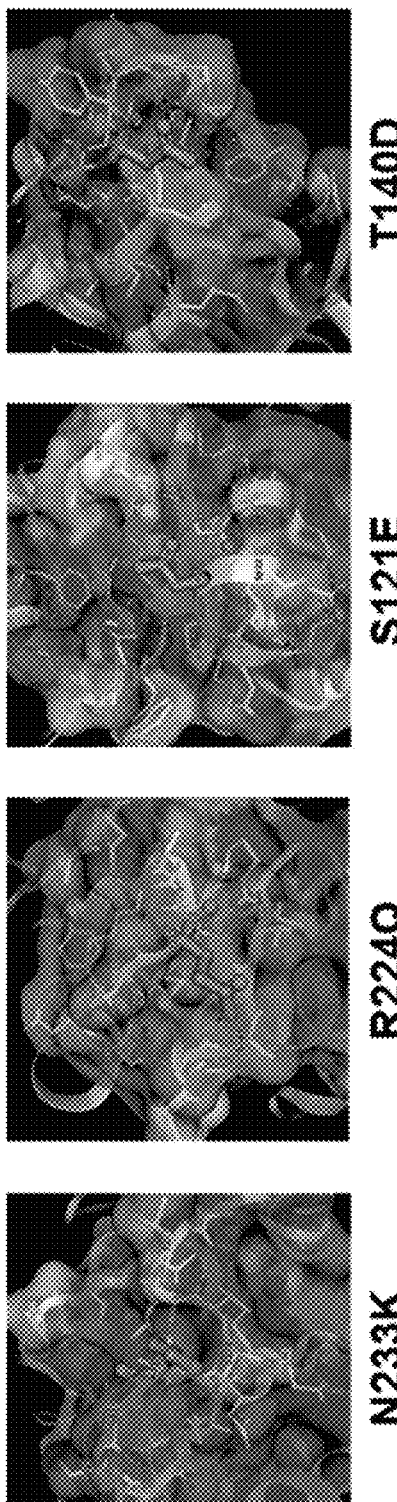

We posited that more focused protein engineering approaches cannot overcome the evolutionary tradeoff between overall stability and activity, and that a neutral, structure-based, deep learning neural network might generally improve enzyme function across all conditions. To this end, we employed our 3D self-supervised, convolutional neural network, MutCompute (Shroff, R. et al. Discovery of novel gain-of-function mutations guided by structure-based deep learning. *ACS Synth. Biol.* (2020). doi:10.1021/acssynbio.0c00345). This algorithm is trained on over 19,000 sequence-diverse protein structures from the Protein Data Bank to link amino acid residues with the local chemical microenvironment. Specifically, we employed MutCompute to obtain a discrete probability distribution for structural fit simulating all 20 canonical amino acids at each residue in both wild-type PETase and ThermoPETase (crystal structures PDB: 5XJH and 6IJ6). To assist with down selection of critical residues for mutation, this distribution was rendered onto the protein crystal structure (FIG. 9a) to identify positions wherein the wild-type amino acid residues were 'less fit' than potential substitutions. To focus experimental protein engineering efforts, these predictions were also ranked by predicted fold change of fit probabilities to identify and target the most highly incongruent residues for mutagenesis. Using a stepwise combination strategy, we generated a total of 159 variants using residues on this list to incorporate single or multiple predicted mutations into various PETase scaffolds. Variants exhibiting improved catalytic activity (as measured by esterase activity and plastic degradation rates) and thermostability (as measured by protein melting temperature ($T_m$)) were characterized further. Among this set, four predicted mutations (S121E, N233K, R224Q and T140D) (FIG. 9b) resulting in the highest improvements both singly and in combination and were therefore selected for further combinatorial assembly and follow-up analysis.

Figure 13:
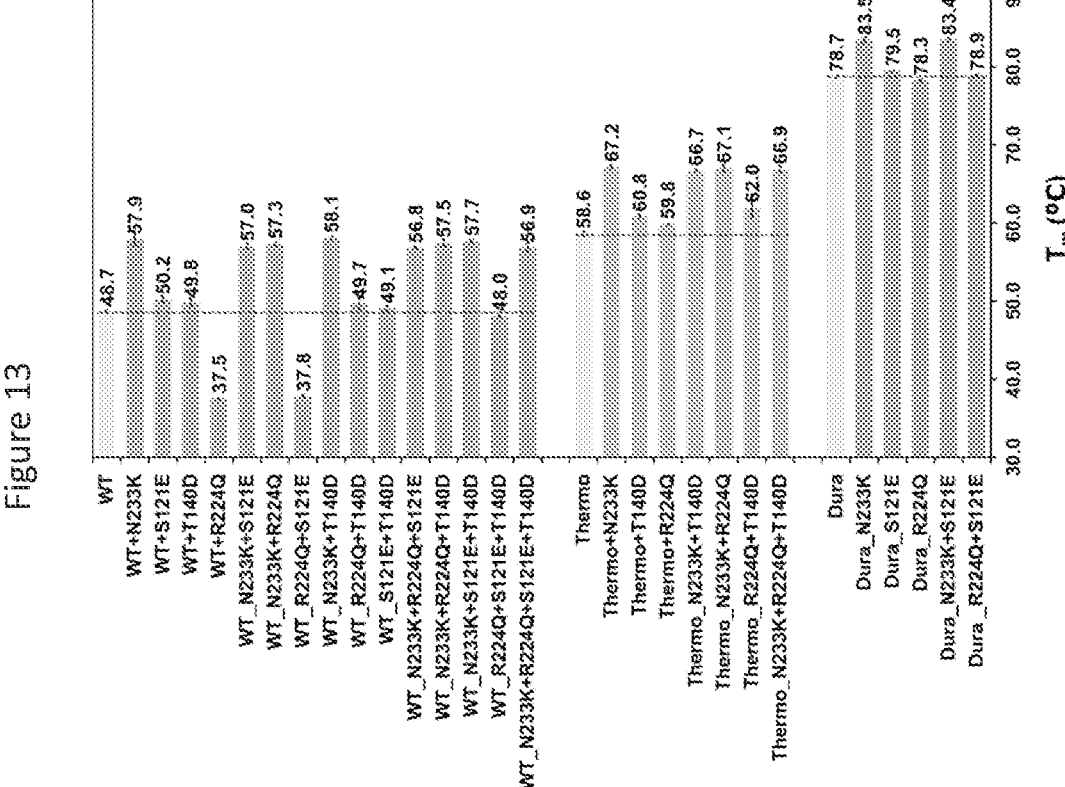
FIG. 13|Thermostability of the PETase variants incorporating the mutations predicted by Mutcompute and their respective scaffolds-wild-type PETase (WT), Thermo-PETase (Thermo), DuraPETase (Dura). The melting temperature of each enzyme was determined by differential scanning calorimetry. All measurement were conducted in triplicate (n=3).

We assembled all 29 possible combinations of these four mutations across three PETase scaffolds (wild-type PETase, ThermoPETase, and DuraPETase). Of note, two could not be purified using the DuraPETase background after multiple attempts. Thermostability analysis of the remaining 27 mutants indicated that 24 (ca. 89%) resulted in elevated $T_m$ relative to their respective scaffolds (FIG. 13). The highest change in thermostability from their respective PETase scaffolds were observed for variants PETase$^{N233K/T140D}$ with a $T_m$ of 58.1° C. ($\Delta T_m$=10° C. from WT PETase), ThermoPETase$^{N233K/R224Q}$ with a $T_m$ of 67.4° C. ($\Delta T_m$=9° C. from ThermoPETase), and DuraPETase$^{N233K}$ with a $T_m$ of 83.5° C. ($\Delta T_m$=5° C. from DuraPETase). The latter mutant represents the most thermostable PETase mutant reported to date. It was noted that the protein yield of all 27 variants was improved (up to 3.8-fold increase) compared with the parental scaffold, further underscoring the ability of Mutcompute to identify mutants of higher stability. The portability and combinatorial synergy of these mutations across scaffolds demonstrates the power of this neural network-based approach.

Figure 9C:
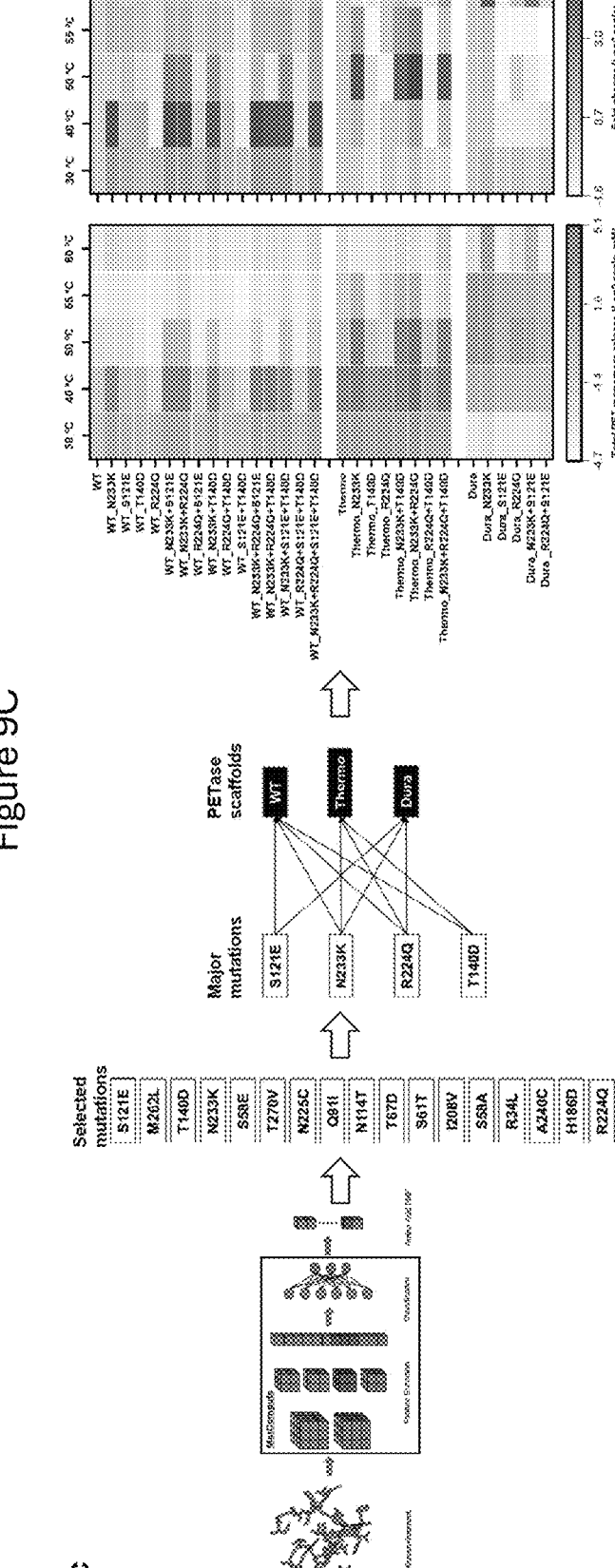

Next, we sought to evaluate the PET hydrolytic activity of these more stable variants across a range of temperatures from 30 to 60° C. using an amorphous PET film (gf-PET, from the supplier Goodfellow) commonly used in the literature (Tournier, V. et al. An engineered PET depolymerase to break down and recycle plastic bottles. *Nature* (2020). doi:10.1038/s41586-020-2149-4). This comparison immediately revealed that the machine-learning guided predictions greatly enhanced PET-hydrolytic activity and extended the range of working temperature in all scaffolds (FIG. 9c). In particular, PETase$^{N233K/R224Q/S121E}$ exhibited a 3.4-fold and 29-fold increase in PET-hydrolytic activity at 30 and 40° C. respectively, over wild-type PETase (FIG. 9c). Enzyme mutants based on the ThermoPETase scaffold showed an extended range of working temperature (30-60° C.) and exhibited significantly higher activity than their counterparts. Within this set, the best ThermoPETase variant-ThermoPETase$^{N233K/R224Q}$, named αPETase, exhibited 2.4-fold and 38-fold higher activity at 40 and 50° C., respectively compared to ThermoPETase alone (FIG. 9c). At 50° C., αPETase exhibited the highest overall degradation of all mutants and temperatures activity releasing 33.8 mM of PET monomers in 96 hours (FIG. 9c). The DuraPETase scaffold in general exhibited relatively low activity at mild temperatures (30-50° C.), but improvements were nevertheless realized at higher temperatures (55-60° C.) as demonstrated by the most thermostable PETase mutant-DuraPETase$^{N233K}$, named βPETase (FIG. 9c).

Figure 10:
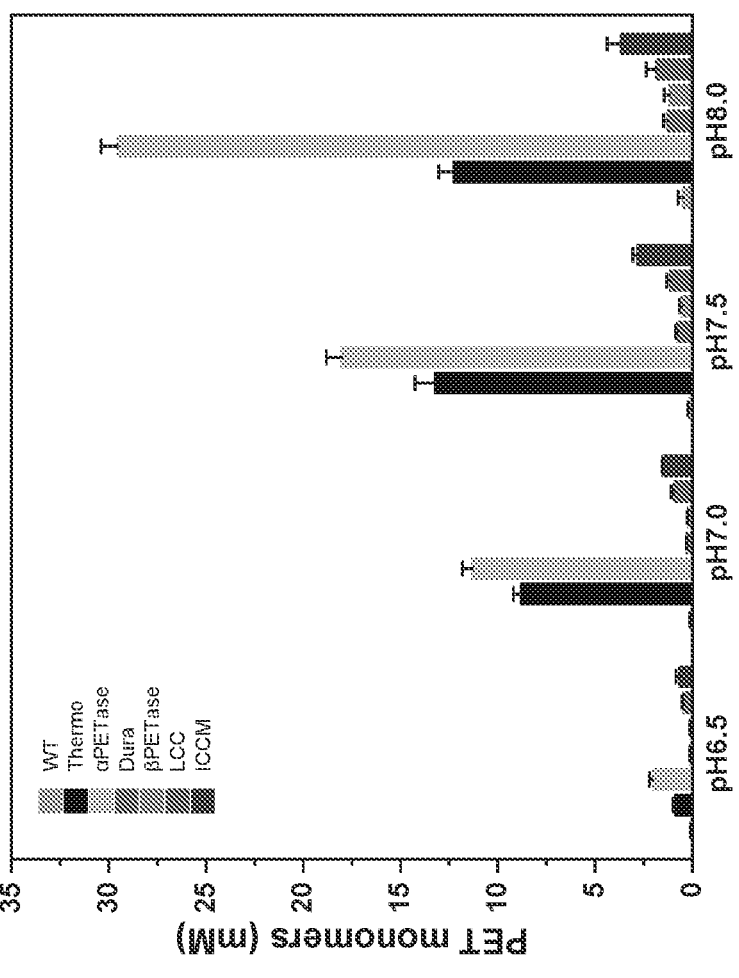
FIG. 10 The PET-hydrolytic activity of αPETase outperformed various PHEs at mild temperatures and modest pH. Comparison of PET-hydrolytic activity of αPETase, wild-type PETase (WT), ThermoPETase (Thermo), DuraPETase (Dura), βPETase, LCC and ICCM across a range of pH (6.5-8.0) at reaction temperature of 40° C. PET-hydrolytic activity was evaluated by measuring the amount of PET monomers (the sum of TPA and MHET) released from hydrolyzing gf-PET film by the tested PHEs after 96 hrs of reaction time. All measurements were conducted in triplicate (n=3).

To evaluate the catalytic resilience of these mutants to environmental conditions, αPETase and βPETase were compared to previously reported wild-type and mutant PHEs including wild-type PETase, ThermoPETase, DuraPETase, LCC, the most active mutant LCC$^{F243I/D238C/S283C/N246M}$ (ICCM) using gf-PET across a range of pH (6.5-8.0) at 40° C. (FIG. 10). This comparative analysis demonstrated the unique catalytic capability of αPETase to function at low PH levels and ambient temperature. Specifically, αPETase outperformed other PHEs at all pH conditions. Especially at pH 7, αPETase exhibited activities that were 115 times as high as that of wild-type PETase at 40° C. (FIG. 10). This enzymatic performance makes αPETase an excellent candidate for mild temperatures and modest pH enzymatic degradation of PET seen in conditions of in situ plastic bioremediation.

Figure 11A:
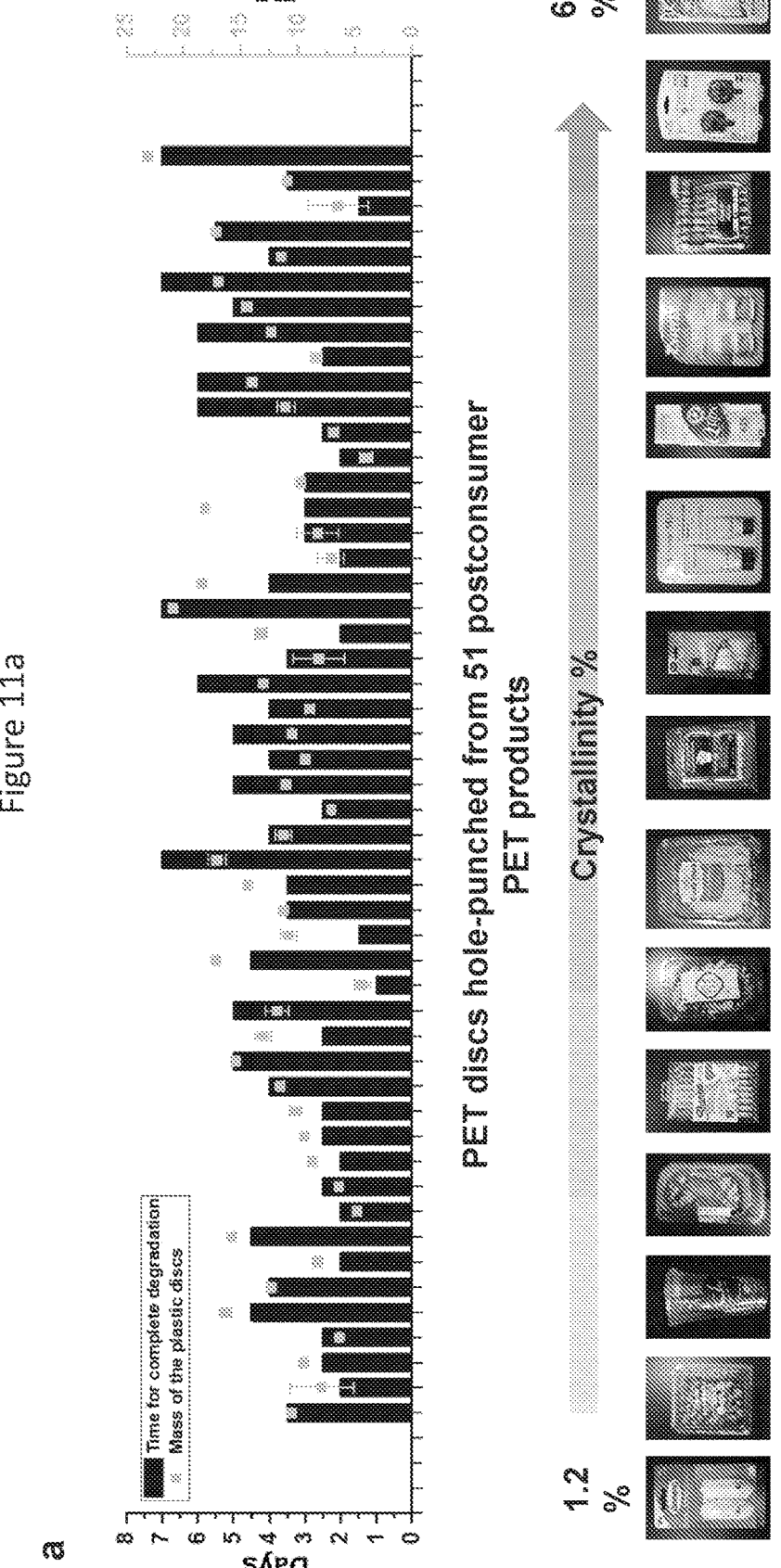
FIG. 11*a-d* The superior performance of αPETase in enzymatic depolymerization of post-consumer PET plastic and polyester products. 11*a*. Complete degradation of pc-PET films hole-punched from 51 post-consumer plastic products. 11*b*. Time-course of PET-hydrolytic activity of αPETase, wild-type PETase (WT), ThermoPETase (Thermo), DuraPETase (Dura), βPETase, LCC and ICCM at reaction temperature of 50° C. PET-hydrolytic activity was evaluated by measuring the amount of PET monomers (the sum of TPA and MHET) released from hydrolyzing pc-PET (Bean cake plastic container) film by the tested PHEs at various time points. $KH_2PO_4$—NaOH (pH8) buffer was used for all enzymes shown in this figure. All measurements were conducted in triplicate (n=3). 11*c*. Atomic Force Microscopy images of pc-PET films following various exposure times with αPETase. 11*d*. Complete degradation of large, untreated PET container with αPETase at 50° C. e. Degradation of commercial polyester products with αPETase, wild-type PETase (WT), ThermoPETase (Thermo), DuraPETase (Dura), βPETase, LCC and ICCM at 50° C.

Beyond model plastic substrates, it is critical to demonstrate the performance of PETase enzymes on raw, untreated post-consumer PET (pc-PET). Notably, unlike the gf-PET used above and throughout the literature, there is no singular post-consumer PET substrate. To this end, we collected 51 samples of post-consumer plastic products used in the packaging of food, beverages, medications, office supplies, household goods and cosmetics available at local grocery store chains and treated this raw material enzymatically with αPETase at 50° C. (FIG. 14). Despite their heterogeneity including physical properties such as crystallinity and thickness as well as different compositions including additives and plasticizers, hole-punched samples from this wide array of PET products were all fully degraded by αPETase within one week and in as little as 24 hours (FIG. 11a). While thickness of the plastic did correlate with degradation time (as thickness and mass are related), neither this metric nor crystallinity alone determined overall degradation rates.

Figure 11B:
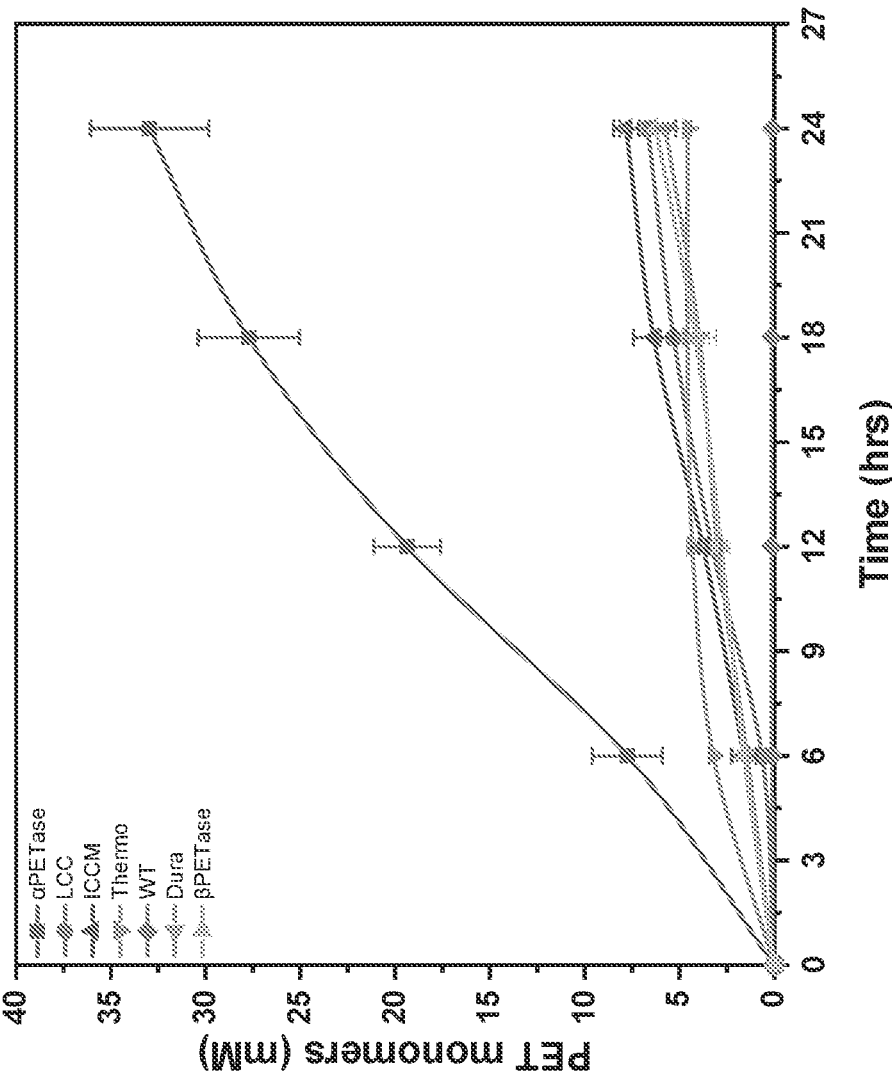
Figure 11C:
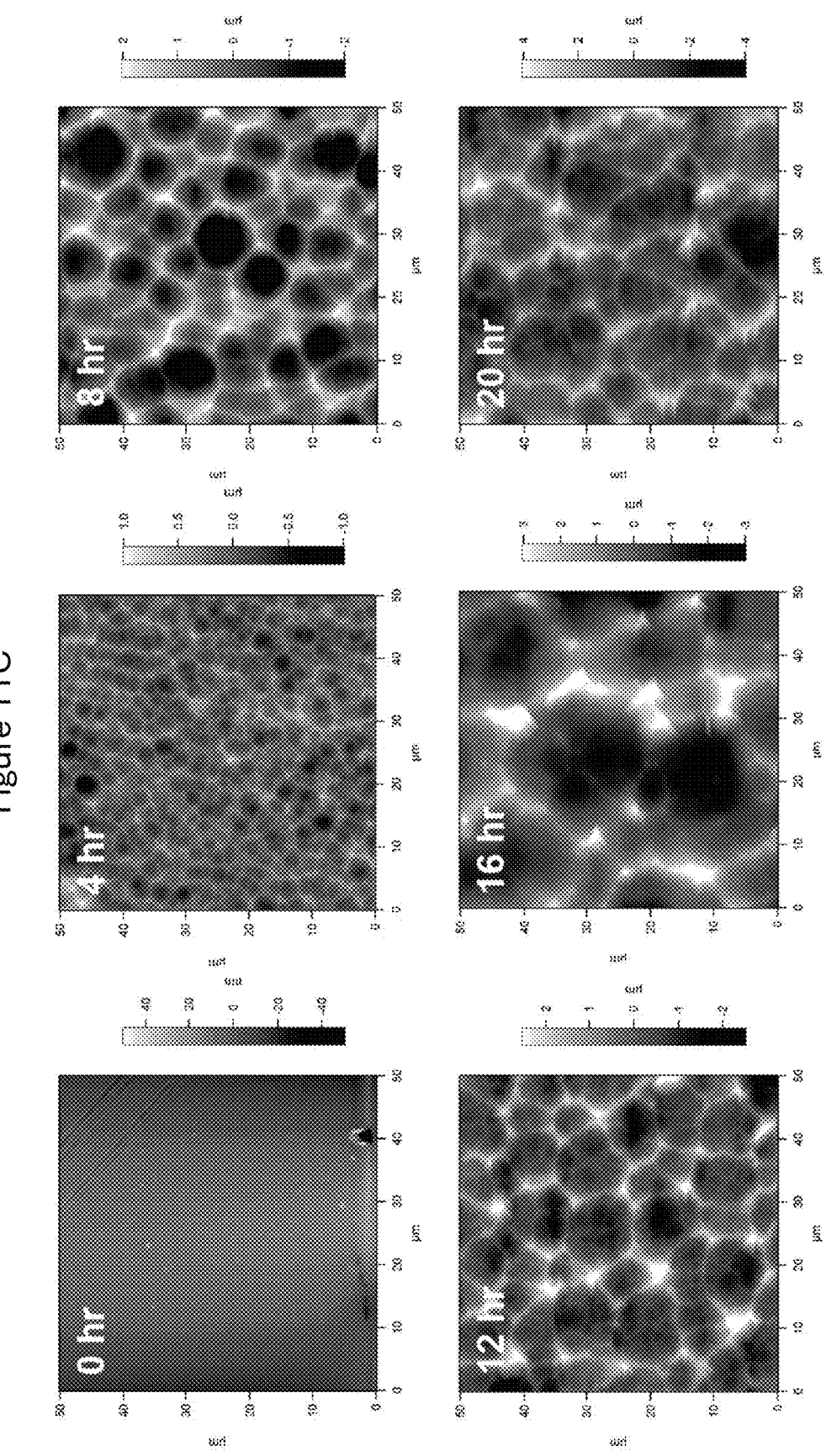
Figure 11D:
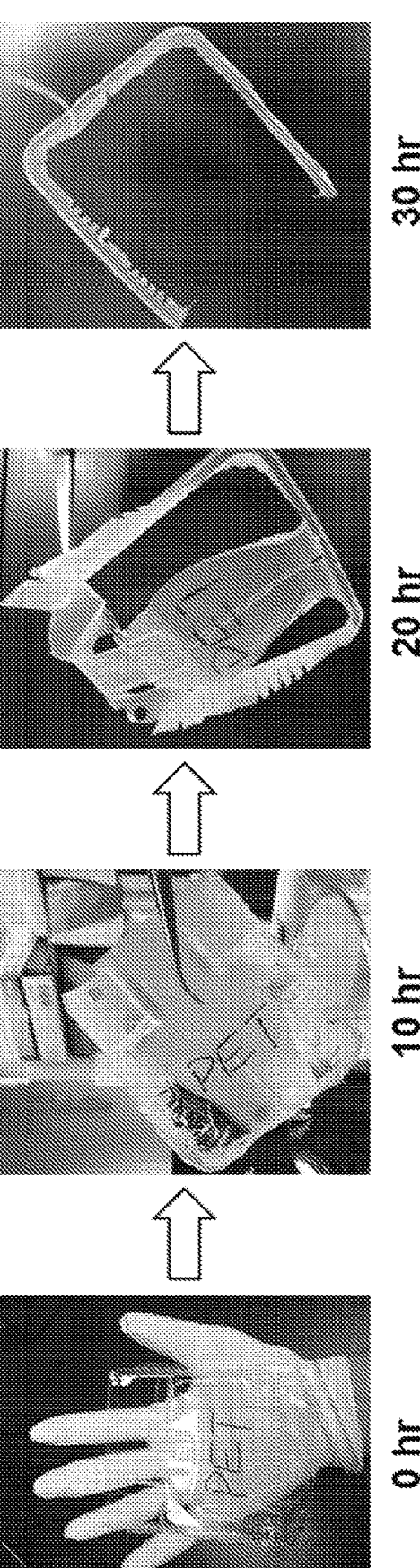

Among the post-consumer products tested above, we further evaluated the sample from a Bean cake container that was completely degraded by αPETase within 24 hrs at 50° C. A time-course analysis (FIG. 11b) revealed that the degradation of this pc-PET film exhibited an almost linear decay rate using αPETase in terms of the total PET monomers released. Concomitantly, degradation of the pc-PET film by αPETase brought an increase in the crystallinity from 1.2% to 7.7% over 24 hrs. Atomic Force Microscopy (FIG. 11c) as well as Scanning Electron Microscopy further showed that the reaction progression of αPETase as it produced increasingly deeper and larger holes in the pc-PET surface resulting in increased surface roughness over reaction time. In contrast, the PET-hydrolytic activity of wild-type PETase, ThermoPETase, DuraPETase, βPETase, LCC and ICCM toward this pc-PET was substantially lower (4.2 to 295-fold) than that of αPETase under the same conditions (FIG. 11b). Interestingly, even at their previously reported optimal reaction temperature of 72° C. (Tournier, V. et al. An engineered PET depolymerase to break down and recycle plastic bottles. Nature (2020). doi:10.1038/s41586-020-2149-4), the activity of LCC and ICCM was still 6.3-fold and 2.7-fold lower than that of αPETase at 50° C. Further experimental analysis showed that LCC and ICCM exhibited their highest degradation rate against this pc-PET film at 60° C. However, even at 60° C., the activity of LCC and ICCM was still lower than that of αPETase at 50° C. Moreover, we demonstrate that the process with αPETase is easily scalable to large, untreated pieces of plastic (in this case, 4 g rather than 11 mg) simply by increasing net reaction volumes (FIG. 11d). Given these results, αPETase can serve as a promising biocatalyst for the enzyme-based platform aimed at recycling raw, untreated PET waste, with advantages of lower operating cost and higher degradation efficiency of post-consumer PET, in contrast to ICCM that requires a higher reaction temperature.

Figure 11E:
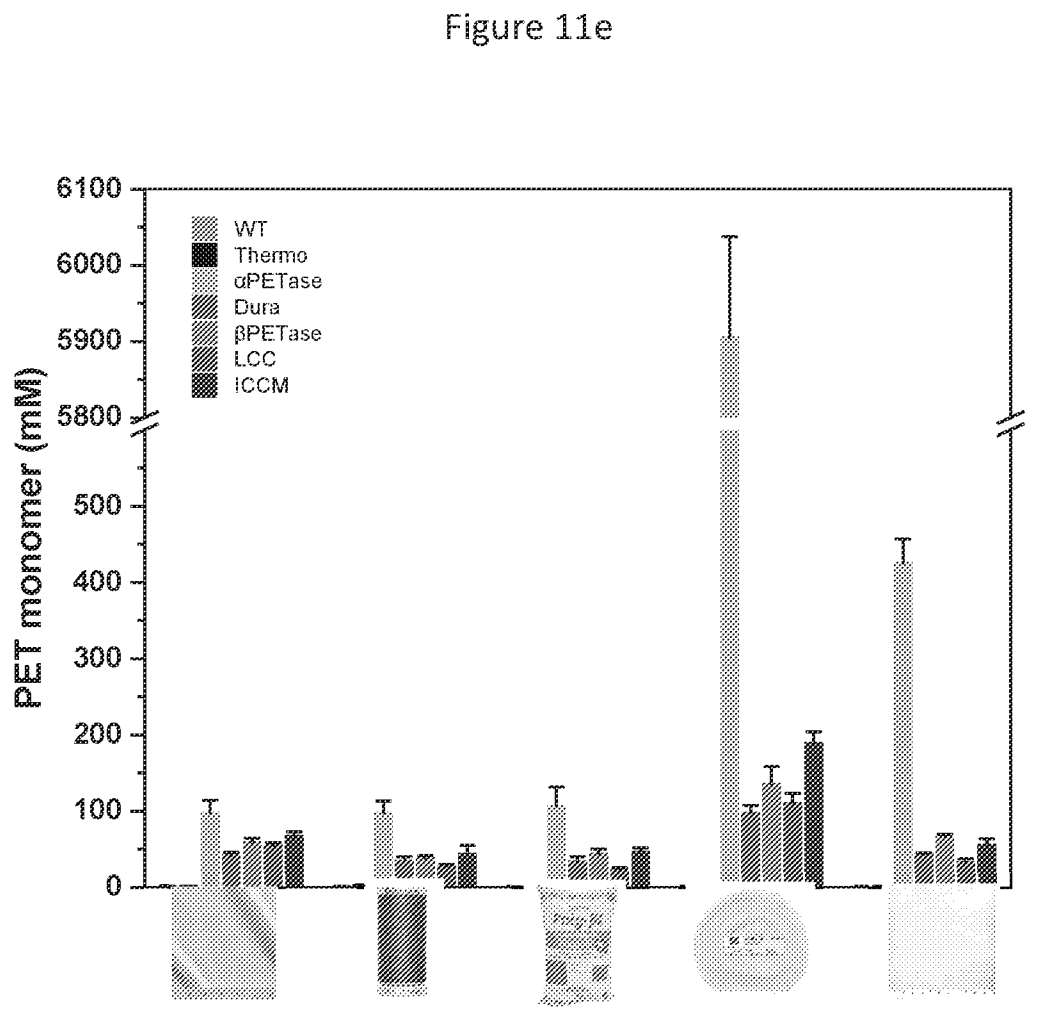

Beyond packaging materials, PET is used heavily in the synthetic textile industry. To this end, we evaluated the potential applications of αPETase to partially degrade commercial polyester products. Five different commercial polyester products were treated with αPETase at 50° C., releasing higher amounts of terephthalic acid (TPA) and Mono-(2-hydroxyethyl) terephthalate relative to that of the samples treated with other PHEs (FIG. 11e). This indicates that αPETase can potentially be used for rapid and efficient degradation of the microplastics embedded in textile fabrics, providing a potential route for recovering PET monomers from commercial polyester products and reducing the leaching of microfibers into the environment.

Figure 12A:
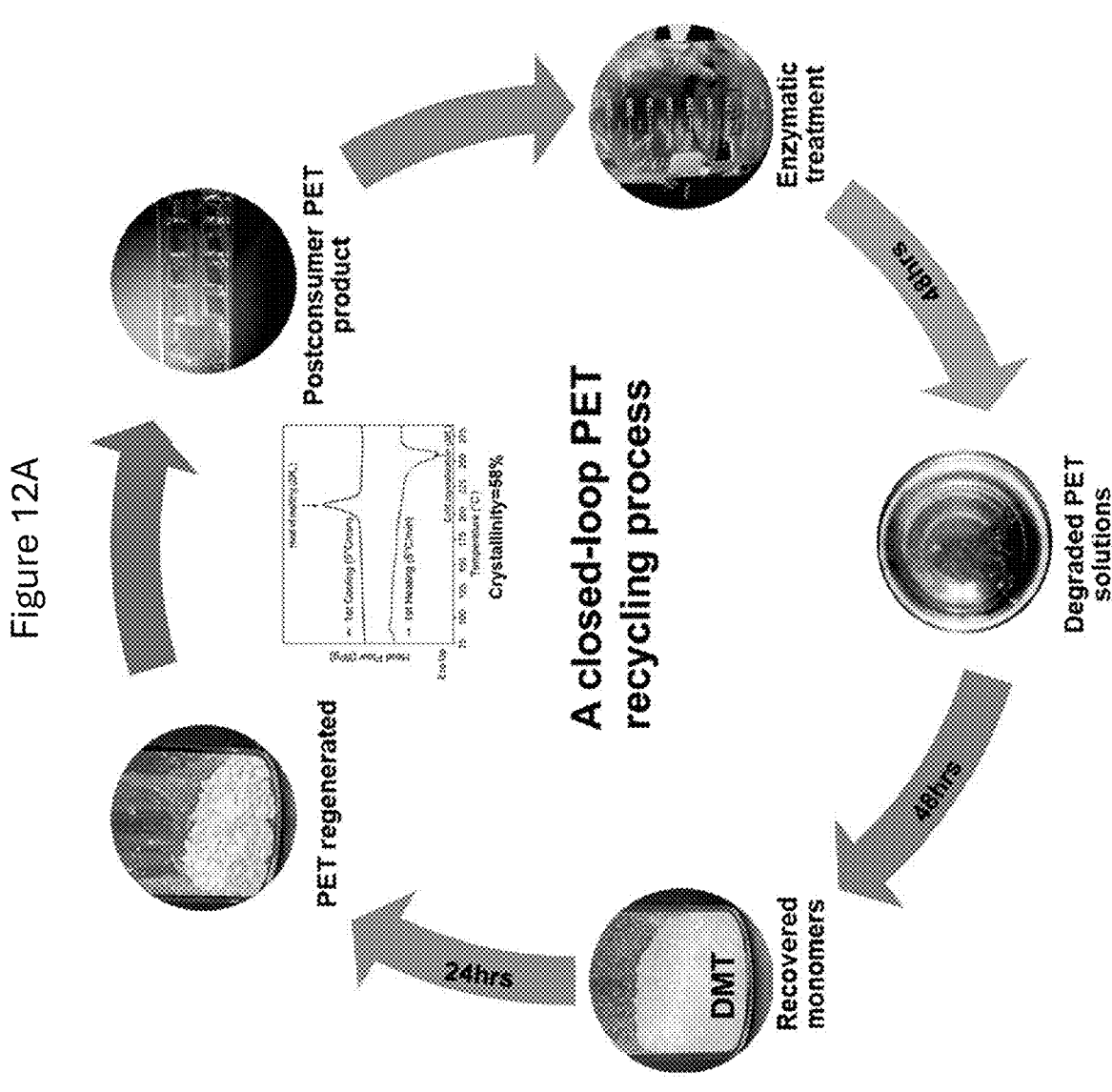
FIG. 12*a-c* Applications of αPETase in enzymatic-chemical recycling of PET and in situ bioremediation. 12*a*. Schematic of the closed-loop PET recycling process incorporating post-consumer plastic waste depolymerization by αPETase and chemical polymerization. The crystallinity of the regenerated virgin PET was determined as 58% by Differential Scanning calorimetry. 12*b*. Simultaneous process combining *P. putida* Go19 and exogenous PHEs: αPETase, wild-type PETase (WT), ThermoPETase (Thermo), DuraPETase (Dura), βPETase, LCC and ICCM. PHE (αPETase/WT/Thermo/Dura/βPETase/LCC/ICCM) & GO19 represents the simultaneous process of a PHE with *P. putida* Go 19, whereas PHE represents the control condition where the enzyme is presented without *P. putida* Go 19. Liberated PET monomers, mass loss of the pc-PET films, and cell density of *P. putida* Go19 were measured after 96 hrs of incubation. All measurements were conducted in triplicate (n=3). 12*c*. Consolidated process of the engineered *P. putida* Go19 strain that is capable of secreting αPETase/WT/Thermo/Dura/βPETase. Liberated PET monomers, mass loss of the pc-PET films, and cell density of *P. putida* Go19 were measured after 120 hrs of incubation. All measurements were conducted in triplicate (n=3).

Given the high activity of this αPETase mutant at ambient temperatures and pH conditions, we hypothesized that this enzyme would be suitable for various enzymatic-microbial and enzymatic-chemical processing of PET. In this regard, PET degradation is only half of the circular plastic economy and we demonstrate here the compatibility of αPETase with both chemical and biological recycling/upcycling applications. First, we demonstrate a closed-cycle PET re-constitution by first depolymerizing post-consumer plastic waste utilizing αPETase and subsequently recovering monomers. We then regenerate virgin PET directly from the degradation solution using chemical polymerization (FIG. 12a) The complete cycle of degradation to re-polymerization was completed over only the course of a few days. These results demonstrate the feasibility of a closed-loop enzymatic/chemical recycling process to generate virgin PET from non-petroleum resources.

Figure 12B:
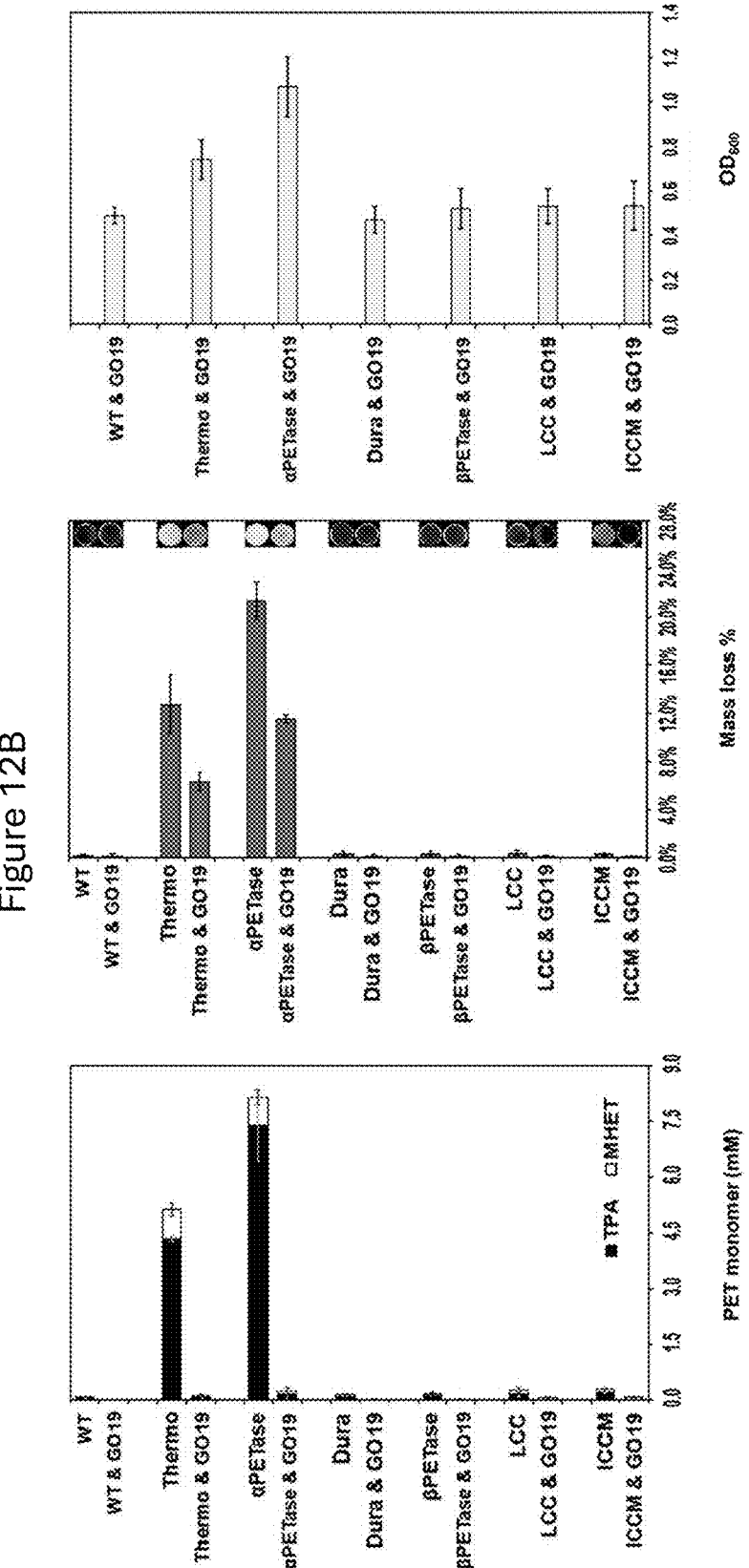

Second, we sought to utilize the degradation capability of αPETase at ambient temperature to enable direct depolymerization and microbial valorization/bioremediation of monomers. To this end, we evaluated both simultaneous and consolidated biodegradation schemes using αPETase. In particular, a soil bacteria Pseudomonas putida Go19 (Narancic, T. et al. Genome analysis of the metabolically versatile Pseudomonas umsongensis GO16: the genetic basis for PET monomer upcycling into polyhydroxyalkanoates. Microb. Biotechnol. (2021). doi:10.1111/1751-7915.13712), (Kenny, S. T. et al. Up-cycling of PET (Polyethylene Terephthalate) to the biodegradable plastic PHA (Polyhydroxyalkanoate). Environ. Sci. Technol. (2008). doi:10.1021/es801010e) capable of naturally utilizing TPA as a carbon and energy source was employed. Initially, we sought to combine exogenous αPETase with this host to explore the possibility of simultaneous PET depolymerization and fermentation. P. putida Go19 was inoculated into a minimal medium supplemented with an unpretreated pc-PET film absent of any other carbon source. Upon adding 200 mM of purified αPETase to the culture medium and incubation at 35° C., growth of P. putida Go19 was observed concomitant with the degraded pc-PET film which displayed opacity and lost 11.5±0.3% of its initial weight (FIG. 12b). Through this experiment, we observed that the TPA liberated from the hydrolysis of pc-PET film by αPETase was consumed by the P. putida Go19 for growth (FIG. 12b). In contrast, when wild-type PETase, ThermoPETase, DuraPETase, βPETase, LCC, or ICCM was used as the catalyst in such process, the cell density of P. putida Go 19 and the weight loss of the pc-PET film were all significantly lower than when αPETase was used (FIG. 12b). These results demonstrated that αPETase exhibited the highest PET-hydrolytic activity under cell-growth compatible conditions when compared with other PHEs tested.

Figure 12C:
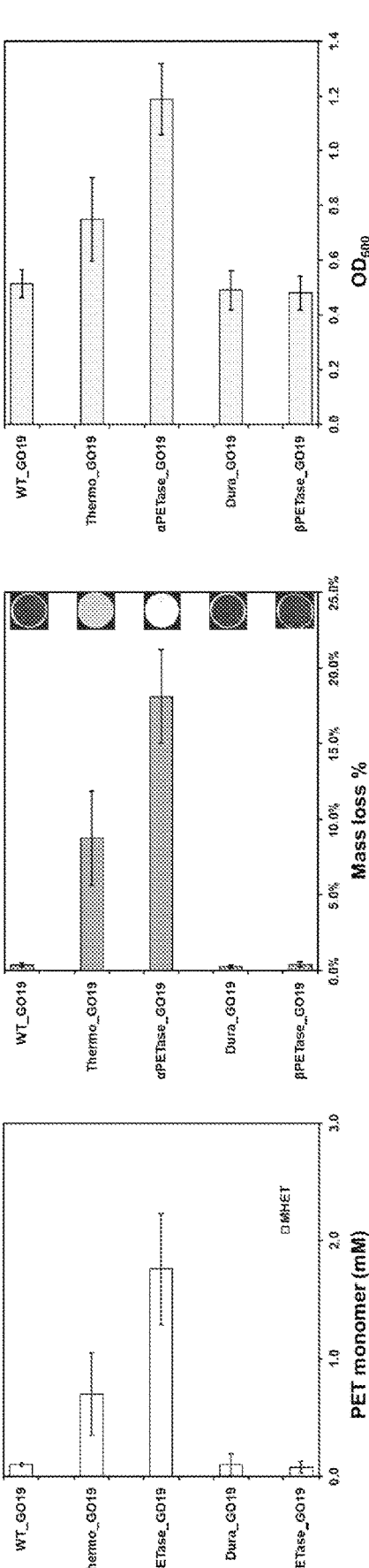

Finally, we sought to develop a consolidated bioprocess by incorporating αPETase expression into the P. putida Go 19 to enable conversion of pc-PET to biomass. To do so, we engineered P. putida Go 19 to efficiently secrete αPETase at a high yield of 30 mg/L. After priming the consolidated process with some TPA, a pc-PET film was provided to the engineered strain as the sole carbon source. After 96 hrs of incubation at 35° C., P. putida Go 19 partially degraded the pc-PET film as evidenced by film opacity and a weight loss of 18.1±3.1%. Likewise, the liberated monomer was directly valorized into cell growth (FIG. 12c). This demonstration represents the first consolidated bioprocess that integrates enzyme production to perform on-site PET depolymerization and TPA conversion to biomass at ambient temperatures and neutral pH.

In conclusion, this work utilized a structure-based deep learning model to identify portable mutations that impart improved stability and function across a variety of PETase scaffolds. The best variant, αPETase, exhibits predominant activity over a wide range of temperatures (30-50° C.) and exceptional compatibility with cell-growth conditions. We demonstrate this capacity via the rapid and efficient degradation of bulk, untreated post-consumer PET waste and reduction of microplastics embedded in textile fabrics. The properties of this mutant are suitable for both low-cost industrial recycling as well as in situ plastic bioremediation applications as demonstrated by both simultaneous and consolidated bioprocesses using P. putida Go 19. Collectively, these results demonstrate the impact structure-based deep learning could have in protein engineering and the utility of a mesophilic enzyme to be evolved into a broad-range biocatalyst for direct plastic depolymerization.

SEQUENCES

SEQ ID NO: 1
LENGTH: 290
OTHER INFORMATION: Wild type IsPETase
SEQUENCE: 1

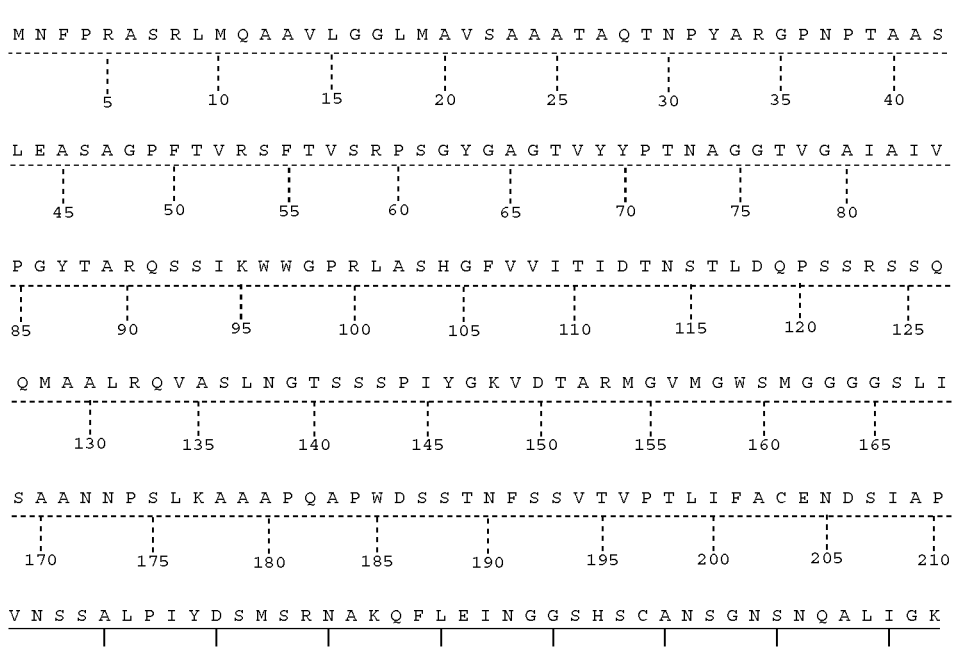

```
M N F P R A S R L M Q A A V L G G L M A V S A A A T A Q T N P Y A R G P N P T A A S
            5         10        15        20        25        30        35        40

L E A S A G P F T V R S F T V S R P S G Y G A G T V Y Y P T N A G G T V G A I A I V
          45        50        55        60        65        70        75        80

P G Y T A R Q S S I K W W G P R L A S H G F V V I T I D T N S T L D Q P S S R S S Q
85        90        95        100       105       110       115       120       125

Q M A A L R Q V A S L N G T S S S P I Y G K V D T A R M G V M G W S M G G G G S L I
          130       135       140       145       150       155       160       165

S A A N P S L K A A A P Q A P W D S S T N F S S V T V P T L I F A C E N D S I A P
    170       175       180       185       190       195       200       205       210

V N S S A L P I Y D S M S R N A K Q F L E I N G G S H S C A N S G N S N Q A L I G K
        215       220       225       230       235       240       245       250

K G V A W M K R F M D N D T R Y S T F A C E N P N S T R V S D F R T A N C S
    255       260       265       270       275       280       285       290
```

SEQ ID NO: 2
LENGTH: 290
OTHER INFORMATION: ThermoPETase (IsPETase$^{S121E/D186H/R280A}$)
SEQUENCE: 2

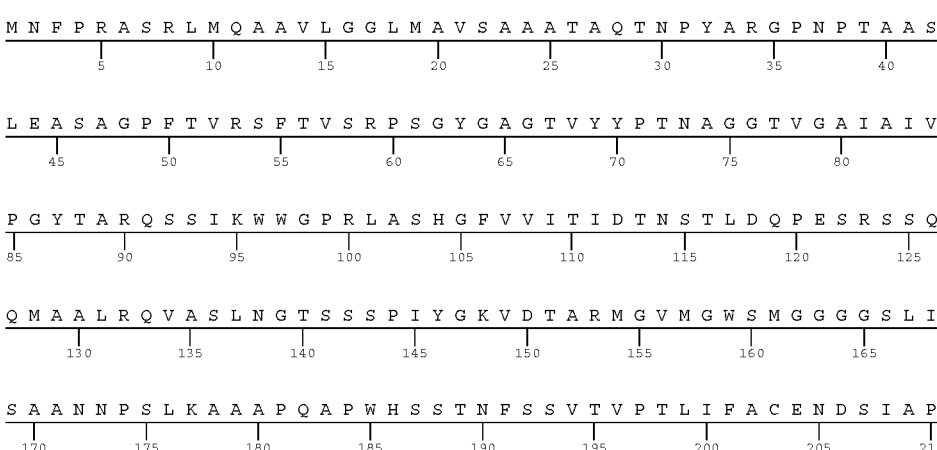

```
M N F P R A S R L M Q A A V L G G L M A V S A A A T A Q T N P Y A R G P N P T A A S
            5         10        15        20        25        30        35        40

L E A S A G P F T V R S F T V S R P S G Y G A G T V Y Y P T N A G G T V G A I A I V
          45        50        55        60        65        70        75        80

P G Y T A R Q S S I K W W G P R L A S H G F V V I T I D T N S T L D Q P E S R S S Q
85        90        95        100       105       110       115       120       125

Q M A A L R Q V A S L N G T S S S P I Y G K V D T A R M G V M G W S M G G G G S L I
      130       135       140       145       150       155       160       165
```

```
S A A N P S L K A A A P Q A P W H S S T N F S S V T V P T L I F A C E N D S I A P
    170       175       180       185       190       195       200       205       210

V N S S A L P I Y D S M S R N A K Q F L E I N G G S H S C A N S G N S N Q A L I G K
        215       220       225       230       235       240       245       250
```

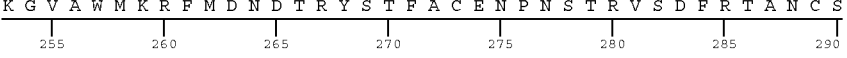

```
K G V A W M K R F M D N D T R Y S T F A C E N P N S T R V S D F R T A N C S
    255       260       265       270       275       280       285       290
```

-continued

SEQUENCES

SEQ ID NO: 3
LENGTH: 290
OTHER INFORMATION: DuraPETase (IsPETase$^{L117F/Q119Y/T140D/W159H,G165A/I168R/A180I/S188Q/S214H/R280A}$)
SEQUENCE: 3

```
M N F P R A S R L M Q A A V L G G L M A V S A A A T A Q T N P Y A R G P N P T A A S
              5         10        15        20        25        30        35        40

L E A S A G P F T V R S F T V S R P S G Y G A G T V Y Y P T N A G G T V G A I A I V
         45        50        55        60        65        70        75        80

P G Y T A R Q S S I K W W G P R L A S H G F V V I T I D T N S T L D Q P E S R S S Q
85        90        95        100       105       110       115       120       125

Q M A A L R Q V A S L N G D S S S P I Y G K V D T A R M G V M G H S M G G G A S L R
         130       135       140       145       150       155       160       165

S A A N N P S L K A A I P Q A P W D S Q T N F S S V T V P T L I F A C E N D S I A P
  170       175       180       185       190       195       200       205       210

V N S H A L P I Y D S M S R N A K Q F L E I N G G S H S C A N S G N S N Q A L I G K
         215       220       225       230       235       240       245       250

K G V A W M K R F M D N D T R Y S T F A C E N P N S T A V S D F R T A N C S
     255       260       265       270       275       280       285       290
```

SEQ ID NO: 4
LENGTH: 290
OTHER INFORMATION: ThermoPETase (IsPETase$^{S121E/D186H/R280A/N233K}$)
SEQUENCE: 4

```
M N F P R A S R L M Q A A V L G G L M A V S A A A T A Q T N P Y A R G P N P T A A S
              5         10        15        20        25        30        35        40

L E A S A G P F T V R S F T V S R P S G Y G A G T V Y Y P T N A G G T V G A I A I V
         45        50        55        60        65        70        75        80

P G Y T A R Q S S I K W W G P R L A S H G F V V I T I D T N S T L D Q P E S R S S Q
85        90        95        100       105       110       115       120       125

Q M A A L R Q V A S L N G T S S S P I Y G K V D T A R M G V M G W S M G G G G S L I
         130       135       140       145       150       155       160       165

S A A N N P S L K A A A P Q A P W H S S T N F S S V T V P T L I F A C E N D S I A P
  170       175       180       185       190       195       200       205       210

V N S S A L P I Y D S M S R N A K Q F L E I K G G S H S C A N S G N S N Q A L I G K
         215       220       225       230       235       240       245       250

K G V A W M K R F M D N D T R Y S T F A C E N P N S T A V S D F R T A N C S
     255       260       265       270       275       280       285       290
```

-continued

---
SEQUENCES
---

SEQ ID NO: 5
LENGTH: 290
OTHER INFORMATION: WT NET
SEQUENCE: 5

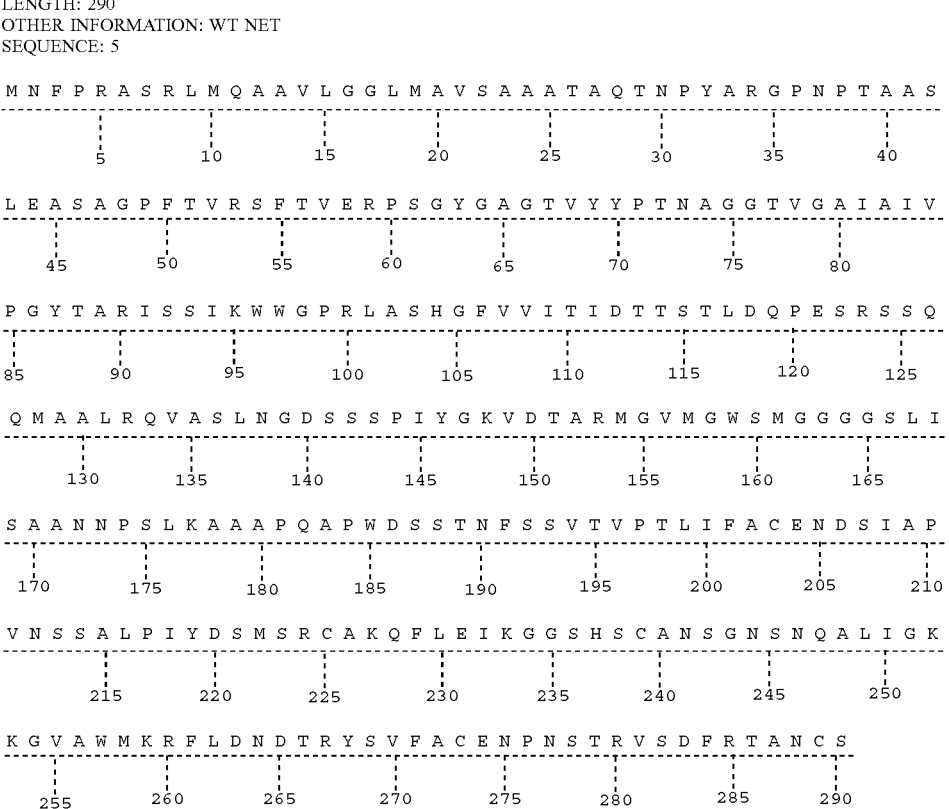

```
M N F P R A S R L M Q A A V L G G L M A V S A A A T A Q T N P Y A R G P N P T A A S
          5         10        15        20        25        30        35        40

L E A S A G P F T V R S F T V E R P S G Y G A G T V Y Y P T N A G G T V G A I A I V
          45        50        55        60        65        70        75        80

P G Y T A R I S S I K W W G P R L A S H G F V V I T I D T T S T L D Q P E S R S S Q
 85        90        95        100       105       110       115       120       125

Q M A A L R Q V A S L N G D S S S P I Y G K V D T A R M G V M G W S M G G G G S L I
          130       135       140       145       150       155       160       165

S A A N N P S L K A A A P Q A P W D S S T N F S S V T V P T L I F A C E N D S I A P
   170       175       180       185       190       195       200       205       210

V N S S A L P I Y D S M S R C A K Q F L E I K G G S H S C A N S G N S N Q A L I G K
          215       220       225       230       235       240       245       250

K G V A W M K R F L D N D T R Y S V F A C E N P N S T R V S D F R T A N C S
   255       260       265       270       275       280       285       290
```

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

---

What is claimed is:

1. An engineered PET (poly(ethylene terephthalate)) hydrolase comprising an amino acid sequence at least 90% identical to SEQ ID NO:1 and having at least one mutation corresponding to N233 relative to SEQ ID NO:1.

2. The engineered PET hydrolase of claim 1, wherein the at least one mutation is N233K.

3. The engineered PET hydrolase of claim 1, wherein the amino acid sequence is at least 95% identical to SEQ ID NO: 1, 2 or 3.

4. The engineered PET hydrolase of claim 1, wherein the amino acid sequence is identical to SEQ ID NO: 1, 2 or 3 except for the at least one mutation.

5. The engineered PET hydrolase of claim 1, wherein the amino acid sequence has at least two mutations corresponding to a position relative to SEQ ID NO: 1 selected from the group consisting of N233K, S58E, S58A, N114T, S121E, N225C, M262L, T270V, T140D, S61T, I208V, and R224Q.

6. The engineered PET hydrolase of claim 1, wherein the amino acid sequence has two or three mutations corresponding to a position relative to SEQ ID NO: 1 selected from the group consisting of N233K, S58E, S58A, N114T, S121E, N225C, M262L, T270V, T140D, S61T, I208V, R224Q, S58Y, S58M, S58L, S58V, S58P, S61D, S61E, S61Y, S61F, N114H, N114L, N114R, N114S, N114T, T140Y, T140L, T140I, T140V, T140S, S121E, I208M, I208H, I208F, I208Y, I208P, I208A, R224D, R224E, R224S, R224T, R224N, R224Q, N225N, N225I, N225V, N225M, N225A, N225L, N225S, N225T, N233R, N233Y, N233H, N233P, M262L, M262I, M262A, M262V, M262F, M262W, T270Y, T270R, and T270H.

7. A polynucleotide encoding the engineered PET hydrolase of claim 1.

8. The polynucleotide of claim 7, wherein the engineered PET hydrolase further comprises a signal peptide.

9. A vector comprising a promoter operably linked to the polynucleotide of claim 7 such that the promoter controls expression of the engineered PET hydrolase.

10. A host cell comprising the polynucleotide of claim 7.

11. The host cell of claim 10, wherein the host cell is a microbial cell.

12. The host cell of claim 10, wherein the host cell is a bacterial cell.

13. The host cell of claim 12, wherein the bacterial cell is *Pseudomonas putida*.

14. The host cell of claim 10, wherein the host cell is a fungal cell.

15. A method of degrading poly(ethylene terephthalate) (PET) comprising contacting PET with the engineered PET hydrolase of claim 1 under conditions to degrade the PET.

16. The method of claim 15, comprising contacting the PET with a host cell that expresses and secretes the engineered PET hydrolase.

17. The method of claim 15, wherein the engineered PET hydrolase is purified.

18. The method of claim 15, wherein the conditions include an incubation at a temperature of between 25-70° C.

* * * * *

SEQUENCE LISTING

<160> NUMBER OF SEQ ID NOS: 37

<210> SEQ ID NO 1
<211> LENGTH: 290
<212> TYPE: PRT
<213> ORGANISM: Ideonella sakaiensis

<400> SEQUENCE: 1

Met Asn Phe Pro Arg Ala Ser Arg Leu Met Gln Ala Ala Val Leu Gly
1               5                   10                  15

Gly Leu Met Ala Val Ser Ala Ala Ala Thr Ala Gln Thr Asn Pro Tyr
            20                  25                  30

Ala Arg Gly Pro Asn Pro Thr Ala Ala Ser Leu Glu Ala Ser Ala Gly
        35                  40                  45

Pro Phe Thr Val Arg Ser Phe Thr Val Ser Arg Pro Ser Gly Tyr Gly
    50                  55                  60

Ala Gly Thr Val Tyr Tyr Pro Thr Asn Ala Gly Gly Thr Val Gly Ala
65                  70                  75                  80

-continued

```
Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Leu Asp Gln Pro Ser Ser Arg Ser Ser Gln Gln Met
        115                 120                 125

Ala Ala Leu Arg Gln Val Ala Ser Leu Asn Gly Thr Ser Ser Ser Pro
    130                 135                 140

Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                165                 170                 175

Lys Ala Ala Ala Pro Gln Ala Pro Trp Asp Ser Ser Thr Asn Phe Ser
            180                 185                 190

Ser Val Thr Val Pro Thr Leu Ile Phe Ala Cys Glu Asn Asp Ser Ile
        195                 200                 205

Ala Pro Val Asn Ser Ser Ala Leu Pro Ile Tyr Asp Ser Met Ser Arg
    210                 215                 220

Asn Ala Lys Gln Phe Leu Glu Ile Asn Gly Gly Ser His Ser Cys Ala
225                 230                 235                 240

Asn Ser Gly Asn Ser Asn Gln Ala Leu Ile Gly Lys Lys Gly Val Ala
                245                 250                 255

Trp Met Lys Arg Phe Met Asp Asn Asp Thr Arg Tyr Ser Thr Phe Ala
            260                 265                 270

Cys Glu Asn Pro Asn Ser Thr Arg Val Ser Asp Phe Arg Thr Ala Asn
        275                 280                 285

Cys Ser
    290
```

<210> SEQ ID NO 2
<211> LENGTH: 290
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 2

```
Met Asn Phe Pro Arg Ala Ser Arg Leu Met Gln Ala Ala Val Leu Gly
1               5                   10                  15

Gly Leu Met Ala Val Ser Ala Ala Ala Thr Ala Gln Thr Asn Pro Tyr
            20                  25                  30

Ala Arg Gly Pro Asn Pro Thr Ala Ala Ser Leu Glu Ala Ser Ala Gly
        35                  40                  45

Pro Phe Thr Val Arg Ser Phe Thr Val Ser Arg Pro Ser Gly Tyr Gly
    50                  55                  60

Ala Gly Thr Val Tyr Tyr Pro Thr Asn Ala Gly Gly Thr Val Gly Ala
65                  70                  75                  80

Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Leu Asp Gln Pro Glu Ser Arg Ser Ser Gln Gln Met
        115                 120                 125

Ala Ala Leu Arg Gln Val Ala Ser Leu Asn Gly Thr Ser Ser Ser Pro
```

-continued

```
        130                   135                   140

Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                    165                 170                 175

Lys Ala Ala Ala Pro Gln Ala Pro Trp His Ser Ser Thr Asn Phe Ser
                180                 185                 190

Ser Val Thr Val Pro Thr Leu Ile Phe Ala Cys Glu Asn Asp Ser Ile
            195                 200                 205

Ala Pro Val Asn Ser Ser Ala Leu Pro Ile Tyr Asp Ser Met Ser Arg
            210                 215                 220

Asn Ala Lys Gln Phe Leu Glu Ile Asn Gly Gly Ser His Ser Cys Ala
225                 230                 235                 240

Asn Ser Gly Asn Ser Asn Gln Ala Leu Ile Gly Lys Lys Gly Val Ala
                245                 250                 255

Trp Met Lys Arg Phe Met Asp Asn Asp Thr Arg Tyr Ser Thr Phe Ala
                260                 265                 270

Cys Glu Asn Pro Asn Ser Thr Ala Val Ser Asp Phe Arg Thr Ala Asn
            275                 280                 285

Cys Ser
    290

<210> SEQ ID NO 3
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asn Phe Pro Arg Ala Ser Arg Leu Met Gln Ala Ala Val Leu Gly
1                 5                   10                  15

Gly Leu Met Ala Val Ser Ala Ala Ala Thr Ala Gln Thr Asn Pro Tyr
                20                  25                  30

Ala Arg Gly Pro Asn Pro Thr Ala Ala Ser Leu Glu Ala Ser Ala Gly
            35                  40                  45

Pro Phe Thr Val Arg Ser Phe Thr Val Ser Arg Pro Ser Gly Tyr Gly
    50                  55                  60

Ala Gly Thr Val Tyr Tyr Pro Thr Asn Ala Gly Gly Thr Val Gly Ala
65                  70                  75                  80

Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Phe Asp Tyr Pro Ser Ser Arg Ser Ser Gln Gln Met
            115                 120                 125

Ala Ala Leu Arg Gln Val Ala Ser Leu Asn Gly Asp Ser Ser Ser Pro
        130                 135                 140

Ile Tyr Gly Lys Val Asp Thr Ala Arg Met Gly Val Met Gly His Ser
145                 150                 155                 160

Met Gly Gly Gly Ala Ser Leu Arg Ser Ala Ala Asn Asn Pro Ser Leu
                165                 170                 175

Lys Ala Ala Ile Pro Gln Ala Pro Trp Asp Ser Gln Thr Asn Phe Ser
                180                 185                 190
```

```
Ser Val Thr Val Pro Thr Leu Ile Phe Ala Cys Glu Asn Asp Ser Ile
        195                 200                 205

Ala Pro Val Asn Ser His Ala Leu Pro Ile Tyr Asp Ser Met Ser Arg
    210                 215                 220

Asn Ala Lys Gln Phe Leu Glu Ile Asn Gly Gly Ser His Ser Cys Ala
225                 230                 235                 240

Asn Ser Gly Asn Ser Asn Gln Ala Leu Ile Gly Lys Lys Gly Val Ala
                245                 250                 255

Trp Met Lys Arg Phe Met Asp Asn Asp Thr Arg Tyr Ser Thr Phe Ala
            260                 265                 270

Cys Glu Asn Pro Asn Ser Thr Ala Val Ser Asp Phe Arg Thr Ala Asn
            275                 280                 285

Cys Ser
    290
```

```
<210> SEQ ID NO 4
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

```
Met Asn Phe Pro Arg Ala Ser Arg Leu Met Gln Ala Ala Val Leu Gly
1                 5                   10                  15

Gly Leu Met Ala Val Ser Ala Ala Ala Thr Ala Gln Thr Asn Pro Tyr
            20                  25                  30

Ala Arg Gly Pro Asn Pro Thr Ala Ala Ser Leu Glu Ala Ser Ala Gly
            35                  40                  45

Pro Phe Thr Val Arg Ser Phe Thr Val Ser Arg Pro Ser Gly Tyr Gly
    50                  55                  60

Ala Gly Thr Val Tyr Tyr Pro Thr Asn Ala Gly Gly Thr Val Gly Ala
65                  70                  75                  80

Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Leu Asp Gln Pro Glu Ser Arg Ser Ser Gln Gln Met
            115                 120                 125

Ala Ala Leu Arg Gln Val Ala Ser Leu Asn Gly Thr Ser Ser Ser Pro
    130                 135                 140

Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                165                 170                 175

Lys Ala Ala Ala Pro Gln Ala Pro Trp His Ser Ser Thr Asn Phe Ser
            180                 185                 190

Ser Val Thr Val Pro Thr Leu Ile Phe Ala Cys Glu Asn Asp Ser Ile
        195                 200                 205

Ala Pro Val Asn Ser Ser Ala Leu Pro Ile Tyr Asp Ser Met Ser Arg
    210                 215                 220

Asn Ala Lys Gln Phe Leu Glu Ile Lys Gly Gly Ser His Ser Cys Ala
225                 230                 235                 240

Asn Ser Gly Asn Ser Asn Gln Ala Leu Ile Gly Lys Lys Gly Val Ala
                245                 250                 255
```

-continued

```
Trp Met Lys Arg Phe Met Asp Asn Asp Thr Arg Tyr Ser Thr Phe Ala
            260             265             270

Cys Glu Asn Pro Asn Ser Thr Ala Val Ser Asp Phe Arg Thr Ala Asn
        275             280             285

Cys Ser
    290

<210> SEQ ID NO 5
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asn Phe Pro Arg Ala Ser Arg Leu Met Gln Ala Ala Val Leu Gly
1               5               10              15

Gly Leu Met Ala Val Ser Ala Ala Ala Thr Ala Gln Thr Asn Pro Tyr
            20              25              30

Ala Arg Gly Pro Asn Pro Thr Ala Ala Ser Leu Glu Ala Ser Ala Gly
        35              40              45

Pro Phe Thr Val Arg Ser Phe Thr Val Glu Arg Pro Ser Gly Tyr Gly
    50              55              60

Ala Gly Asp Val Tyr Tyr Pro Thr Asn Ala Gly Gly Thr Val Gly Ala
65              70              75              80

Ile Ala Ile Val Pro Gly Tyr Thr Ala Arg Ile Ser Ser Ile Lys Trp
                85              90              95

Trp Gly Pro Arg Leu Ala Ser His Gly Phe Val Val Ile Thr Ile Asp
            100             105             110

Thr Thr Ser Thr Leu Asp Gln Pro Glu Ser Arg Ser Ser Gln Gln Met
        115             120             125

Ala Ala Leu Arg Gln Val Ala Ser Leu Asn Gly Asp Ser Ser Ser Pro
    130             135             140

Ile Tyr Gly Lys Val Asp Thr Ala Arg Met Gly Val Met Gly Trp Ser
145             150             155             160

Met Gly Gly Gly Gly Ser Leu Ile Ser Ala Ala Asn Asn Pro Ser Leu
            165             170             175

Lys Ala Ala Ala Pro Gln Ala Pro Trp Asp Ser Ser Thr Asn Phe Ser
        180             185             190

Ser Val Thr Val Pro Thr Leu Ile Phe Ala Cys Glu Asn Asp Ser Ile
        195             200             205

Ala Pro Val Asn Ser Ser Ala Leu Pro Ile Tyr Asp Ser Met Ser Arg
    210             215             220

Cys Ala Lys Gln Phe Leu Glu Ile Lys Gly Gly Ser His Ser Cys Ala
225             230             235             240

Asn Ser Gly Asn Ser Asn Gln Ala Leu Ile Gly Lys Lys Gly Val Ala
            245             250             255

Trp Met Lys Arg Phe Leu Asp Asn Asp Thr Arg Tyr Ser Val Phe Ala
            260             265             270

Cys Glu Asn Pro Asn Ser Thr Arg Val Ser Asp Phe Arg Thr Ala Asn
        275             280             285

Cys Ser
    290
```

-continued

```
<210> SEQ ID NO 6
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
        50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Ser Ser Arg
                    85                  90                  95

Ser Ser Gln Gln Met Ala Ala Leu Arg Gln Val Ala Ser Leu Asn Gly
                100                 105                 110

Thr Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
        130                 135                 140

Asn Asn Pro Ser Leu Lys Ala Ala Ala Pro Gln Ala Pro Trp Asp Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
                180                 185                 190

Asp Ser Met Ser Arg Asn Ala Lys Gln Phe Leu Glu Ile Lys Gly Gly
            195                 200                 205

Ser His Ser Cys Ala Asn Ser Gly Asn Ser Asn Gln Ala Leu Ile Gly
        210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
                245                 250                 255

Phe Arg Thr Ala Asn Cys Ser
            260

<210> SEQ ID NO 7
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
```

-continued

```
            35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
                100                 105                 110

Thr Ser Ser Ser Pro Ile Tyr Gly Lys Val Asp Thr Ala Arg Met Gly
                115                 120                 125

Val Met Gly Trp Ser Met Gly Gly Gly Ser Leu Ile Ser Ala Ala
    130                 135                 140

Asn Asn Pro Ser Leu Lys Ala Ala Ala Pro Gln Ala Pro Trp Asp Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
                180                 185                 190

Asp Ser Met Ser Arg Asn Ala Lys Gln Phe Leu Glu Ile Asn Gly Gly
                195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
                245                 250                 255

Phe Arg Thr Ala Asn Cys Ser
                260

<210> SEQ ID NO 8
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Ser Ser Arg
                85                  90                  95

Ser Ser Gln Gln Met Ala Ala Leu Arg Gln Val Ala Ser Leu Asn Gly
                100                 105                 110

Asp Ser Ser Ser Pro Ile Tyr Gly Lys Val Asp Thr Ala Arg Met Gly
            115                 120                 125
```

```
Val Met Gly Trp Ser Met Gly Gly Gly Ser Leu Ile Ser Ala Ala
    130             135             140

Asn Asn Pro Ser Leu Lys Ala Ala Ala Pro Gln Ala Pro Trp Asp Ser
145             150             155             160

Ser Thr Asn Phe Ser Ser Val Thr Val Pro Thr Leu Ile Phe Ala Cys
                165             170             175

Glu Asn Asp Ser Ile Ala Pro Val Asn Ser Ser Ala Leu Pro Ile Tyr
            180             185             190

Asp Ser Met Ser Arg Asn Ala Lys Gln Phe Leu Glu Ile Asn Gly Gly
        195             200             205

Ser His Ser Cys Ala Asn Ser Gly Asn Ser Asn Gln Ala Leu Ile Gly
    210             215             220

Lys Lys Gly Val Ala Trp Met Lys Arg Phe Met Asp Asn Asp Thr Arg
225             230             235             240

Tyr Ser Thr Phe Ala Cys Glu Asn Pro Asn Ser Thr Arg Val Ser Asp
            245             250             255

Phe Arg Thr Ala Asn Cys Ser
            260
```

<210> SEQ ID NO 9
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gln Thr Asn Pro Tyr Ala Arg Gly Pro Asn Pro Thr Ala Ala Ser Leu
1               5               10              15

Glu Ala Ser Ala Gly Pro Phe Thr Val Arg Ser Phe Thr Val Ser Arg
            20              25              30

Pro Ser Gly Tyr Gly Ala Gly Thr Val Tyr Tyr Pro Thr Asn Ala Gly
        35              40              45

Gly Thr Val Gly Ala Ile Ala Ile Val Pro Gly Tyr Thr Ala Arg Gln
    50              55              60

Ser Ser Ile Lys Trp Trp Gly Pro Arg Leu Ala Ser His Gly Phe Val
65              70              75              80

Val Ile Thr Ile Asp Thr Asn Ser Thr Leu Asp Gln Pro Ser Ser Arg
                85              90              95

Ser Ser Gln Gln Met Ala Ala Leu Arg Gln Val Ala Ser Leu Asn Gly
            100             105             110

Thr Ser Ser Ser Pro Ile Tyr Gly Lys Val Asp Thr Ala Arg Met Gly
        115             120             125

Val Met Gly Trp Ser Met Gly Gly Gly Ser Leu Ile Ser Ala Ala
    130             135             140

Asn Asn Pro Ser Leu Lys Ala Ala Ala Pro Gln Ala Pro Trp Asp Ser
145             150             155             160

Ser Thr Asn Phe Ser Ser Val Thr Val Pro Thr Leu Ile Phe Ala Cys
                165             170             175

Glu Asn Asp Ser Ile Ala Pro Val Asn Ser Ser Ala Leu Pro Ile Tyr
            180             185             190

Asp Ser Met Ser Gln Asn Ala Lys Gln Phe Leu Glu Ile Asn Gly Gly
        195             200             205

Ser His Ser Cys Ala Asn Ser Gly Asn Ser Asn Gln Ala Leu Ile Gly
    210             215             220
```

```
Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
                245                 250                 255

Phe Arg Thr Ala Asn Cys Ser
            260

<210> SEQ ID NO 10
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
        50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
            100                 105                 110

Thr Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
        130                 135                 140

Asn Asn Pro Ser Leu Lys Ala Ala Ala Pro Gln Ala Pro Trp Asp Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
            180                 185                 190

Asp Ser Met Ser Arg Asn Ala Lys Gln Phe Leu Glu Ile Lys Gly Gly
            195                 200                 205

Ser His Ser Cys Ala Asn Ser Gly Asn Ser Asn Gln Ala Leu Ile Gly
        210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
                245                 250                 255

Phe Arg Thr Ala Asn Cys Ser
            260

<210> SEQ ID NO 11
<211> LENGTH: 263
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 11

```
Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Ser Ser Arg
                85                  90                  95

Ser Ser Gln Gln Met Ala Ala Leu Arg Gln Val Ala Ser Leu Asn Gly
            100                 105                 110

Thr Ser Ser Ser Pro Ile Tyr Gly Lys Val Asp Thr Ala Arg Met Gly
        115                 120                 125

Val Met Gly Trp Ser Met Gly Gly Gly Gly Ser Leu Ile Ser Ala Ala
    130                 135                 140

Asn Asn Pro Ser Leu Lys Ala Ala Ala Pro Gln Ala Pro Trp Asp Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
            180                 185                 190

Asp Ser Met Ser Gln Asn Ala Lys Gln Phe Leu Glu Ile Lys Gly Gly
        195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
                245                 250                 255

Phe Arg Thr Ala Asn Cys Ser
            260
```

<210> SEQ ID NO 12
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
```

```
                    65                      70                      75                      80

Val Ile Thr Ile Asp Thr Asn Ser Thr Leu Asp Gln Pro Glu Ser Arg
                        85                      90                      95

Ser Ser Gln Gln Met Ala Ala Leu Arg Gln Val Ala Ser Leu Asn Gly
                    100                     105                     110

Thr Ser Ser Ser Pro Ile Tyr Gly Lys Val Asp Thr Ala Arg Met Gly
                    115                     120                     125

Val Met Gly Trp Ser Met Gly Gly Gly Gly Ser Leu Ile Ser Ala Ala
                    130                     135                     140

Asn Asn Pro Ser Leu Lys Ala Ala Ala Pro Gln Ala Pro Trp Asp Ser
145                     150                     155                     160

Ser Thr Asn Phe Ser Ser Val Thr Val Pro Thr Leu Ile Phe Ala Cys
                        165                     170                     175

Glu Asn Asp Ser Ile Ala Pro Val Asn Ser Ser Ala Leu Pro Ile Tyr
                    180                     185                     190

Asp Ser Met Ser Gln Asn Ala Lys Gln Phe Leu Glu Ile Asn Gly Gly
                    195                     200                     205

Ser His Ser Cys Ala Asn Ser Gly Asn Ser Asn Gln Ala Leu Ile Gly
                    210                     215                     220

Lys Lys Gly Val Ala Trp Met Lys Arg Phe Met Asp Asn Asp Thr Arg
225                     230                     235                     240

Tyr Ser Thr Phe Ala Cys Glu Asn Pro Asn Ser Thr Arg Val Ser Asp
                        245                     250                     255

Phe Arg Thr Ala Asn Cys Ser
                    260

<210> SEQ ID NO 13
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Thr Asn Pro Tyr Ala Arg Gly Pro Asn Pro Thr Ala Ala Ser Leu
1                   5                       10                      15

Glu Ala Ser Ala Gly Pro Phe Thr Val Arg Ser Phe Thr Val Ser Arg
                    20                      25                      30

Pro Ser Gly Tyr Gly Ala Gly Thr Val Tyr Tyr Pro Thr Asn Ala Gly
            35                      40                      45

Gly Thr Val Gly Ala Ile Ala Ile Val Pro Gly Tyr Thr Ala Arg Gln
        50                      55                      60

Ser Ser Ile Lys Trp Trp Gly Pro Arg Leu Ala Ser His Gly Phe Val
65                      70                      75                      80

Val Ile Thr Ile Asp Thr Asn Ser Thr Leu Asp Gln Pro Ser Ser Arg
                        85                      90                      95

Ser Ser Gln Gln Met Ala Ala Leu Arg Gln Val Ala Ser Leu Asn Gly
                    100                     105                     110

Asp Ser Ser Ser Pro Ile Tyr Gly Lys Val Asp Thr Ala Arg Met Gly
                    115                     120                     125

Val Met Gly Trp Ser Met Gly Gly Gly Gly Ser Leu Ile Ser Ala Ala
                    130                     135                     140

Asn Asn Pro Ser Leu Lys Ala Ala Ala Pro Gln Ala Pro Trp Asp Ser
145                     150                     155                     160
```

-continued

```
Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
            180                 185                 190

Asp Ser Met Ser Arg Asn Ala Lys Gln Phe Leu Glu Ile Lys Gly Gly
        195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
                245                 250                 255

Phe Arg Thr Ala Asn Cys Ser
                260

<210> SEQ ID NO 14
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Ser Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
        115                 120                 125

Val Met Gly Trp Ser Met Gly Gly Gly Gly Ser Leu Ile Ser Ala Ala
    130                 135                 140

Asn Asn Pro Ser Leu Lys Ala Ala Ala Pro Gln Ala Pro Trp Asp Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
            180                 185                 190

Asp Ser Met Ser Gln Asn Ala Lys Gln Phe Leu Glu Ile Asn Gly Gly
        195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
                245                 250                 255
```

-continued

```
Phe Arg Thr Ala Asn Cys Ser
        260

<210> SEQ ID NO 15
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
    130                 135                 140

Asn Asn Pro Ser Leu Lys Ala Ala Ala Pro Gln Ala Pro Trp Asp Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
            180                 185                 190

Asp Ser Met Ser Arg Asn Ala Lys Gln Phe Leu Glu Ile Asn Gly Gly
        195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
            245                 250                 255

Phe Arg Thr Ala Asn Cys Ser
        260

<210> SEQ ID NO 16
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Thr Asn Pro Tyr Ala Arg Gly Pro Asn Pro Thr Ala Ala Ser Leu
1               5                   10                  15
```

-continued

```
Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
            50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                    85                  90                  95

Ser Ser Gln Gln Met Ala Ala Leu Arg Gln Val Ala Ser Leu Asn Gly
            100                 105                 110

Thr Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
    130                 135                 140

Asn Asn Pro Ser Leu Lys Ala Ala Ala Pro Gln Ala Pro Trp Asp Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
            180                 185                 190

Asp Ser Met Ser Gln Asn Ala Lys Gln Phe Leu Glu Ile Lys Gly Gly
            195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
                245                 250                 255

Phe Arg Thr Ala Asn Cys Ser
            260
```

<210> SEQ ID NO 17
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
            50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Ser Ser Arg
                    85                  90                  95

Ser Ser Gln Gln Met Ala Ala Leu Arg Gln Val Ala Ser Leu Asn Gly
```

-continued

```
                100              105              110

Asp Ser Ser Ser Pro Ile Tyr Gly Lys Val Asp Thr Ala Arg Met Gly
         115              120              125

Val Met Gly Trp Ser Met Gly Gly Gly Gly Ser Leu Ile Ser Ala Ala
    130              135              140

Asn Asn Pro Ser Leu Lys Ala Ala Ala Pro Gln Ala Pro Trp Asp Ser
145              150              155              160

Ser Thr Asn Phe Ser Ser Val Thr Val Pro Thr Leu Ile Phe Ala Cys
              165              170              175

Glu Asn Asp Ser Ile Ala Pro Val Asn Ser Ser Ala Leu Pro Ile Tyr
         180              185              190

Asp Ser Met Ser Gln Asn Ala Lys Gln Phe Leu Glu Ile Lys Gly Gly
         195              200              205

Ser His Ser Cys Ala Asn Ser Gly Asn Ser Asn Gln Ala Leu Ile Gly
         210              215              220

Lys Lys Gly Val Ala Trp Met Lys Arg Phe Met Asp Asn Asp Thr Arg
225              230              235              240

Tyr Ser Thr Phe Ala Cys Glu Asn Pro Asn Ser Thr Arg Val Ser Asp
              245              250              255

Phe Arg Thr Ala Asn Cys Ser
              260

<210> SEQ ID NO 18
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Thr Asn Pro Tyr Ala Arg Gly Pro Asn Pro Thr Ala Ala Ser Leu
1               5                10               15

Glu Ala Ser Ala Gly Pro Phe Thr Val Arg Ser Phe Thr Val Ser Arg
         20               25               30

Pro Ser Gly Tyr Gly Ala Gly Thr Val Tyr Tyr Pro Thr Asn Ala Gly
         35               40               45

Gly Thr Val Gly Ala Ile Ala Ile Val Pro Gly Tyr Thr Ala Arg Gln
    50               55               60

Ser Ser Ile Lys Trp Trp Gly Pro Arg Leu Ala Ser His Gly Phe Val
65               70               75               80

Val Ile Thr Ile Asp Thr Asn Ser Thr Leu Asp Gln Pro Glu Ser Arg
              85               90               95

Ser Ser Gln Gln Met Ala Ala Leu Arg Gln Val Ala Ser Leu Asn Gly
         100              105              110

Asp Ser Ser Ser Pro Ile Tyr Gly Lys Val Asp Thr Ala Arg Met Gly
         115              120              125

Val Met Gly Trp Ser Met Gly Gly Gly Gly Ser Leu Ile Ser Ala Ala
    130              135              140

Asn Asn Pro Ser Leu Lys Ala Ala Ala Pro Gln Ala Pro Trp Asp Ser
145              150              155              160

Ser Thr Asn Phe Ser Ser Val Thr Val Pro Thr Leu Ile Phe Ala Cys
              165              170              175

Glu Asn Asp Ser Ile Ala Pro Val Asn Ser Ser Ala Leu Pro Ile Tyr
         180              185              190
```

```
Asp Ser Met Ser Arg Asn Ala Lys Gln Phe Leu Glu Ile Lys Gly Gly
        195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
            245                 250                 255

Phe Arg Thr Ala Asn Cys Ser
        260
```

```
<210> SEQ ID NO 19
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19
```

```
Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
        115                 120                 125

Val Met Gly Trp Ser Met Gly Gly Gly Gly Ser Leu Ile Ser Ala Ala
    130                 135                 140

Asn Asn Pro Ser Leu Lys Ala Ala Ala Pro Gln Ala Pro Trp Asp Ser
145                 150                 155                 160

Ser Thr Asn Phe Ser Ser Val Thr Val Pro Thr Leu Ile Phe Ala Cys
            165                 170                 175

Glu Asn Asp Ser Ile Ala Pro Val Asn Ser Ser Ala Leu Pro Ile Tyr
        180                 185                 190

Asp Ser Met Ser Gln Asn Ala Lys Gln Phe Leu Glu Ile Asn Gly Gly
        195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
            245                 250                 255

Phe Arg Thr Ala Asn Cys Ser
        260
```

```
<210> SEQ ID NO 20
```

```
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
        50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
                100                 105                 110

Asp Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
        130                 135                 140

Asn Asn Pro Ser Leu Lys Ala Ala Ala Pro Gln Ala Pro Trp Asp Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
                180                 185                 190

Asp Ser Met Ser Gln Asn Ala Lys Gln Phe Leu Glu Ile Lys Gly Gly
            195                 200                 205

Ser His Ser Cys Ala Asn Ser Gly Asn Ser Asn Gln Ala Leu Ile Gly
        210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Arg Val Ser Asp
                245                 250                 255

Phe Arg Thr Ala Asn Cys Ser
            260

<210> SEQ ID NO 21
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45
```

```
Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
                100                 105                 110

Thr Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
    130                 135                 140

Asn Asn Pro Ser Leu Lys Ala Ala Ala Pro Gln Ala Pro Trp His Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
                180                 185                 190

Asp Ser Met Ser Arg Asn Ala Lys Gln Phe Leu Glu Ile Lys Gly Gly
            195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
                260
```

```
<210> SEQ ID NO 22
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Thr Asn Pro Tyr Ala Arg Gly Pro Asn Pro Thr Ala Ala Ser Leu
1                   5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
                100                 105                 110

Asp Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
```

-continued

```
        130                 135                 140

Asn Asn Pro Ser Leu Lys Ala Ala Ala Pro Gln Ala Pro Trp His Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
                180                 185                 190

Asp Ser Met Ser Arg Asn Ala Lys Gln Phe Leu Glu Ile Asn Gly Gly
            195                 200                 205

Ser His Ser Cys Ala Asn Ser Gly Asn Ser Asn Gln Ala Leu Ile Gly
        210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
                260

<210> SEQ ID NO 23
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Thr Asn Pro Tyr Ala Arg Gly Pro Asn Pro Thr Ala Ala Ser Leu
1                   5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
        50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
                100                 105                 110

Thr Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
        130                 135                 140

Asn Asn Pro Ser Leu Lys Ala Ala Ala Pro Gln Ala Pro Trp His Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
                180                 185                 190

Asp Ser Met Ser Gln Asn Ala Lys Gln Phe Leu Glu Ile Asn Gly Gly
            195                 200                 205

Ser His Ser Cys Ala Asn Ser Gly Asn Ser Asn Gln Ala Leu Ile Gly
        210                 215                 220
```

```
Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
            260

<210> SEQ ID NO 24
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
    130                 135                 140

Asn Asn Pro Ser Leu Lys Ala Ala Ala Pro Gln Ala Pro Trp His Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
            180                 185                 190

Asp Ser Met Ser Arg Asn Ala Lys Gln Phe Leu Glu Ile Lys Gly Gly
            195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
            260

<210> SEQ ID NO 25
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 25

```
Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
            50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Leu Asp Gln Pro Glu Ser Arg
                85                  90                  95

Ser Ser Gln Gln Met Ala Ala Leu Arg Gln Val Ala Ser Leu Asn Gly
            100                 105                 110

Thr Ser Ser Ser Pro Ile Tyr Gly Lys Val Asp Thr Ala Arg Met Gly
            115                 120                 125

Val Met Gly Trp Ser Met Gly Gly Gly Gly Ser Leu Ile Ser Ala Ala
        130                 135                 140

Asn Asn Pro Ser Leu Lys Ala Ala Ala Pro Gln Ala Pro Trp His Ser
145                 150                 155                 160

Ser Thr Asn Phe Ser Ser Val Thr Val Pro Thr Leu Ile Phe Ala Cys
                165                 170                 175

Glu Asn Asp Ser Ile Ala Pro Val Asn Ser Ser Ala Leu Pro Ile Tyr
            180                 185                 190

Asp Ser Met Ser Gln Asn Ala Lys Gln Phe Leu Glu Ile Lys Gly Gly
            195                 200                 205

Ser His Ser Cys Ala Asn Ser Gly Asn Ser Asn Gln Ala Leu Ile Gly
        210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
                260
```

```
<210> SEQ ID NO 26
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 26

```
Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
            50                  55                  60

Ser Ser Ile Lys Trp Trp Gly Pro Arg Leu Ala Ser His Gly Phe Val
65                  70                  75                  80
```

```
Val Ile Thr Ile Asp Thr Asn Ser Thr Leu Asp Gln Pro Glu Ser Arg
            85              90              95

Ser Ser Gln Gln Met Ala Ala Leu Arg Gln Val Ala Ser Leu Asn Gly
            100             105             110

Asp Ser Ser Ser Pro Ile Tyr Gly Lys Val Asp Thr Ala Arg Met Gly
            115             120             125

Val Met Gly Trp Ser Met Gly Gly Gly Ser Leu Ile Ser Ala Ala
    130             135             140

Asn Asn Pro Ser Leu Lys Ala Ala Ala Pro Gln Ala Pro Trp His Ser
145             150             155             160

Ser Thr Asn Phe Ser Ser Val Thr Val Pro Thr Leu Ile Phe Ala Cys
            165             170             175

Glu Asn Asp Ser Ile Ala Pro Val Asn Ser Ser Ala Leu Pro Ile Tyr
            180             185             190

Asp Ser Met Ser Gln Asn Ala Lys Gln Phe Leu Glu Ile Asn Gly Gly
            195             200             205

Ser His Ser Cys Ala Asn Ser Gly Asn Ser Asn Gln Ala Leu Ile Gly
    210             215             220

Lys Lys Gly Val Ala Trp Met Lys Arg Phe Met Asp Asn Asp Thr Arg
225             230             235             240

Tyr Ser Thr Phe Ala Cys Glu Asn Pro Asn Ser Thr Ala Val Ser Asp
            245             250             255

Phe Arg Thr Ala Asn Cys Ser
            260
```

```
<210> SEQ ID NO 27
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

```
Gln Thr Asn Pro Tyr Ala Arg Gly Pro Asn Pro Thr Ala Ala Ser Leu
1               5               10              15

Glu Ala Ser Ala Gly Pro Phe Thr Val Arg Ser Phe Thr Val Ser Arg
            20              25              30

Pro Ser Gly Tyr Gly Ala Gly Thr Val Tyr Tyr Pro Thr Asn Ala Gly
            35              40              45

Gly Thr Val Gly Ala Ile Ala Ile Val Pro Gly Tyr Thr Ala Arg Gln
    50              55              60

Ser Ser Ile Lys Trp Trp Gly Pro Arg Leu Ala Ser His Gly Phe Val
65              70              75              80

Val Ile Thr Ile Asp Thr Asn Ser Thr Leu Asp Gln Pro Glu Ser Arg
            85              90              95

Ser Ser Gln Gln Met Ala Ala Leu Arg Gln Val Ala Ser Leu Asn Gly
            100             105             110

Asp Ser Ser Ser Pro Ile Tyr Gly Lys Val Asp Thr Ala Arg Met Gly
            115             120             125

Val Met Gly Trp Ser Met Gly Gly Gly Ser Leu Ile Ser Ala Ala
    130             135             140

Asn Asn Pro Ser Leu Lys Ala Ala Ala Pro Gln Ala Pro Trp His Ser
145             150             155             160

Ser Thr Asn Phe Ser Ser Val Thr Val Pro Thr Leu Ile Phe Ala Cys
```

-continued

```
                    165                 170                 175
Glu Asn Asp Ser Ile Ala Pro Val Asn Ser Ser Ala Leu Pro Ile Tyr
                180                 185                 190

Asp Ser Met Ser Gln Asn Ala Lys Gln Phe Leu Glu Ile Lys Gly Gly
            195                 200                 205

Ser His Ser Cys Ala Asn Ser Gly Asn Ser Asn Gln Ala Leu Ile Gly
        210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
                260

<210> SEQ ID NO 28
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
        50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Phe Asp Tyr Pro Ser Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
        115                 120                 125

Val Met Gly His Ser Met Gly Gly Gly Ala Ser Leu Arg Ser Ala Ala
    130                 135                 140

Asn Asn Pro Ser Leu Lys Ala Ala Ile Pro Gln Ala Pro Trp Asp Ser
145                 150                 155                 160

Gln Thr Asn Phe Ser Ser Val Thr Val Pro Thr Leu Ile Phe Ala Cys
                165                 170                 175

Glu Asn Asp Ser Ile Ala Pro Val Asn Ser His Ala Leu Pro Ile Tyr
                180                 185                 190

Asp Ser Met Ser Arg Asn Ala Lys Gln Phe Leu Glu Ile Lys Gly Gly
            195                 200                 205

Ser His Ser Cys Ala Asn Ser Gly Asn Ser Asn Gln Ala Leu Ile Gly
        210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255
```

-continued

```
Phe Arg Thr Ala Asn Cys Ser
        260

<210> SEQ ID NO 29
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Phe Asp Tyr Pro Glu Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
            115                 120                 125

Val Met Gly His Ser Met Gly Gly Gly Ala Ser Leu Arg Ser Ala Ala
    130                 135                 140

Asn Asn Pro Ser Leu Lys Ala Ala Ile Pro Gln Ala Pro Trp Asp Ser
145                 150                 155                 160

Gln Thr Asn Phe Ser Ser Val Thr Val Pro Thr Leu Ile Phe Ala Cys
                165                 170                 175

Glu Asn Asp Ser Ile Ala Pro Val Asn Ser His Ala Leu Pro Ile Tyr
            180                 185                 190

Asp Ser Met Ser Arg Asn Ala Lys Gln Phe Leu Glu Ile Asn Gly Gly
        195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
        260

<210> SEQ ID NO 30
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Thr Asn Pro Tyr Ala Arg Gly Pro Asn Pro Thr Ala Ala Ser Leu
1               5                   10                  15
```

-continued

```
Glu Ala Ser Ala Gly Pro Phe Thr Val Arg Ser Phe Thr Val Ser Arg
        20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
        50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Phe Asp Tyr Pro Ser Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
            115                 120                 125

Val Met Gly His Ser Met Gly Gly Gly Ala Ser Leu Arg Ser Ala Ala
        130                 135                 140

Asn Asn Pro Ser Leu Lys Ala Ala Ile Pro Gln Ala Pro Trp Asp Ser
145                 150                 155                 160

Gln Thr Asn Phe Ser Ser Val Thr Val Pro Thr Leu Ile Phe Ala Cys
                165                 170                 175

Glu Asn Asp Ser Ile Ala Pro Val Asn Ser His Ala Leu Pro Ile Tyr
            180                 185                 190

Asp Ser Met Ser Gln Asn Ala Lys Gln Phe Leu Glu Ile Asn Gly Gly
        195                 200                 205

Ser His Ser Cys Ala Asn Ser Gly Asn Ser Asn Gln Ala Leu Ile Gly
        210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
            260
```

```
<210> SEQ ID NO 31
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

```
Gln Thr Asn Pro Tyr Ala Arg Gly Pro Asn Pro Thr Ala Ala Ser Leu
1                   5                   10                  15

Glu Ala Ser Ala Gly Pro Phe Thr Val Arg Ser Phe Thr Val Ser Arg
        20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
        50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Phe Asp Tyr Pro Ser Ser Arg
                85                  90                  95

Ser Ser Gln Gln Met Ala Ala Leu Arg Gln Val Ala Ser Leu Asn Gly
            100                 105                 110
```

-continued

```
Asp Ser Ser Ser Pro Ile Tyr Gly Lys Val Asp Thr Ala Arg Met Gly
        115                 120                 125

Val Met Gly His Ser Met Gly Gly Gly Ala Ser Leu Arg Ser Ala Ala
    130                 135                 140

Asn Asn Pro Ser Leu Lys Ala Ala Ile Pro Gln Ala Pro Trp Asp Ser
145                 150                 155                 160

Gln Thr Asn Phe Ser Ser Val Thr Val Pro Thr Leu Ile Phe Ala Cys
                165                 170                 175

Glu Asn Asp Ser Ile Ala Pro Val Asn Ser His Ala Leu Pro Ile Tyr
                180                 185                 190

Asp Ser Met Ser Gln Asn Ala Lys Gln Phe Leu Glu Ile Lys Gly Gly
        195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
            260

<210> SEQ ID NO 32
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Phe Asp Tyr Pro Glu Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
        115                 120                 125

Val Met Gly His Ser Met Gly Gly Gly Ala Ser Leu Arg Ser Ala Ala
    130                 135                 140

Asn Asn Pro Ser Leu Lys Ala Ala Ile Pro Gln Ala Pro Trp Asp Ser
145                 150                 155                 160

Gln Thr Asn Phe Ser Ser Val Thr Val Pro Thr Leu Ile Phe Ala Cys
                165                 170                 175

Glu Asn Asp Ser Ile Ala Pro Val Asn Ser His Ala Leu Pro Ile Tyr
                180                 185                 190

Asp Ser Met Ser Arg Asn Ala Lys Gln Phe Leu Glu Ile Lys Gly Gly
```

-continued

```
                195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
            260

<210> SEQ ID NO 33
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
                20                  25                  30

Pro Ser Gly Tyr Gly Ala Gly Thr Val Tyr Tyr Pro Thr Asn Ala Gly
            35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Phe Asp Tyr Pro Glu Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
            115                 120                 125

Val Met Gly His Ser Met Gly Gly Gly Ala Ser Leu Arg Ser Ala Ala
    130                 135                 140

Asn Asn Pro Ser Leu Lys Ala Ala Ile Pro Gln Ala Pro Trp Asp Ser
145                 150                 155                 160

Gln Thr Asn Phe Ser Ser Val Thr Val Pro Thr Leu Ile Phe Ala Cys
                165                 170                 175

Glu Asn Asp Ser Ile Ala Pro Val Asn Ser His Ala Leu Pro Ile Tyr
            180                 185                 190

Asp Ser Met Ser Gln Asn Ala Lys Gln Phe Leu Glu Ile Asn Gly Gly
            195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
            260

<210> SEQ ID NO 34
<211> LENGTH: 263
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Thr Asn Pro Tyr Ala Arg Gly Pro Asn Pro Thr Ala Ala Ser Leu
1               5                   10                  15

Glu Ala Ser Ala Gly Pro Phe Thr Val Arg Ser Phe Thr Val Ser Arg
            20                  25                  30

Pro Ser Gly Tyr Gly Ala Gly Thr Val Tyr Tyr Pro Thr Asn Ala Gly
        35                  40                  45

Gly Thr Val Gly Ala Ile Ala Ile Val Pro Gly Tyr Thr Ala Arg Gln
    50                  55                  60

Ser Ser Ile Lys Trp Trp Gly Pro Arg Leu Ala Ser His Gly Phe Val
65                  70                  75                  80

Val Ile Thr Ile Asp Thr Asn Ser Thr Phe Asp Tyr Pro Glu Ser Arg
                85                  90                  95

Ser Ser Gln Gln Met Ala Ala Leu Arg Gln Val Ala Ser Leu Asn Gly
            100                 105                 110

Asp Ser Ser Ser Pro Ile Tyr Gly Lys Val Asp Thr Ala Arg Met Gly
        115                 120                 125

Val Met Gly His Ser Met Gly Gly Gly Ala Ser Leu Arg Ser Ala Ala
    130                 135                 140

Asn Asn Pro Ser Leu Lys Ala Ala Ile Pro Gln Ala Pro Trp Asp Ser
145                 150                 155                 160

Gln Thr Asn Phe Ser Ser Val Thr Val Pro Thr Leu Ile Phe Ala Cys
                165                 170                 175

Glu Asn Asp Ser Ile Ala Pro Val Asn Ser His Ala Leu Pro Ile Tyr
            180                 185                 190

Asp Ser Met Ser Gln Asn Ala Lys Gln Phe Leu Glu Ile Lys Gly Gly
        195                 200                 205

Ser His Ser Cys Ala Asn Ser Gly Asn Ser Asn Gln Ala Leu Ile Gly
    210                 215                 220

Lys Lys Gly Val Ala Trp Met Lys Arg Phe Met Asp Asn Asp Thr Arg
225                 230                 235                 240

Tyr Ser Thr Phe Ala Cys Glu Asn Pro Asn Ser Thr Ala Val Ser Asp
                245                 250                 255

Phe Arg Thr Ala Asn Cys Ser
            260

<210> SEQ ID NO 35
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Asn Phe Pro Arg Ala Ser Arg Leu Met Gln Ala Ala Val Leu Gly
1               5                   10                  15

Gly Leu Met Ala Val Ser Ala Ala Ala Thr Ala Gln Thr Asn Pro Tyr
            20                  25                  30

Ala Leu Gly Pro Asn Pro Thr Ala Ala Ser Leu Glu Ala Ser Ala Gly
        35                  40                  45
```

-continued

```
Pro Phe Thr Val Arg Ser Phe Thr Val Ala Arg Pro Thr Gly Tyr Gly
    50                  55                  60

Ala Gly Thr Val Tyr Tyr Pro Thr Asn Ala Gly Gly Thr Val Gly Ala
65                  70                  75                  80

Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Leu Asp Gln Pro Ser Ser Arg Ser Ser Gln Gln Met
        115                 120                 125

Ala Ala Leu Arg Gln Val Ala Ser Leu Asn Gly Thr Ser Ser Ser Pro
    130                 135                 140

Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                165                 170                 175

Lys Ala Ala Ala Pro Gln Ala Pro Trp Asp Ser Ser Thr Asn Phe Ser
            180                 185                 190

Ser Val Thr Val Pro Thr Leu Ile Phe Ala Cys Glu Asn Asp Ser Val
        195                 200                 205

Ala Pro Val Asn Ser Ser Ala Leu Pro Ile Tyr Asp Ser Met Ser Gln
    210                 215                 220

Asn Ala Lys Gln Phe Leu Glu Ile Asn Gly Gly Ser His Ser Cys Cys
225                 230                 235                 240

Asn Ser Gly Asn Ser Asn Gln Ala Leu Ile Gly Lys Lys Gly Val Ala
                245                 250                 255

Trp Met Lys Arg Phe Met Asp Asn Asp Thr Arg Tyr Ser Thr Phe Ala
            260                 265                 270

Cys Glu Asn Pro Asn Ser Thr Arg Val Ser Asp Phe Arg Thr Ala Asn
        275                 280                 285

Cys Ser
    290
```

```
<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

His His His His His His
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Tyr Lys Asp Asp Asp Asp Lys
1               5
```